US006916478B2

(12) United States Patent
Kadurugamuwa et al.

(10) Patent No.: US 6,916,478 B2
(45) Date of Patent: Jul. 12, 2005

(54) VACCINES AND PHARMACEUTICAL COMPOSITIONS USING MEMBRANE VESICLES OF MICROORGANISMS, AND METHODS FOR PREPARING SAME

(75) Inventors: Jagath L. Kadurugamuwa, Verona, NJ (US); Terry J. Beveridge, Elora (CA)

(73) Assignee: University of Guelph, Ontario (CA)

( * ) Notice: Subject to any disclaimer, the term of this patent is extended or adjusted under 35 U.S.C. 154(b) by 0 days.

(21) Appl. No.: 10/236,557

(22) Filed: Sep. 6, 2002

(65) Prior Publication Data

US 2004/0013689 A1 Jan. 22, 2004

Related U.S. Application Data

(63) Continuation of application No. 09/370,860, filed on Aug. 9, 1999, now abandoned, which is a continuation of application No. 08/691,484, filed on Aug. 2, 1996, now abandoned.
(60) Provisional application No. 60/001,903, filed on Aug. 4, 1995.

(51) Int. Cl.$^7$ .............................................. A61K 39/02
(52) U.S. Cl. ................. 424/234.1; 424/184.1; 424/197.11; 435/243; 435/245
(58) Field of Search .................. 424/234.1, 184.1, 424/197.11; 435/243, 245

(56) References Cited

U.S. PATENT DOCUMENTS

| 4,394,448 A | 7/1983 | Szoka, Jr. et al. |
| 4,945,050 A | 7/1990 | Sanford et al. |
| 4,971,801 A | 11/1990 | Urban |
| 5,000,958 A | 3/1991 | Fountain et al. |
| 5,186,941 A | 2/1993 | Callahan et al. |
| 5,223,412 A | 6/1993 | Wight et al. |
| 5,242,947 A | 9/1993 | Cherskey et al. |
| 5,858,698 A | 1/1999 | Armstrong et al. |

FOREIGN PATENT DOCUMENTS

| EP | 0 061 253 | 9/1982 |
| EP | 0 564 689 | 10/1993 |
| JP | 43005011 | 2/1968 |
| SU | 1708351 | 1/1992 |
| WO | WO 90/06696 | 6/1990 |
| WO | WO 91/09616 | 7/1991 |
| WO | WO 91/11174 | 8/1991 |
| WO | WO 92/05194 | 4/1992 |
| WO | WO 93/22423 | 11/1993 |
| WO | WO 94/04677 | 3/1994 |
| WO | WO 94/08021 | 4/1994 |
| WO | WO 95/23211 | 8/1995 |

OTHER PUBLICATIONS

Newland, et al., *Vaccine*, 10:766–776 (1992).
Mills, et al., *Vaccine*, 6:116–122 (1988).
Tijhaar, et al., *Vaccine*, 12:1004–1011 (1994).
Wills, et al., *J. of Virol.*, 68:6605–6618 (1994).
Tan and Worobec, *FEMS Microbial. Letts.*, 106:281–286 (1993).
Bergmann, et al., *Infect. Immun.*, 57:2187–2195 (1989).
Bernadsky, et al., *J. Bacteriol.*, 176:5225–5232 (1994).
Kadurugamuwa, et al., *Antimicrob. Agents Chemother.*, 37:715–721 (1993).
Lightfoot and Lam, *J. Bacteriol.*, 173:5624–5630 (1991).
Martin and Beveridge, *Antimicrob. Agents Chemother.*, 29:1079–1087 (1986).
Rivera, et al., *J. Bacteriol.*, 170:512–521 (1988).
Berk, et al., *Infect. Immun.*, 55:1728–1730 (1987).
Vasil, et al., *Antibiot. Chemother.*, 44:34–47 (1991).
Ingram, et al., *Can. J. Microbiol.*, 19:1407–1415 (1973).
Poole and Hancock, *FEMS Microbiol. Letts.*, 16:25–29 (1983).
Hastie, et al., *Infect. Immun.*, 40:506–513, (1983).
Kessler, et al., *J. Biol. Chem.*, 268:7503–7508 (1993).
Lazdusniski, et al., *Biochemie*, 72:147–156 (1990).
Duoung, et al., *Gene*, 121:47–54 (1992).
Guzzo, et al., *J. Bacteriol.*, 173:5290–5297 (1991).
Hamood, et al., *Infect. Immun.*, 60:510–517 (1992).
Kadurugamuwa, et al., *J. Bacteriol.*, 175:5798–5805 (1993).
Kadurugamuwa, et al., *Infect. Immun.*, 59:3463–3471 (1991).
Beveridge, *ASM News*, 61:125–130 (1995).
Guzman, et al., *Infect. Immun.*, 59:4391–4397 (1991).
Kadurugamuwa, et al., Abstract and Poster, 94th ASM, Las Vegas, May 23–27, 1994.
Kadurugamuwa, et al., Abstract ICAAC, Orlando, Florida, Oct. 4–7, 1994.
Kadurugamuwa et al., Abstract and Poster, 95th ASM General Meeting, Wash., DC, May 21–25, 1995.
Beveridge, CBDN Projects Annual Report, Group 2D, Aug. 1993.
Kadurugamuwa, et al., *J. Bacteriol.*, 177: 14, 3998–4008 (1995).
Tetz, et al., "Ultrastructure of the surface film of bacterial colonies," *Journal of General Microbiology*, vol. 139, pp. 855–858 (1993).

*Primary Examiner*—Lynette R. F. Smith
*Assistant Examiner*—Robert A. Zeman
(74) *Attorney, Agent, or Firm*—Bryan Cave LLP

(57) ABSTRACT

The invention relates to novel vaccines and pharmaceutical compositions using membrane vesicles of microorganisms, methods for preparing same, and their use in the prevention and treatment of infectious diseases.

10 Claims, 35 Drawing Sheets

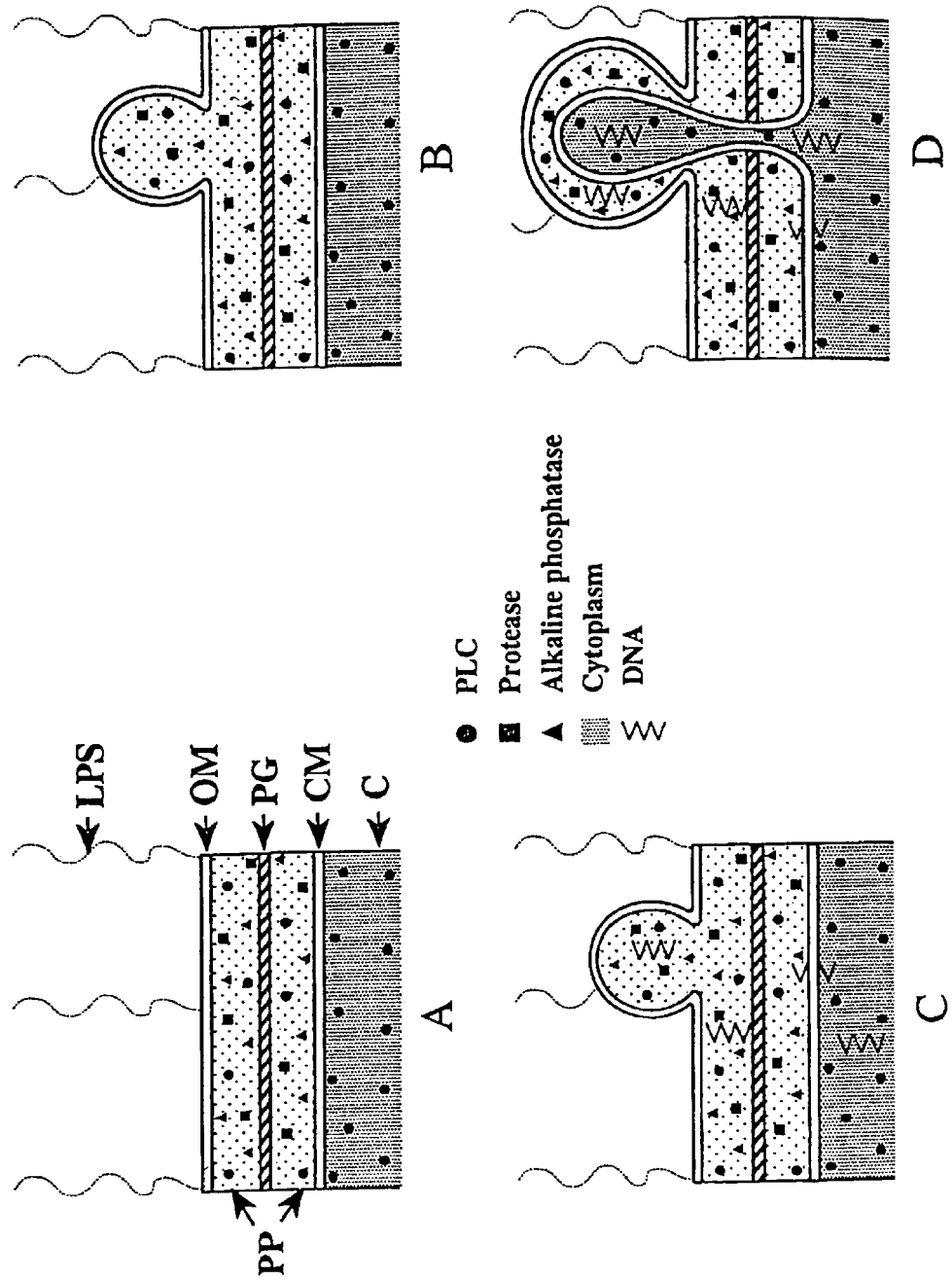

a b

Delivery of drugs into eukaryotic cells using MVs.
Effect of g-MV on intracellular *S. flexneri*.

Fig

VACCINES AND PHARMACEUTICAL COMPOSITIONS USING MEMBRANE VESICLES OF MICROORGANISMS, AND METHODS FOR PREPARING SAME

This is a continuation of U.S. application Ser. No. 09/370,860, filed Aug. 9, 1999, now abandoned, which is a continuation of U.S. application Ser. No. 08/691,484, filed Aug. 2, 1996, now abandoned, which claims benefit under Title 35, United States Code §119(e) of Provisional Application No. 60/001,903, filed Aug. 4, 1995, which applications are incorporated herein by reference.

FIELD OF THE INVENTION

The invention relates to novel vaccines and pharmaceutical compositions using membrane vesicles of microorganisms, methods for preparing same, and their use in the prevention and treatment of infectious diseases.

BACKGROUND OF THE INVENTION

Conventional therapeutic treatments for infectious diseases are becoming increasingly ineffective with the emergence of resistant mutant strains of infectious agents. Antimicrobial agents have been widely described for the treatment of bacterial infections. Many improvements in the administration of antimicrobial agents have been suggested for treating drug resistant mutants; for enhancing therapeutic activity in the treatment of specific infections; and, for lessening the toxicity of individual drugs. These improvements include the development of synthetic analogues and administration of combinations of antibiotics. A number of delivery systems have also been developed for gradually releasing antimicrobial agents in vivo. One approach to obtaining prolonged release of an antimicrobial agent has been to encapsulate the agent in a vesicle known as a liposome. Liposomes are typically micellular particles which are spherical in form and which are derived from a lipid which forms a layered membrane. Typically liposomes are prepared from a phospholipid such as distearoyl phosphatidyl-choline or lecithin. A liposome may be a simple shell (a unilamellar vesicle) or it may form in multiple layers (multilamellar vesicle). However, liposome preparations have a number of disadvantages including the wide heterogeneity in size distribution, the number of lamellae, and the low trapping efficiency of the aqueous space which restricts the ability to encapsulate large molecules. Liposomes are also difficult and costly to produce.

Notwithstanding the advances in antimicrobial agents, new therapeutic agents and delivery vehicles are required particularly for the treatment of infectious diseases caused by resistant mutants and for the treatment of mixed bacterial infections.

Conventional prophylactic treatments for infectious diseases are also becoming increasingly ineffective with the emergence of resistant mutant strains of infectious agents. Vaccines for the prophylaxis of infectious diseases have been developed which incorporate whole attenuated organisms, cell lysates, culture supernatants or extracts of the infectious agents. There has been considerable interest in improving existing vaccines since they typically contain fractions having physical or chemical characteristics which result in toxicity or undesired immune responses.

In order to address these problems attempts are being made to use recombinant DNA techniques to express protective antigens such as lipopolysaccharide from pathogenic bacteria in live, attenuated, carrier strains. These hybrid strains have been demonstrated to be effective vaccine strains since they cannot replicate in vivo, but can still invade and deliver the antigens to host tissue to engender an immune response. However, the use of genetic procedures to transfer foreign genes into attenuated strains has several disadvantages; for example, instability of cloned genes, expression of antibiotic resistance following strain construction, reversion to virulence, accumulation of recombinant antigen in cytoplasm, and poor surface expression for recognition by the immune system. Recombinant vaccines are also costly to make. The construction of a multivalent vaccine is even further complicated due to many variables such as the necessity to develop several constitutive expression systems.

SUMMARY OF THE INVENTION

The present inventors have demonstrated that surface antigens such as lipopolysaccharide can be transferred from a bacteria using membrane vesicles. In particular, the present inventors introduced highly specific antigenic factors from pathogenic bacteria into the surface of avirulent or attenuated strains using membrane vesicles. Membrane vesicles from *Shigella flexneri* and *Pseudomonas aeruginosa* were isolated and fused with whole cells of *E. coli* or *S. typhi*. The integration of antigens from *Shigella flexneri* and *Pseudomonas aeruginosa* into the surface of the avirulent strains was confirmed using electron microscopy of double immunogold-labelled cells, and Western immunoblots. The avirulent strains with integrated surface antigens from the pathogenic bacteria induce immune responses against the antigens. The antigens are stable and continuously expressed on the surface of a carrier strain, and once in the host tissue the carrier strain stops growing (but remains viable) and outer membrane turnover is arrested. The outer membrane antigens will not be released nor replaced once the carrier strain invades the mucosal surface.

The use of membrane vesicles to produce a vaccine in accordance with the present invention has distinct advantages over other methods for generating vaccines. MVs are simply prepared and they readily fuse to carrier strains without complicated mixing formulations. The fusion is thermodynamically stable as it represents a response of two bilayered lipid-protein membranes interacting with one another.

The use of membrane vesicles also permits the simultaneous expression of multiple protective antigens (e.g. LPS and OMPs) from a number of pathogens in a single carrier strain, and this multivalent carrier strain then delivers the heterologous antigens to the immune system. The present invention provides an economical method for inducing protective immunity against a range of serotypes or antigenic variants by fusion of MVs from such pathogens. This eliminates the potential disadvantage of selecting antigenic variants that would become resistant to the antibodies. The present invention also permits the tailoring of vaccines to match differences in serotype distribution of disease in endemic areas.

Broadly stated, the present invention relates to a vaccine against an infectious disease caused by an infectious agent comprising a carrier strain having a membrane vesicle of a microorganism integrated into the cell surface of the carrier strain, wherein the membrane vesicle has an amount of an antigen associated with its cell surface which is effective to provide protection against the infectious agent. The infectious agent may be a microorganism which produces membrane vesicles, or a microorganism which does not produce membrane vesicles.

In accordance with one embodiment of the invention a vaccine against infectious diseases caused by a microorganism which produces membrane vesicles is provided which comprises a carrier strain having a membrane vesicle of the microorganism integrated into the cell surface of the carrier strain. The membrane vesicle may be a natural membrane vesicle of the microorganism, or it may be produced by treating the microorganism with a surface-active agent.

Multivalent vaccines against infectious diseases caused by different infectious agents are also contemplated comprising a carrier strain having membrane vesicles integrated into the cell surface of the carrier strain, wherein the membrane vesicles have amounts of antigens associated with their surfaces which are effective to provide protection against the infectious agents. In an embodiment of the invention, a multivalent vaccine is provided which comprises a carrier strain having at least two membrane vesicles from at least two different microorganisms integrated into the cell surface of the carrier strain, or comprising at least two carrier strains each containing a membrane vesicle from different microorganisms integrated into the cell surface of each of the carrier strains.

The invention also relates to a method of preparing a vaccine against an infectious disease caused by an infectious agent comprising integrating a membrane vesicle of a microorganism into the cell surface of a carrier strain wherein the membrane vesicle has an amount of an antigen associated with its surface which is effective to provide protection against the infectious agent. In an embodiment, the invention relates to a method of preparing a vaccine against infectious diseases caused by a microorganism which produces membrane vesicles which comprises integrating a membrane vesicle produced by the microorganism into the cell surface of a carrier strain.

The invention further relates to a method of preparing a multivalent vaccine against infectious diseases caused by different infectious agents comprising integrating membrane vesicles into the cell surface of a carrier strain, wherein the membrane vesicles have amounts of antigens associated with their surfaces which are effective to provide protection against the infectious agents. The membrane vesicles may be produced by the infectious agents or the membrane vesicles may be obtained from microorganisms which produce membrane vesicles and which are engineered to produce one or more of the antigens so that they are associated with the surface of the membrane vesicles. In an embodiment, the invention relates to a method of preparing a multivalent vaccine against infectious diseases caused by different microorganisms which produce membrane vesicles which comprises integrating membrane vesicles produced by the microorganisms into the cell surface of one or more carrier strains.

The invention still further relates to antibodies against a membrane vesicle of a microorganism for use as a means of passive immunization.

The invention also provides a method for screening for an immunogenic antigen of a pathogen comprising (a) providing a membrane vesicle having a test antigen associated with its surface; (b) vaccinating an animal with the membrane vesicle; and (c) challenging the animal with the pathogen to determine if the test antigen provides protection against the pathogen.

The present inventors have also found that a majority of bacteriolytic enzymes with peptidoglycan hydrolase, lipase, or proteolytic activity are not soluble, and they are concentrated and entrapped within the membrane vesicles of microorganisms. Significantly, the present inventors have shown that these membrane vesicles containing bacteriolytic enzymes are able to lyse gram-negative and gram-positive bacteria. In addition, gentamicin-induced membrane vesicles were found to be more lytic than natural membrane vesicles indicating a synergistic effect of the bacteriolytic enzymes cell-wall degrading activity and the antimicrobial agent's activity.

Therefore, the present invention also contemplates a pharmaceutical composition comprising a membrane vesicle of a microorganism containing one or more enzymes with peptidoglycan hydrolase, lipase, or proteolytic activity, and optionally a therapeutic agent, in an amount effective to have a bactericidal effect on gram-negative and/or gram-positive bacterial pathogens and a pharmaceutically acceptable vehicle or diluent. The membrane vesicle may be a natural membrane vesicle of a microorganism, or it may be produced by treating a microorganism with a surface-active agent. The invention further contemplates a method of treating an infectious disease caused by a gram-negative and/or gram-positive bacterial pathogen comprising administering membrane vesicles of one or more microorganisms containing one or more enzymes with peptidoglycan hydrolase, lipase, or proteolytic activity, and optionally a therapeutic agent, in an amount effective to have a bactericidal effect on the gram-negative and/or gram-positive bacterial pathogens.

The present inventors have also found that impermeable antimicrobial agents such as gentamicin can be introduced into epithelial cells using gentamicin-induced membrane vesicles from *Shigella flexneri*. Thus, the membrane vesicles may be used for the delivery of antimicrobial agents into a host.

Accordingly, the invention also relates to a composition comprising membrane vesicles of a microorganism containing a therapeutic agent in an amount which is effective to introduce the therapeutic agent into a host. The invention also relates to a method for administering a therapeutic agent to a host comprising administering to the host the therapeutic agent encapsulated in a membrane vesicle of a microorganism.

In an embodiment of the invention, a composition is provided comprising membrane vesicles of a microorganism containing an antimicrobial agent, in an amount which is effective to introduce the antimicrobial agent into a host. The invention also relates to a method for administering an antimicrobial agent into a host comprising administering to the host a membrane vesicle of a microorganism containing the antimicrobial agent.

The invention also relates to a method of inserting nucleic acid molecules into a target cell which comprises encapsulating the nucleic acid in a membrane vesicle of a microorganism, and bringing the membrane vesicle in contact with the target cell whereby the nucleic acid molecule is inserted into the cell.

These and other aspects of the present invention will become evident upon reference to the following detailed description and attached drawings. In addition, reference is made herein to various publications, which are hereby incorporated by reference in their entirety.

DESCRIPTION OF THE DRAWINGS

The invention will be better understood with reference to the drawings in which:

FIG. 10 is a schematic diagram showing a model of the events leading to the secretion of certain extracellular enzymes via membrane vesicles in *P. aeruginosa*;

FIG. 26 shows levels of specific antibody responses in sera, lung and gut in mice following oral immunization with MVs from PAO1 or M90T or after integration of the MVs onto Ty21a vaccine strain, where panels (a) to (e) depict the strain-specific antibody responses in serum to (a) PAO1 and (b) M90T, in lung to (c) to PAO1, and to intestinal lavage fluids to (d) M90T and (e) Ty21a.

DETAILED DESCRIPTION OF THE INVENTION

I. Membrane Vesicles

Figure 1:
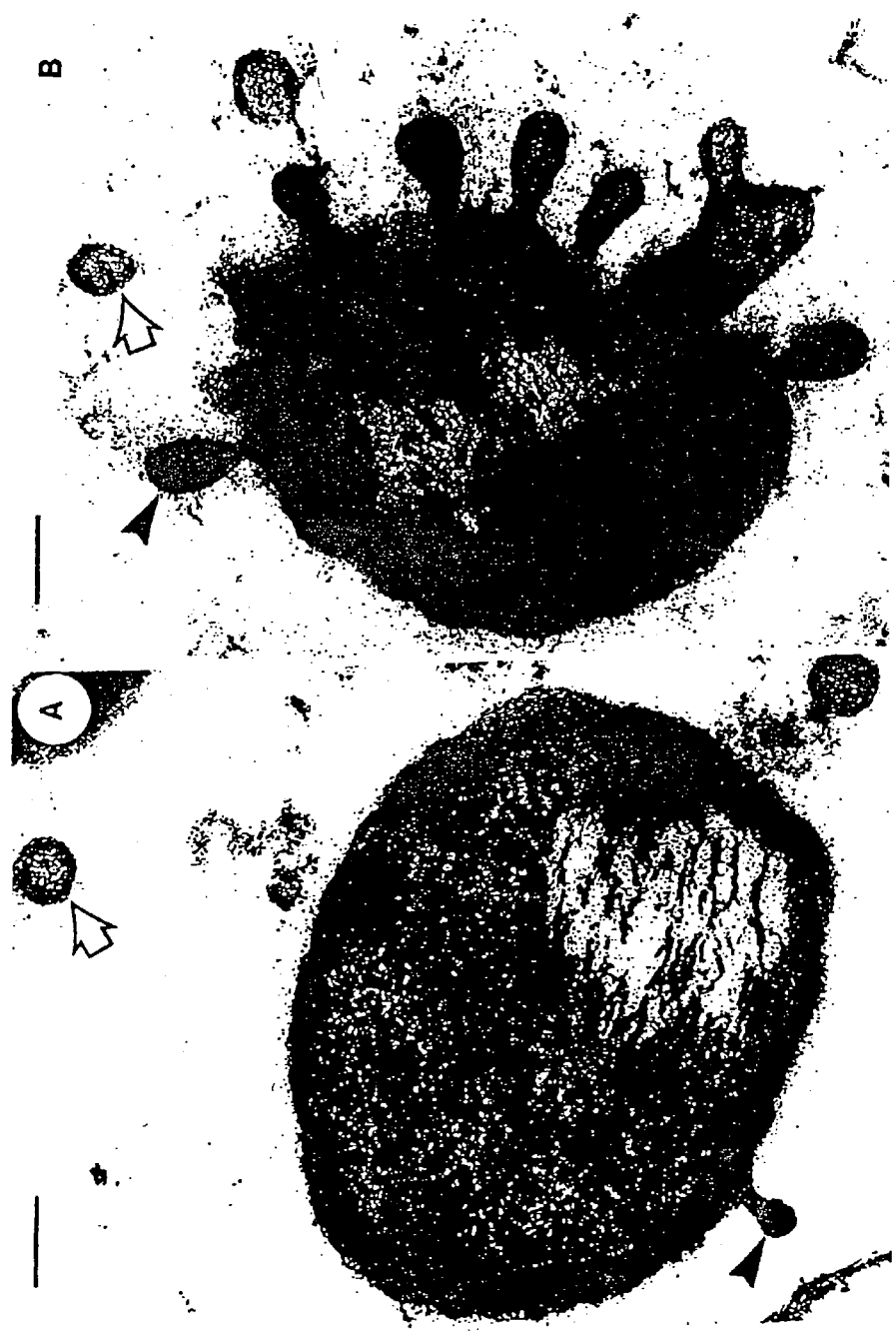
FIG. 1 is a photograph of sections of *P. aeruginosa* cells which were either treated with gentamicin (B), or untreated (A)

The vaccines, methods and compositions of the invention employ membrane vesicles of microorganisms. Membrane vesicles also known as blebs, are little bud-like protrusions formed in the cell wall, outer membrane, cytoplasmic, and/or plasma membrane of a microorganism. When cultured under selected conditions the membrane vesicles break away from the whole cell into the medium. The membrane vesicles are generally spherical, possess a bilayer, and have a diameter of about 10 to 200 nm, preferably 50–150 nm, most preferably 80 to 100 nm.

The membrane vesicles may be natural membrane vesicles of a microorganism which produces membrane vesicles. Natural membrane vesicles contain outer membrane and periplasm components. Natural membrane vesicles are produced without exposing the microorganism to a surface-active agent. Treatment with a surface active agent produces membrane vesicles which are larger than the natural vesicles. These large membrane vesicles typically contain outer membrane, cytoplasmic membrane or plasma membrane components, and cytoplasm. Membrane vesicles produced by treatment with surface-active agents also include natural membrane vesicles. The membrane vesicles used in the vaccine, methods, and compositions of the invention include both natural membrane vesicles and the larger membrane vesicles.

By way of example, natural membrane vesicles of *Pseudomonas aeruginosa* contain mainly B-band LPS, mature periplasmic enzymes and secretory enzymes which are in transit. Secretory enzymes may be mature enzymes or proenzymes; the latter being activated once they are liberated from the cell surface. The antimicrobial agent gentamicin increases the incidence of membrane vesicles and frequently results in membrane vesicles which contain outer membrane, cytoplasmic membrane and/or plasma membrane components. Both types of membrane vesicles are enriched with peptidoglycan-hydrolysing enzymes (i.e., autolysins).

While we do not wish to be bound by any particular models, a proposed model for the formation of membrane vesicles in *P. aeruginosa* is set out in schematic form in FIG. 10. FIG. 10(A) shows the envelope before membrane blebbing is initiated. FIG. 10(B) shows the simplest type of membrane vesicle and is the most frequent natural membrane vesicle. This membrane vesicle is comparatively small, involves only the exfoliation of the outer membrane, and entraps only periplasm. FIG. 10(C) is an extrapolation of FIG. 10(B) in that it includes the entrapment of DNA that has migrated from the cytoplasm to the periplasm and is another possibility for natural membrane vesicles. Although the DNA resembles linear strands, it is possible that both circular or linear complexes could be compartmentalized. FIG. 10(D) shows the production of a more complex membrane vesicle containing both inner and outer membranes as well as some cytoplasmic constituents. Autolysins have been found in both types of membrane vesicles. Surface-active agents such as gentamicin encourage the formation of the membrane vesicles seen in FIG. 10(D).

The membrane vesicles are typically obtained from gram-negative bacteria. Suitable microorganisms for producing the membrane vesicles include *Pseudomonas aeruginosa, Escherichia coli, Salmonella gastroenteritis (typhimirium), S. typhi, S. enteriditis, Shigella flexneri, S. sonnie, S dysenteriae, Neisseria gonorrhoeae, N. meningitides, Haemophilus influenzae H. pleuropneumoniae, Pasteurella haemolytica, P. multilocida, Legionella pneumophila, Treponema pallidum, T. denticola, T. orales, Borrelia burgdorferi, Borrelia* spp. *Leptospira interrogans, Klebsiella pneumoniae, Proteus vulgaris, P. morganii, P. mirabilis, Rickettsia prowazeki, R. typhi, R. richettsii, Porphyromonas* (Bacteriodes) *gingivalis, Chlamydia psittaci, C. pneumoniae, C. trachomatis, Campylobacter jejuni, C. intermedis, C. fetus, Helicobacter pylori, Francisella tularenisis, Vibrio cholerae, Vibrio parahaemolyticus, Bordetella pertussis, Burkholderie pseudomallei, Brucella abortus, B. susi, B. melitensis, B. canis, Spirillum minus, Pseudomonas mallei, Aeromonas hydrophila, A salmonicida,* and *Yersinia pestis.*

In accordance with preferred embodiments of the invention, the microorganism is selected from the bacterial strains *Pseudomonas aeruginosa* H103, PAO1, and ATCC 19660, *Shigella flexneri, S. dysenteriae, Escherichia coli* K12, K30, DH5α, *Salmonella typhi,* and *Neisseria gonorrhoeae* CH811, CS19a.

The present inventors are the first to report the release of membrane vesicles from *Shigella flexneri.* Accordingly, in accordance with one embodiment of the invention, an isolated and purified membrane vesicle of *Shigella flexneri* is provided.

The membrane vesicles are characterized by having specific antigens associated with their surfaces, and containing specific enzymes, which are native to the microorganism from which the membrane vesicles are derived. Table 1 is a list of microbial pathogens and the antigens and enzymes of the pathogens which can be incorporated into membrane vesicles. For example, membrane vesicles which have endotoxin, outer membrane proteins, pilin, and flagellin associated with the membrane vesicle surface, and which contain protease, phospholipase C, proelastase, and autolysins can be obtained from *Pseudomonas aeruginosa,* which is a pathogen associated with corneal infections, nosocomial infections etc.

The antimicrobial membrane vesicles described herein may also contain one or more surface active agents which are used to induce formation of the vesicles. Preferably, the membrane vesicles contain a surface-active anti-microbial agent such as polymyxin, or other surface-active agents such as EDTA. Preferably, the membrane vesicles contain aminoglycosides, preferably gentamicin, hygromycin, tobramycin, amakacin, kanamycin, neomycin, paromomycin, and/or streptomycin.

The microorganisms which produce membrane vesicles described herein may also be transfected with one or more nucleotide sequences encoding exogenous proteins in order to provide membrane vesicles have exogenous proteins incorporated into the membrane vesicles or associated with their surface. For example, the exogenous proteins include antigens which are associated with infectious diseases caused by infectious agents which do not produce membrane vesicles including viruses such as human immunodeficiency virus (HIV), influenza (nuriminidase/haemagglutinin), adenovirus, Herpes simplex, measles, simian immunodeficiency virus; fungi such as *Histoplasma capsulatum, Cryptococcus neoformans, Blastomyces dermatidis, Candida albicans;* protozoa such as *Leishmania mexicana, Plasmodium falciparum* and *Taxoplasma gondii;* and, gram-positive bacteria such as *Streptococcus mutans,* and *S. pneumoniae* (cell wall antigens). Microorganisms transfected with such antigens may be used to produce membrane vesicles which may be used as vaccines against the infectious agent. The microorganism may also be transfected with a nucleotide sequence encoding an exogenous protein having a known therapeutic or regulatory activity such as hormones preferably insulin, blood clotting factor VIII, growth hormones, hirudin, cytokines such as gamma interferon, tumor necrosis factor, IL-1, IL-2,IL-3, IL-4, IL-5, IL-6, IL-7, IL-8, IL-9, IL-10, IL-11, GM-CSF, CSF-1, and G-CSF. Membrane vesicles containing therapeutic or regulatory proteins may be used to deliver the proteins to a host. The microorganisms may also be transfected with proteins which facilitate targeting of a membrane vesicle having the proteins associated with their surfaces to specific target tissues or cells. For example, tumor-associated antigens, $CD_4$ proteins on T-helper cells, and gp120 in HIV.

II. Preparation of Membrane Vesicles

Suitable microorganisms which may be used to prepare membrane vesicles are described above. The strains of the microorganism used to prepare the membrane vesicles may be reference strains which may be obtained from Research Institutes working in the field, or from public depositories such as the American Type Culture Collection, Bethesda, Md. The microorganism strains may also be obtained from animals, preferably humans suffering from naturally occurring infections.

Nucleotide sequences encoding exogenous proteins may be introduced into microorganisms which produce membrane vesicles using methods well known to those skilled in the art. The necessary elements for the transcription and translation of the inserted nucleotide sequences may be selected depending on the host cell chosen, and may be readily accomplished by one of ordinary skill in the art. A reporter gene which facilitates the selection of host cells transformed or transfected with a nucleotide acid sequence may also be incorporated in the microorganism. (See, e.g., Sambrook et al. Molecular Cloning A Laboratory Manual, 2nd edition, Cold Spring Harbor Laboratory Press, 1989, for transfection/transformation methods and selection of transcription and translation elements, and reporter genes). Sequences which encode exogenous proteins may generally be obtained from a variety of sources, including for example, depositories which contain plasmids encoding sequences including the American Type Culture Collection (ATCC, Rockville Md.), and the British Biotechnology Limited (Cowley, Oxford England).

The microorganisms are grown under suitable conditions that permit natural membrane vesicles to be formed. Suitable growth conditions will be selected having regard to the type of microorganism, and the desired characteristics of the membrane vesicles. Generally, growth mediums suitable for culturing the microorganisms so that they produce membrane vesicles contain a nitrogen source and a carbon source.

Suitable nitrogen sources are nitrogen salts. The initial concentration of the nitrogen source is related to the temperature of the fermentation during the growth phase. There should be enough nitrogen source present to provide a final cell mass of a least about 0.5–1.0 g/l. A useful range of initial nitrogen concentration is selected so that less than 0.1 g/l remains at the conclusion of the growth phase.

As carbon source, sugars such as glucose (or crude glucose such as dextrose), sucrose, fructose, erythrose, mannose, xylose, and ribose, or mixtures of these sugars may be used. Commercial sources of these sugars can conveniently be used. Such sources include liquid sucrose, high fructose corn syrup and dextrose corn syrup. Other carbon sources can be used in combination with these sugars such as mannitol and other sugar derivatives.

The medium preferably includes other components useful in fermentation processes. For example, the medium may include a source of magnesium such as magnesium sulfate, a source of phosphate such as $K_2HPO_4$, a source of iron such as iron sulfate, and a source of zinc such as zinc sulfate. Useful concentration ranges of magnesium, phosphate, iron and zinc are 2–5 mM, 0.5–5.0 mM, 2–5 mM, 1–5 mM, 0.5 mM and 0.5–5.0 mM, respectively.

The medium may also contain components which support the production of specific enzymes. For example, choline (2-hydroxy methyl-trimethyl ammonium chloride salt) may be added to the medium to support the production of phospholipase C, or chelating compounds such as transferrin to support siderophore production.

By way of example, *Pseudomonas aeruginosa* may be cultured in a medium containing the following components: 10 mM glucose (or other carbon source); 1.2 mM $K_2HPO_4$, 3.2 mM $MgSO_4.7H_2O$, 12 mM $(NH_4)_2SO_4$, 3 mM NaCl, 3 mM KCl, 3.2 mM $FeSO_4.7H_2O$, and 50 mM of a suitable buffer (e.g. MOPS).

Commercially available media may be used which favour the production of membrane vesicles. For example, Mueller-Hinton broth, or Trypticase soy broth, may be used for culturing *Pseudomonas* species; Brain-Heart Infusion may be used for culturing *E. coli, Pasteurella*, and *Neisseria* species; and, blood agar may be used for culturing *Haemophilus* species.

The microorganisms are cultured in two stages. The first stage is carried out at a temperature sufficient to promote the growth phase of the microorganism. After rollover into the stationary phase, the temperature of the growth medium may be reduced to a temperature which promotes production of membrane vesicles. For example, the temperature may be reduced to 20 to 25° C., preferably room temperature.

The final medium is subjected to a variety of steps to recover the desired membrane vesicles. For example, the membrane vesicles may be isolated by precipitation, filtration, and/or differential centrifugation.

Formation of membrane vesicles may be induced using surface-active agents. The release of membrane vesicles typically increases several fold after the microorganism is exposed to an agent. Suitable surface agents include surface-active antimicrobial agents such as polymyxin, atypical metal ions, and EDTA. Preferably, the surface-active agent is an antimicrobial surface-active agent, most preferably an aminoglycoside. Examples of suitable aminoglycosides include gentamicin, hygromycin, tobramycin, amakacin, kanamycin, neomycin, paromomycin, and streptomycin. The method for inducing formation of the membrane vesicles is generally as described above. The microorganism is cultured using the above described conditions, and the surface-active agent is added after the first stage, i.e., after early stationary growth phase. The concentration of antimicrobial agent that is added is about four times the minimal inhibitory concentration (MIC).

By way of example, *Pseudomonas aeruginosa* can be induced to release membrane vesicles into the medium on exposure of the organism to gentamicin. In particular, *Pseudomonas* strains are grown in Mueller-Hinton broth to the early stationary phase ($10^6$ CFU/ml) at 37° C. Gentamicin at a final concentration of four times the MIC is then added to the bacterial culture in early stationary phase and the culture is incubated at room temperature for about 30 minutes. The cells are removed from the suspension by centrifugation at 4000 to 8000×g for 0.5 to 1 hour, and the supernatant is filtered, preferably through cellulose acetate filters, to remove residual cells. Membrane vesicles are recovered from the filtrates by centrifugation at 100,000 to 170,000×g for 1 to 3 hours. The membrane vesicles are suspended in a suitable buffer, for example HEPES buffer, preferably at a pH of between about 6.8 and 7.4.

The antigens associated with the surface of membrane vesicles may be identified using conventional methods. For example, Western immunoblots of solubilized components of the membrane vesicles can be prepared and specific antigens can be identified using antibodies specific for the antigen (e.g., antibodies specific for LPS, pilin, flagellin etc.). LPS can also be identified using immunogold electron microscopic detection.

Enzymes contained in the membrane vesicles may be identified using conventional enzyme assays. For example, phospholipase C activity may be determined using the synthetic substrate p-nitrophenyl phosphorylcholine (Sigma) as described by Berka et al. (Infect. Immun. 34:1071–1074, 1981); protease may be determined by the assay described by Howe and Iglewski (Infect. Immun. 43:1058–1063, 1984) using Hide powder azure (Sigma); alkaline phosphatase may be assayed using p-nitrophenyl phosphate (pNPP) (Sigma) as described in Tan, A. S. P. and E. A. Worobec (FEMS Microbial. Letts. 106:281–286, 1993); elastase may be determined using elastin Congo red (Sigma) as a substrate in an assay based on the method of Kessler and Safrin (Kessler, E., and M. Safrin, J. Bacteriol. 170:5241–5247, 1988); and hemolysin activity may be measured as described in Bergmann et al. (Infect. Immun. 57:2187–2195, 1989). Peptidoglycan hydrolases may be determined using SDS-PAGE zymogram systems as outlined in Bernadsky, G., et al. (J. Bacteriol. 176:5225–5232, 1994). Immunogold electron microscopic detection may also be used to identify enzymes contained in a membrane vesicle.

III. Vaccines

As hereinbefore mentioned, the present invention relates to a vaccine against an infectious disease caused by an infectious agent comprising a carrier strain having a membrane vesicle of a microorganism integrated into the cell surface of the carrier strain, wherein the membrane vesicle has an amount of an antigen associated with its surface which is effective to provide protection against the infectious agent. The term "integrating" or "integrated" used herein refers to the fusion of the cell membrane of the membrane vesicle with the cell surface of the carrier strain, or the adherence of the membrane vesicle to the cell surface of the carrier strain.

"Infectious disease" refers to any disease or condition due to the action of an infectious agent. The infectious agent may be a microorganism which produces membrane vesicles, or a microorganism which does not produce membrane vesicle. In the former embodiment, the membrane vesicle used in the vaccine is obtained from a microorganism which produces membrane vesicles with one or more antigens associated with the surface of the vesicle.

Therefore, in an embodiment of the invention, a vaccine against infectious diseases caused by a microorganism which produces membrane vesicles is provided which comprises a carrier strain having a membrane vesicle of the microorganism integrated into the cell surface of the carrier strain. The vaccines may be used for the prophylaxis or active immunization and treatment of infectious diseases caused by microorganisms which produce natural membrane vesicles and/or which can be induced to produce membrane vesicles for example using surface-active agents. Examples of pathogenic microorganisms which produce membrane vesicles are listed in Table 1.

In accordance with another embodiment of the invention, a vaccine against infectious diseases caused by an infectious agent which does not produce membrane vesicles is provided which comprises a carrier strain having a membrane vesicle from a microorganism integrated into the cell surface of the carrier strain, wherein the membrane vesicle has an amount of an antigen associated with its surface which is effective to provide protection against the infectious agent. The vaccines may be used for the prophylaxis or active immunization and treatment of infectious diseases caused by microorganisms including viruses such as human immunodeficiency virus (HIV), influenza (nuriminidase/haemagglutinin), adenovirus, Herpes simplex, measles, simian immunodeficiency virus; fungi such as *Histoplasma capsulatum, Cryptococcus neoformans, Blastomyces dermatidis, Candida albicans;* protozoa such as *Leishmania mexicana, Plasmodium falciparum* and *Taxoplasma gondii;* and, gram-positive bacteria such as *Streptococcus mutans,* and *S. pneumoniae.* Therefore, the vaccines of the present invention may incorporate membrane vesicles with immunogenic antigens of these microorganisms.

The membrane vesicles employed in the vaccines of the present invention may be natural membrane vesicles of the microorganism or they may be membrane vesicles produced by treating the microorganism with a surface-active agent as described hereinbefore. The membrane vesicles are selected so that they have an amount of an antigen (i.e. immunogen) associated with their surfaces which is effective to provide protection against the pathogenic infectious agent/microorganism. For example, for the pathogens listed in Table 1, membrane vesicles may be selected which contain the specific antigens identified in Table 1. In particular, membrane vesicles may be selected for *Pseudomonas aeruginosa* which have endotoxin (A- and B-band lipopolysaccharide), outer membrane proteins, pilin, and/or flagellin associated with their surfaces. These membrane vesicles may be fused with a carrier strain to provide a vaccine which is useful for protecting against infections caused by *Pseudomonas aeruginosa.*

The carrier strain is selected so that it is incapable of multiplying in vivo. Carrier strains are obtained through selection of variants which occur naturally, or using conventional means known to those skilled in the art. Examples of suitable carrier strains are *Shigella* species, *Salmonella* species, preferably *S. typhi* Ty21a, *S. typhimurium, Vibrio* species, and *Escherichia* species.

The invention also relates to a method of preparing a vaccine against an infectious disease caused by an infectious agent comprising integrating a membrane vesicle of a microorganism into the cell surface of a carrier strain wherein the membrane vesicle has an amount of an antigen associated with its surface which is effective to provide protection against the infectious agent. In an embodiment, the invention provides a method of preparing a vaccine against infectious diseases caused by a microorganism which produces membrane vesicles which comprises integrating a membrane vesicle produced by the microorganism into the cell surface of a carrier strain.

A membrane vesicle may be integrated into the cell surface of a carrier strain by contacting the membrane vesicle with the carrier strain. By way of example, exponential growth phase cultures of the carrier strain (e.g., *S. typhimurium aro* A, and *S. typhi*Ty21a) in a suspension of $10^4$ to $10^9$ CFU/ml, preferably $10^6$ CFU/ml, are incubated with membrane vesicles (100 μg/ml of protein) from, for example *P. aeruginosa* or *Shigella flexneri.*

The vaccine may be a multivalent vaccine and additionally contain immunogens related to other infectious diseases in a prophylactically or therapeutically effective manner. Multivalent vaccines against infectious diseases caused by different infectious agents may contain a carrier strain having membrane vesicles integrated into the cell surface of the carrier strain, wherein the membrane vesicles have amounts of antigens associated with their surfaces which are effective to provide protection against the infectious agents.

A multivalent vaccine may comprise at least two carrier strains each having membrane vesicles with different immunogens associated with different infectious agents. In an embodiment of the invention a multivalent vaccine is provided comprising at least two carrier strains each having membrane vesicles of different pathogenic microorganisms integrated into the cell surface of the carrier strain For example, a multivalent vaccine may contain a carrier strain having a selected membrane vesicle of *P. aeruginosa* integrated into its cell surface, and a carrier strain having a selected membrane vesicle of *S. flexneri* integrated into its cell surface.

A multivalent vaccine may contain a carrier strain having at least two membrane vesicles having different immunogens associated with different infectious agents. In an embodiment of the invention, a multivalent vaccine is provided comprising a carrier strain and membrane vesicles from at least two different microorganisms integrated into the cell surface of the carrier strain. Thus, a carrier strain may contain immunogens relating to more than one pathogenic microorganism. For example, a carrier strain may be contacted with a selected membrane vesicle obtained from *P. aeruginosa*, and a membrane vesicle obtained from *S. flexneri* using the methods described herein, to produce a carrier strain having immunogens from both bacteria associated with the cell surface.

Multivalent vaccines are prepared by integrating membrane vesicles into the cell surface of one or more carrier strains as described herein.

The vaccine of the invention contains an immunologically effective amount of the carrier strain(s) with the integrated membrane vesicle(s), for example between $1\times10^9$ to $5\times10^{10}$ cells per dosage unit, preferably $5\times10^9$ to $2\times10^{10}$ cells per dosage unit. The optimum amounts of cells depends on the nature of the infection against which protection is required, the characteristics of the animals to be protected, and other factors known to persons skilled in the art.

In addition to the carrier strain(s) with the integrated membrane vesicle(s), the vaccine may comprise an immunologically acceptable carrier such as aqueous diluents, suspending aids, buffers, excipients, and one or more adjuvants known in the art. Suitable adjuvants include aluminum hydroxide, Freund's adjuvant (complete or incomplete), bacteria such as *Bordetella pertussis* or *E coli* or bacterium derived matter, immune stimulating complex (iscom), oil, sapronin, oligopeptide, emulsified paraffin-Emulsigen™ (MVP Labs, Ralston, Nebr.), L80 adjuvant containing $AL(OH)_3$ (Reheis), Quil A (Superphos), or other adjuvants known to the skilled artisan. The vaccine may also contain preservatives such as sodium azide, thimersol, beta propiolactone, and binary ethyleneimine.

The vaccines of the invention can be intended for administration to animals, including mammals, avian species, and fish; preferably humans and various other mammals, including bovines, equines, and swine.

The vaccines of the invention may be administered in a convenient manner, such as intravenously, intramuscularly, subcutaneously, intraperitoneally, intranasally or orally. Preferably the vaccine is administered orally, intramuscularly or subcutaneously. The dosage will depend on the nature of the infection, on the desired effect and on the chosen route of administration, and other factors known to persons skilled in the art.

A vaccine prepared using the methods described herein may be tested in in vivo animal systems to confirm their efficacy in the prophylaxis or active immunization and treatment of infectious diseases and to determine appropriate dosages and routes of administration.

The membrane vesicles of the invention are also useful for preparing antibodies which may be used as a means of passive immunization. Within the context of the present invention, antibodies are understood to include monoclonal antibodies, polyclonal antibodies, antibody fragments (e.g., Fab, and $F(ab')_2$ and recombinantly produced binding partners. Polyclonal antibodies may be readily generated by one of ordinary skill in the art from a variety of warm-blooded animals such as horses, cows, various fowl, rabbits, mice, or rats. Monoclonal antibodies may also be readily generated using conventional techniques (see U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, William D. Huse et al., "Generation of a Large Combinational Library of the Immunoglobulin Repertoire in Phage Lambda," Science 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," Proc Natl. Acad. Sci USA 86:5728–5732, August 1989; see also Michelle Alting-Mees et al., "Monoclonal Antibody Expression Libraries: A Rapid Alternative to Hybridomas," Strategies in Molecular Biology 3:1–9, January 1990; all of which are incorporated herein by reference). Similarly, binding partners may also be constructed utilizing recombinant DNA techniques.

The membrane vesicles of the present invention additionally are useful for screening for immunogenic antigens of a pathogen which may be used in conventional vaccines or incorporated in a membrane vesicle vaccine as described herein. For example a putative immunogenic antigen of a pathogen may be associated with the surface of the membrane vesicle using the methods described herein. The immunogenicity of the antigen may be determined by vaccinating an animal with the membrane vesicle with the associated antigen, and later challenging the animal with the pathogen to determine the protective effect of the antigen. An antigen showing a protective effect in such a system can be used in conventional vaccines (e.g. by itself or expressed on a carrier strain), or the membrane vesicle with the associated antigen can be used as a vaccine.

III. Use of the Vesicles as Bacteriolytic Agents

As hereinbefore mentioned the present invention also contemplates a pharmaceutical composition comprising a membrane vesicle of a microorganism containing one or more enzymes with peptidoglycan hydrolase, lipase, or proteolytic activity in an amount effective to have a bactericidal effect on gram-negative and/or gram-positive bacterial pathogens, and a pharmaceutically acceptable vehicle or diluent. The membrane vesicle may be a natural membrane vesicle of a microorganism, or it may be produced by treating the microorganism with a surface-active agent as described herein (i.e. large membrane vesicle). Compositions containing the large membrane vesicles therefore may also contain a surface active agent such as an antibiotic.

The invention also contemplates a method of treating an infectious disease caused by a gram-negative and/or gram-positive bacterial pathogen comprising administering an amount of a membrane vesicle containing one or more enzymes with peptidoglycan hydrolase, lipase, or proteolytic activity, effective to have a bactericidal effect on the gram-negative and/or gram-positive bacterial pathogen.

Membrane vesicles for use in these pharmaceutical compositions and methods, may be prepared using the methods described herein. In particular, membrane vesicles containing enzymes with peptidoglycan hydrolase, lipase, and proteolytic activity may be selected using conventional enzyme assays.

Membrane vesicles containing bacteriolytic enzymes and therapeutic agents such as antibiotics i.e. larger membrane vesicles produced after treatment with a surface-active agent as described herein, are particularly useful in the pharmaceutical compositions and methods of the present invention. The therapeutic agent and hydrolytic enzymes in the membrane vesicle act synergistically to provide an enhanced bactericidal effect.

The compositions of the invention are administered to subjects in a biologically compatible form suitable for pharmaceutical administration in vivo. By "biologically compatible form suitable for administration in vivo" is meant a form of the composition to be administered in which any toxic effects are outweighed by the therapeutic effects of the membrane vesicles.

The composition may be administered in a convenient manner such as by injection (subcutaneous, intravenous, etc.), oral administration inhalation, transdermal application, or rectal administration. The pharmaceutical compositions are therefore in solid or semisolid form, for example pills, tablets, creams, gelatin capsules, capsules, suppositories, soft gelatin capsules, gels, membranes, tubelets. For parenteral and intracerebral uses, those forms for intramuscular or subcutaneous administration can be used, or forms for infusion or intravenous or intracerebral injection can be used, and can therefore be prepared as solutions of the active membrane vesicles or as powders of the vesicles to be mixed with one or more pharmaceutically acceptable excipients or diluents, suitable for the aforesaid uses and with an osmolarity which is compatible with the physiological fluids. For local use, those preparations in the form of creams or ointments for topical use, or in the form of sprays should be considered; for inhalant uses, preparations in the form of sprays, for example nose sprays, should be considered.

The preparations of the invention can be intended for administration to animals, preferably humans and other warm blooded animals.

Administration of an amount effective to have a bactericidal effect is defined as an amount effective, at dosages and for periods of time necessary to achieve the desired result. For example, an amount effective to have a bactericidal effect may vary according to factors such as the disease state, age, sex, and weight of the individual. Dosage regimes may be adjusted to provide the optimum therapeutic response. Amounts of membrane vesicles effective to have a bactericidal effect on a selected gram-negative and/or gram-positive bacterial pathogen may be determined using conventional in vivo and in vitro tests (see zymogram systems as outlined in Bernadsky, G. et al. supra).

The pharmaceutical compositions can be prepared by per se known methods for the preparation of pharmaceutically acceptable compositions which can be administered to patients, and such that an effective quantity of the active vesicles are combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the pharmaceutical compositions include, albeit not exclusively, solutions of the membrane vesicles in association with one or more pharmaceutically acceptable vehicles or diluents, and contained in buffered solutions with a suitable pH and iso-osmotic with the physiological fluids.

The pharmaceutical compositions containing membrane vesicles of a microorganism containing one or more enzymes with peptidoglycan hydrolase, lipase, or proteolytic activity, and optionally a therapeutic agent, and methods of treatment using these compositions, may be used for the prophylaxis and treatment of conditions associated with various gram-negative and gram-positive bacterial pathogens. For example, the compositions and methods are useful in the treatment of conditions associated with the following pathogens:

A. Gram-positive Pathogens

Staphylococcus aureus (boils, abscesses, "staph" pneumonia, blood-poisoning, meningitis, osteomyelitis, food-poisoning, wound infections, endocarditis, meningitis, enteritis, and nephritis);

S. epidermidis (usually less invasive than S. aureus);

Streptococcus pyogenes ("flesh-eating bacterium", blood poisoning, scarlet fever, strept throat, endocarditis);

Bacillus subtilis

S. pneumoniae (pneumonia);

S. mutans (caries);

S. sanguis (endocarditis);

S. faecalis (gastroenteritis).

Corynebacterium diphtheriae (diphtheriae);

Bacillus anthracis (anthrax);

Actinomyces spp. (actinomycosis);

A. israelis ("lumpy jaw" in humans, periodontal disease) and A. bovis (same in cattle);

B. cereus (diarrhea);

Clostridium spp. (gas gangrene),

C. difficile (colitis),

C. perfringes (diarrhea).

Mycobacterium spp.

M. leprae (leprosy),

M. tuberculosis (TB; there are so-called "super antibiotic resistant strains" emerging), M. paratuberculosis (a human and bovine pathogen), M. bovis (cattle), M. avium-intracellulase (Lymphadenopathy and disseminated TB).

Listeria monocytogenes (monocytosis, meningitis)

Nocardia spp. (noocardiosis)

Both Streptococcus and Staphylococcus can also cause the following post-infection diseases: glomerulonephritis (Bright's Disease); immune mediated rheumatic fever (Streptococcus), and toxic shock syndrome, caused by a secreted toxin (Staphylococcus). It should be noted that Streptococcus and Staphylococcus infections can be serious because many strains have multiple antibiotic resistances.

B. Gram-negative Pathogens

E. coli

Proteus vulgaris

Serratia marscens

Klebsiella pneumoniae

Pseudomonas aeruginosa

The pathogens listed in Table 1.

The pharmaceutical compositions and methods of treatment are also useful in the prophylaxis and treatment of infectious diseases associated with drug resistant pathogens. For example, compositions and methods of the invention containing membrane vesicles produced by treatment with gentamicin can be used for the prophylaxis and treatment of conditions associated with gentamicin resistant bacteria.

The pharmaceutical compositions may also be applied to implants such as catheters, pace-makers, etc. which are often sites for colonization of pathogens, and thus sources of infectious diseases.

IV. Drug Delivery Systems

The present invention also relates to a composition comprising membrane vesicles of a microorganism containing a therapeutic agent in an amount which is effective to introduce the therapeutic agent into a host. The invention also relates to a method for administering a therapeutic agent to a host comprising administering to the host a suspension of the therapeutic agent encapsulated in a membrane vesicle of a microorganism.

Therapeutic agents may be encapsulated in membrane vesicles by culturing the microorganisms capable of producing membrane vesicles in the presence of the therapeutic agents. The therapeutic agents may also be produced by the microorganism by transforming the microorganism with a gene which expresses the therapeutic agent preferably in the periplasmic space.

Any of a wide variety of therapeutic agents may be encapsulated in the membrane vesicles described herein. Among these may be mentioned antimicrobial agents, metabolic regulators, immune modulators, antiproliferative agents, chemotherapeutics, etc. For example, the invention is well suited for antimicrobial agents, such as polymyxin, and aminoglycosides including gentamicin, hygromycin, tobramycin, amakacin, kanamycin, neomycin, paromomycin, streptomycin; and antiviral agents such as interferon, interleukins, and octreotide.

The membrane vesicles may also have carbohydrate, proteins, glycoproteins or glycolipids associated with their surfaces which will target the therapeutic agent to the tissue where it is most needed. Alternatively, specific adhesins such as bacterial fimbriae can be incorporated in the surface of the membrane vesicles. This will enable targeting to only the tissues at risk while reducing the exposure of other tissues to toxic side effects of the drug. Slow sustained release of therapeutic agents from vesicles will also prolong the residence time of the therapeutic agent in areas where it is most needed.

In one embodiment of the invention, a composition is provided comprising membrane vesicles of a microorganism containing an antimicrobial agent, in an amount which is effective to introduce the antimicrobial agent into a host. The invention also relates to a method for administering an antimicrobial agent into a host comprising administering to the host a membrane vesicle of a microorganism containing the antimicrobial agent. Membrane vesicles containing antimicrobial agents for use in these compositions and methods may be prepared using the methods described herein. For example, membrane vesicles containing antimicrobial agents may be prepared by exposing a microorganism which is capable of producing membrane vesicles (for example the microorganisms listed in Table 1, preferably *P. aeruginosa* or *Shigella flexneri*) to an antimicrobial agent. Preferably the antimicrobial agent is polymyxin, or an aminoglycoside such as gentamicin, hygromycin, tobramycin, amakacin, kanamycin, neomycin, paromomycin, and streptomycin.

V. Method of Inserting Nucleic Acids into Cells

The invention also relates to a method of inserting nucleic acid molecules into a target cell which comprises encapsulating the nucleic acid in a membrane vesicle of a microorganism, and bringing the membrane vesicle in contact with the target cell whereby the nucleic acid molecule is inserted into the cell. Nucleic acid molecules which may be encapsulated in a membrane vesicle may be from eucaryotic or prokaryotic cells and they may be endogenous or exogenous to a microorganism that produces membrane vesicles. Examples of nucleic acid molecules which may be encapsulated in a membrane vesicle are nucleic acid molecules encoding (a) mammalian proteins such as hormones preferably insulin, blood clotting factor VIII, growth hormones, hirudin, cytokines, and a normal copy of the cystic fibrosis transmembrane conductance regulator (CFTR); (b) viral antigens such as HIV glycoprotein, hepatitis B surface antigens, influenza antigens; fungal antigens for example from *Histoplasma capsulatum, Cryptococcus neoformans, Blastomyces dermatidis, Candida albicans;*, and (c) protozoal antigens for example from *Leishmania mexicana, Plasmodium falciparum* and *Taxoplasma gondii*.

"Target cells" as used herein refers to a cell of a living organism, plant, animal, or microbe. The cell may be unicellular such as a microorganism or it may be multicellular including animals such as humans.

Membrane vesicles containing nucleic acid molecules may be prepared by the methods described herein preferably using surface-active agents. For example, treatment of a microorganism which produces membrane vesicles (which has or has not been transfected with an exogenous nucleic acid molecule), with a surface-active agent such as gentamicin will produce membrane vesicles incorporating DNA.

The encapsulated nucleic acid molecule is inserted into a target cell by contacting the membrane vesicle containing the nucleic acid molecule with the surface of the target cell. For microorganisms the contact is with the cell wall, and for animal cells it is with the membrane. Cells associated with multi-cellular organisms may be contacted in vivo or in vitro. The nucleic acid molecule passes into the target cells when the membrane vesicle contacts the target cell, and it is taken up by the target cell through fusion of the membrane vesicle with the cell wall or membrane, or by endocytosis. Conventional techniques are used to contact the membrane vesicles with the target cells. For example, if the contact is to be effected in vitro, the cells and membrane vesicles are admixed. In vivo the membrane vesicles may be injected intravenously or given orally into the host organism in combination with a pharmaceutically acceptable carrier.

It will also be appreciated that the membrane vesicles described herein may be used to isolate products produced by genetic engineering techniques. For example, a host microorganism which produces membrane vesicles may be transformed with a recombinant vector having a gene encoding a desired gene product and having the necessary transcription and translation elements required for the gene product to be expressed in the host cell, and preferably transported to the periplasmic space. The microorganism expressing the gene product may be cultured under suitable conditions to produce natural membrane vesicles, or the microorganism may be induced to produce membrane vesicles after exposure to a surface-active agent. Membrane vesicles containing the gene product may be isolated and the gene product can be removed from the membrane vesicles. Products (e.g. cell surface antigens and enzymes) which are endogenous to a microorganism which produces membrane vesicles may also be isolated from membrane vesicles in a similar fashion.

The following non-limiting examples are illustrative of the present invention:

EXAMPLES

Example 1

Preparation and Characterization of the Membrane Vesicles (MVs)

The following materials and methods were utilized in the investigations outlined in Example 1:

Bacterial strains and growth conditions. *P. aeruginosa* strain H103 and ATCC 19660 were grown in Mueller-Hinton broth (MHB) to the early stationary growth phase (ca. $10^8$ CFU/ml) on an orbital shaker at 37° C. with an agitation rate of 125 rpm. To support the production of PLC, 0.2% (w/v) choline (the [2-hydroxy methyl] tri-methyl ammonium chloride salt; Sigma Chemical Co., St. Louis, Mo.) was added to the culture medium (Shortage V. D. et al., Mol. Microbiol. 6:863–871, 1992). Strain ATCC 19660 was used to detect elastase and protease activity, as the amounts produced by this strain was found to be higher than H 103 under the culture conditions used in the study.

Antibiotic susceptibility test. The Minimum Inhibitory Concentrations (MICs) of gentamicin were determined by dilution in MHB. The MICs for strains H 103 and ATCC 19660 were 2 and 2.5 $\mu$g/ml, respectively.

Isolation and quantification of MVs. One liter of bacterial culture in early stationary growth phase was divided into two equal parts. To one, gentamicin at a final concentration of 4×MIC was added, whereas the other served as control. Both cultures were incubated for 30 min. on an orbital shaker at room temperature. Cells were removed from the suspension by centrifugation at 6000×g. The supernatants were filtered sequentially through 0.45 and 0.22 μm pore-size cellulose acetate membranes (MSI, Westboro, Mass.) to remove residual cells. MVs were recovered from the resulting filtrates by centrifugation at 150,000×g for 3 h at 5° C. in a 45 Ti rotor (Beckman, Instruments, Inc. Toronto, Canada) and the vesicle mass was measured after the supernatant was carefully aspirated from pre-weighed ultracentrifuge tubes. The vesicle pellet was washed once with 50 mM N-2-hydroxyethylpiperazine-N'-2-ethanesulfonic acid (HEPES) buffer (pH 6.8) (Research Organics Inc., Cleveland, Ohio), pelleted by centrifugation at 120,000×g for 30 min and resuspended in 50 mM HEPES buffer (pH 6.8) containing 0.5 mM dithiothreitol (DTT) (Sigma) as a protective agent for —SH groups. For some experiments, MVs were resuspended in HEPES buffer without DDT.

Electrophoresis. Outer membrane proteins (OMPs) were prepared with sodium N-lauroyl sarcosinate (Sarkosyl; Sigma) as described in Brown M. R. W. et al (FEMS Microbiol. Lett. 21:113–117, 1984). Washed whole cells and MVs were solubilized in sample buffer (0.5 M Tris hydrochloride pH 6.8, 3% sodium dodecyl sulfate (SDS), 20% glycerol, 1% 2-mercaptoethanol and 0.002% bromophenol blue) and heated to 100° C. for 10 min. A 25 μg sample of protein was analysed by SDS-polyacrylamide gel electrophoresis (SDS-PAGE) with 12% acrylamide gels and the polypeptides were stained with Coomassie blue as described in Brown M. R. W. et al (FEMS Microbiol. Lett. 21:113–117, 1984). A 40 μg sample of protein from whole cells and MVs was digested with protenase K (100 μg/ml) (Sigma) and analysed for lipopolysaccharide (LPS) as described previously (Kadurugamuwa, J. L., et al Antimicrob. Agents Chemother. 37:715–721, 1993; and Lightfoot, J. et al., J. Bacteriol. 173:5264–5630).

Zymography. Proteinases were resolved by SDS-PAGE using the method of Matsumoto et. al.(Invest. Opthalmol. Vis. Sci. 34:1945–1953, 1993) with slight modifications. The separating gels used were 8% SDS gels containing α-casin or gelatin (Type A from bovine skin; Sigma) at a final concentration of 0.15%. The stacking gels consisted of 4% SDS gels without gelatin or casein. A 25 μg protein sample from each preparation (without reducing agents) was loaded onto gels and was run at 4° C. for 90 min. at 120 V. After electrophoresis, the gels were shaken at room temperature in a solution of 2.5% Triton-X100 for 45 min. to remove the SDS. Subsequently, the gels were incubated at 37° C. in incubation buffer (50 mM Tris-HCl, pH 8.0, 5 mM $CaCl_2$) with 5 mM EDTA for 18 h. The positions of the proteinases were identified after the gels were stained (0.5% Comassie brilliant blue R-250, 10% acetic acid, 40% methanol) for 2 h and clear bands were identified.

Western immunobloting. LPS samples were transferred from the SDS-PAGE gel to nitrocellulose and reacted with monoclonal antibodies (MAbs) specific for B-band serotype 05 or A-band polysaccharide as described previously ((Kadurugamuwa, J. L., et al Antimicrob. Agents Chemother. 37:715–721, 1993; and Lightfoot, J. et al., J. Bacteriol. 173:5264–5630). Alkaline phosphatase was detected by the method of Tan and Worobec (FEMS Microbial Letts. 106:281–286). Elastase and alkaline protease were detected with mouse polyclonal antiserum to the purified enzymes which were supplied by R. Birk, Wayne State University. Purified *P. aeruginosa* elastase was from Nagase Biochemicals, Tokyo, Japan.

Fluorometric quantification of DNA. The DNA content in MVs was quantitated using an assay developed by the Pierce Chem. Co. (Pierce, Rockford, Ill.) according to the manufacturer's instructions. Briefly, 20 μg of protein from MVs in 50 μl assay buffer (0.1 M NaCl, 10 mM EDTA, 10 mM Tris, pH 7.0) was lysed with 50 μl of extraction solution (0.1 M $NH_4OH$, 0.2% Triton X-100). A standard curve for DNA was prepared with calf thymus DNA (0–150 ng/ml) (provided with the assay kit) in 200 mM NaCl, 20 mM EDTA, pH 7.0, 0.05 $NH_4OH$, 0.01% Triton X-100). To each sample, 1.5 ml of fluorescent dye (200 μg/ml) (Bisbenzimidazole) was added, the tubes were capped quickly, mixed and fluorescence was measured in a Hitachi F-2000 fluorescence spectrophotometer with excitation and emission wave lengths set at 350 and 455 nm, respectively (10-nm slit width), and yielded values for total DNA/mg of protein. Experiments were also performed on MVs without their being treated with extraction solution. For some experiments, the intact MVs and purified DNA were treated with pancreatic DNase 1 (1.0 μg/ml; Sigma).

Preparation of Cell Lysates, Supernatants and MVs for Enzyme Assays

Membrane-filtered supernatants, before and after harvesting MVs, were concentrated 10-fold in a Concentrator evaporator (Jouan, Winchester, Va.). Washed whole cells or MVs, were sonicated for 2 min. with 0.1% v/v toluene to release intracellular enzymes in a sonic bath (Bransonic Ultrasonic Corporation, Ianburg, Conn.). Protein concentrations of samples were determined with the micro BCA reagent kit (Pierce). Whole cells and MVs (both at a 20 μg protein concentration) or concentrated supernatants (50 μl) were assayed for enzyme activity.

Enzyme assays. PLC activity was determined by the synthetic substrate, p-nitrophenyl 2 phosphorylcholine (NPPC) (Sigma), as described by Berka et al. (Infect. Immun. 34:1071–1074, 1981). Protease was determined by the sensitive assay described by Howe and Iglewski (Infect. Immun. 43:1058–1063, 1984) using Hide powder azure (Sigma) and alkaline phosphatase was assayed using p-nitrophenyl phosphate (pNPP) (Sigma), as previously described (Tan, A. S. P. and E. A. Worobec, FEMS Microbial. Letts. 106:281–286, 1993). Elastase activity was estimated using elastin Congo red (Sigma) as a substrate in an assay based on the method of Kessler et al. (Kessler, E., and M. Safrin, J. Bacteriol. 170:5241–5247, 1988). Haemolysin activity was carried out as described by Bergmann et al. (Infect. Immun. 57:2187–2195, 1989). Each sample was assayed using three replicates. The means and standard errors were calculated using at least three separate experiments.

Transmission electron microscopy (TEM). (i) Negative stains. A 20 μl volume of purified MVs was placed on carbon- and Formvar-coated nickel grids, which were then stained with 2% aqueous uranyl acetate, rinsed and examined with a Philips EM300 transmission electron microscope operating under standard conditions at 60 kV with the cold trap in place. (ii) Immunolabelling of thin sections. *P. aeruginosa* cells or purified MVs were enrobed in 2% molten Noble agar, put through a mild fixation-LR white embedding regimen, and indirectly labelled with protein A gold or anti-mouse immunoglobulin M-gold (EY Laboratories) as outlined in Beveridge et al. (Electron Microscopy, p.42–71., In P. Gerhardt et al. (ed), Methods for general and molecular bacteriology, American Society for Microbiology. Washington, D.C., 1994) using polyclonal antibodies or monoclonal antibodies.

Experimental Results

TEM Microscopy

FIG. 1 shows thin sections of H 103 cells showing the formation of vesicles (solid arrowheads) and free MVs in growth medium (open arrow); (A), Control and (B), exposed to 4×MIC of gentamicin. A larger number of MVs are formed from the cell surface of bacteria exposed to gentamicin than from unreacted cells. Electron dense material has been trapped in the developing and free vesicles.

Bar=100 nm.

Figure 2:
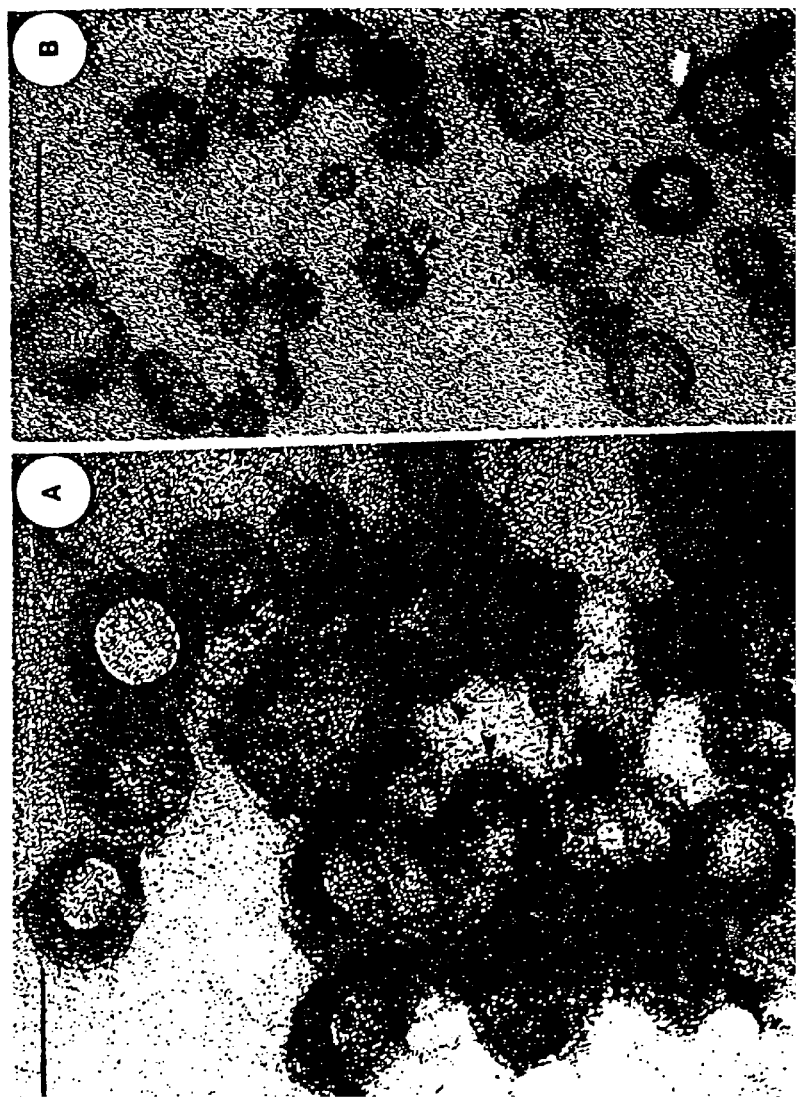
FIG. 2 is an electron micrograph showing a negative stain (A) and a thin section (B) of intact gentamicin membrane vesicles.

FIG. 1 shows thin-sections of P. aeruginosa either treated with gentamicin or untreated. The untreated control cells (FIG. 1(A)) represent "natural" cultured cells and possessed intact cell envelopes, with several membrane blebs emanating from each cell surface or free in the environment. Cells that were exposed to gentamicin formed many more blebs (FIG. 1(B)) than those seen in untreated cells. At a gentamicin concentration of 8 µg/ml, this increase in blebbing was visible after approximately 1 min of antibiotic incubation. Examination of intact isolated purified blebs from both natural and gentamicin-treated cultures in negative stains showed that, although they were partially collapsed, many were filled with a particulate substance (FIG. 2(A) is an electron micrograph showing a negative stain of intact gentamicin-MVs (g-MVs)). This was better shown and confirmed with thin sections (FIG. 2(B) shows an electron micrograph of a thin section of intact g-MVs). The diameter of the vesicles from both untreated and gentamicin-treated cells varied between 50 nm to 150 nm when measured in thin sections; however, when measurements of g-MVs were averaged, the g-MVs were found to be slightly larger than natural MVs (n-MVs), with a mean diameter of 100 nm as opposed to 80 nm for n-MVs. Thin sections proved the vesicles to have a bilayer structure (FIG. 2(B)). No external material was seen by any TEM technique, thereby suggesting the isolated vesicles were free from particulate cellular debris.

Mass Differences Between Total n- and g-MVs

A three-fold increase in vesicle mass was seen from bacteria exposed to gentamicin (36.5±2.6 µg vesicles [mean+standard deviation] per mg bacteria) in comparison with the untreated control cells (11.8+1.8 µg of vesicles per mg bacteria). This indicated that the antibiotic caused the release of more vesicles, presumably due to an ionic interaction between the antibiotic and the cell envelope, and confirmed the outer membrane destabilization demonstrated previously (Kadurugamuwa, J. L., et al Antimicrob. Agents Chemother. 37:715–721, 1993; and Martin, N. L. and T. J. Beveridge, Antimicrob. Agents Chemother. 29:1079–1087, 1986). This increased mass of vesicles was in agreement with their increased frequency as seen by TEM (cf. FIG. 1A and B).

SDS-PAGE Analysis of MVs

Figure 3:
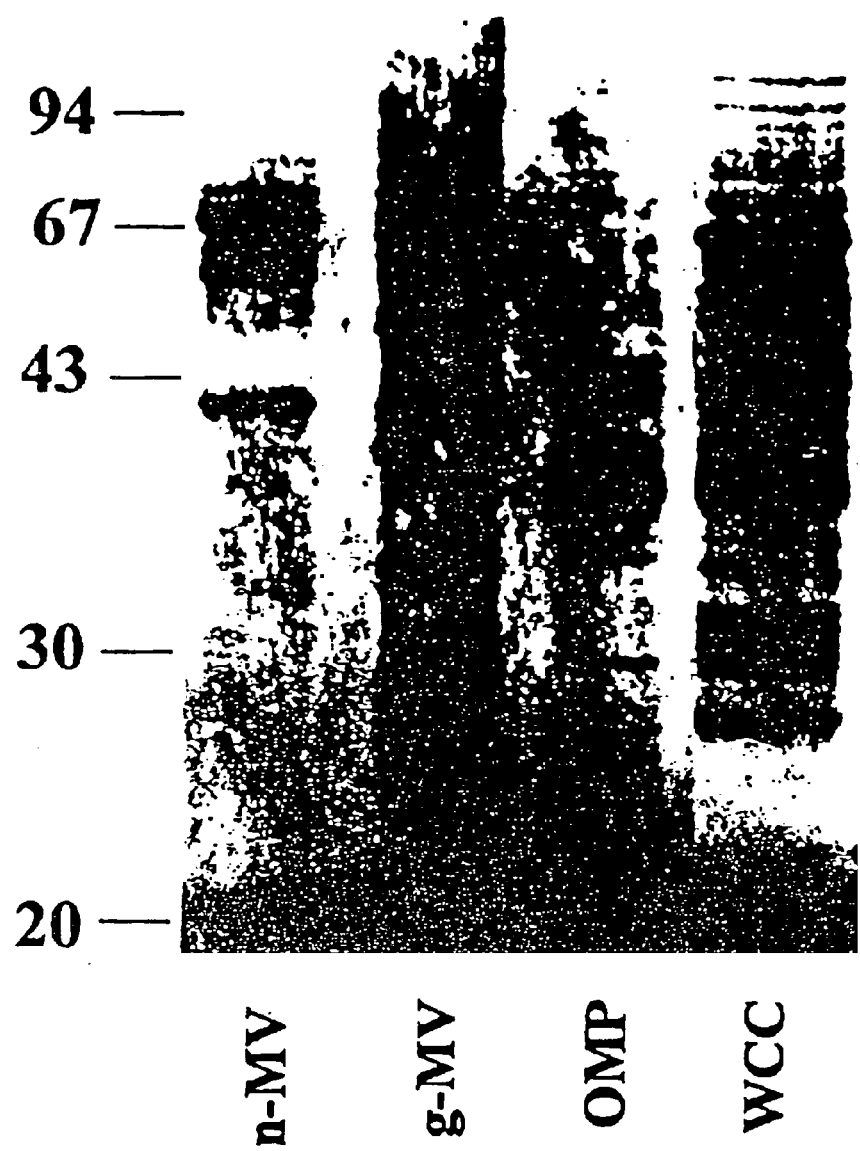
FIG. 3 is an SDS-PAGE profile of natural membrane vesicles, gentamicin membrane vesicles, outer membrane proteins and whole cells.

The protein profiles of whole cell lysates, OMPs extracted from whole cells and MVs from untreated or treated cells were compared by SDS-PAGE. FIG. 3 shows SDS-PAGE profiles of n-MV, g-MV, outer membrane proteins (OMP), and control whole cells (WCC) in a 12% polyacrylamide gel stained with Comassie brilliant blue. Each lane contains 25 µg of total protein from the indicated samples. Molecular masses (in kilodaltons) are indicated on the left.

The n-MVs and g-MVs contained much fewer protein bands than the OMPs extracted from whole cells or whole cell lysates. The banding patterns of n-MVs and g-MVs were very similar, but not identical; both types of MVs appeared to have lost several bands which were normally present in whole cell lysates and the OMP samples. Some of the prominently stained bands from both vesicle preparations included ~70 kD, 40 kD and 20 kD proteins. Trace amounts of an ~35 kD protein was detected in g-MVs but not in n-MVs.

SDS-PAGE Banding Pattern and Immunoreactivities of LPSs from MVs

Figure 4:
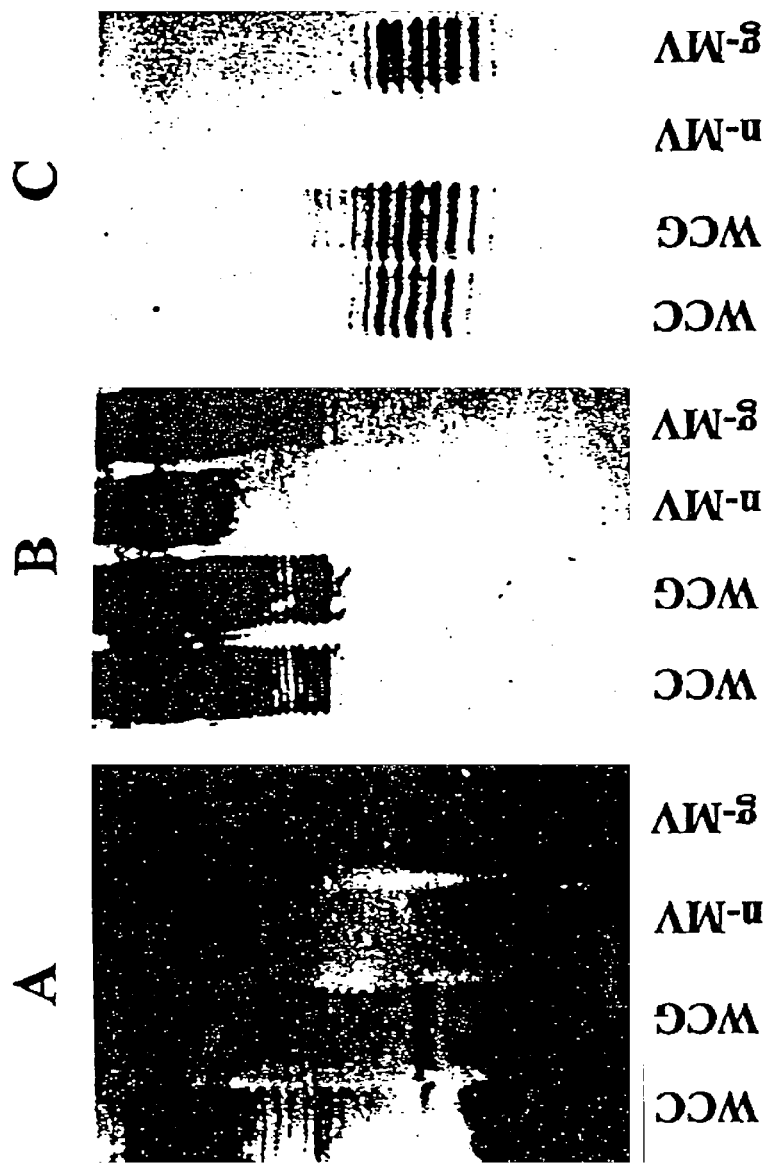
FIG. 4 is a silver stained SDS-PAGE of LPSs from *P. aeruginosa* whole control cells, whole cells exposed to four times the MIC of gentamicin, natural membrane vesicles and gentamicin membrane vesicles (A); an immunoblot comparing the LPS profile of (A) with B-band specific monoclonal antibodies (B); and, an immunoblot comparing the LPS profile of (A) with A-band specific monoclonal antibodies (C)

Most P. aeruginosa strains coexpress two chemically and immunologically distinct types of LPS when grown in laboratory culture, namely A-band and B-band LPS (Lightfoot, J. and J. S. Lam, J. Bacteriol. 173:5264–5630, 1991; and Rivera, M. et al., J. Bacteriol. 170:512–521, 1988). LPS samples were separated by SDS-PAGE and silver stained to characterize the carbohydrate moieties and banding patterns (FIG. 4(A)). To identify the A- and B-band LPSs, electrophoretic blots of LPS from the SDS-PAGE whose results are shown in FIG. 4(A) were reacted with either B-band (FIG. 4(B)) or A-band specific MAbs (FIG. 4(C)). The ladder-like banding pattern of LPS from both control and gentamicin treated cells were similar to the patterns reported previously (Lightfoot, J. and J. S. Lam, J. Bacteriol. 173:5264–5630, 1991; and Kadurugamuwa, J. L., et al Antimicrob. Agents Chemother. 37:715–721, 1993) and showed similar irregularities in the spacing and intensities of the bands. In addition, both types of MVs showed the presence of ladder-like LPS bands and core regions with relative mobilities similar to that of whole cells (FIG. 4(A)). However, the ladder-like banding pattern and intensity of the core region appeared to be less extensive in n-MVs (FIG. 4(A)). As expected immunoblotting of gentamicin-treated or control cells LPS reacted with both A band- and B-band specific MAbs showed coexpression of the A band and the B band, confirming the results of earlier studies (Lightfoot, J. and J. S. Lam, J. Bacteriol. 173:5264–5630, 1991; and Kadurugamuwa, J. L., et al Antimicrob. Agents Chemother. 37:715–721, 1993). In contrast, Western blots of LPSs from n-MVs and g-MVs reacted somewhat differently with B-band specific MAb. g-MVs possessed an increased amount of B-band LPS and its banding pattern was similar to that of whole cell extracts (FIG. 4(B)). The reaction of LPS from g-MVs with A-band specific MAb was weakly positive, while n-MVs did not demonstrate the presence of any A-band LPS whatsoever (FIG. 4(C)). This confirms that gentamicin has a greater affinity for highly charged B-band LPS; so much so that B-band LPS released in greater quantities to enrich-MVs (Kadurugamuwa, J. L., et al Antimicrob. Agents Chemother. 37:715–721, 1993).

Figure 5:
FIG. 5 shows immunogold electron microscopic detection of LPS on thin sections of natural membrane vesicles (A); and gentamicin membrane vesicles (B) with monoclonal antibody to B-band LPS, gentamicin membrane vesicles with monoclonal antibody to A-band LPS.

These results were further confirmed by immunogold electron microscopic detection of LPS on thin sections of nMV and g-MV. In particular, FIG. 5 shows immunogold electron microscopic detection of LPS on thin-sections of n-MVs (A) and g-MVs (B) with MAb to B-band LPS. Both types of MV appear heavily labelled with antibodies to B-band LPS. However, the degree of labelling was less in n-MV. Occasionally, g-MVs were labelled with MAb to A-band LPS (C; arrows) but n-MVs were never labelled for this LPS (not shown). The two MAbs labelled whole cells (containing both A- and B-band LPS) with the same effectiveness. Note that g-MVs are generally larger in diameter than n-MVs. Bar=100 nm.

Enzyme Activities

Tables 2 and 3 illustrate the enzymatic activities in cellular extracts, MVs and culture supenatants, from cultures which were treated with gentamicin or untreated. Both types of vesicles exhibit PLC activity, as measured spectrophotometrically by the hydrolysis of p-nitrophenylphosphrylcholine, indicating that the enzyme is associated with the MVs. To evaluate the PLC activity in the supernatants, the enzyme activity was assayed before and after the removal of vesicles from cell-free culture supenatants. Removal of vesicles from gentamicin-treated cultures resulted in an 83% reduction in enzyme activity as compared to a 68% decrease in untreated cultures (Table 3). This suggests that the majority of PLC secreted into the external environment is indeed concentrated in the vesicles. The observed difference in enzyme activity between the two cultures is due to the fact that the amount of vesicles per unit mass is greater in gentamicin-exposed cultures than in untreated cultures, hence a higher percentage of PLC activity is removed with the vesicles. It has been reported previously that P. aeruginosa produces and excretes two distinct PLCs with similar activities; each is capable of acting on the substrate, phosphatidylcholine (Shortridge, V. D. et al., Mol Microbiol. 6:863–871, 1992). Although both PLCs hydrolyse this substrate, one is hemolytic (PLC—H) for sheep and human erythrocytes and is heat labile, while the other (PLC—N) is not. Additionally, PLC—H can hydrolyse sphingomyelin, but not phosphatidylserine, whereas PLC—N hydrolyses phosphatidylserine but not sphingomyelin (Bergmann U., et al., Infect. Immun. 57:2187–2195, 1989; Berk, R. S. Infect. Immun. 55:1728–1730, 1987; and, Vasil, M. L. et al., Antibiot. Chemmmother. 44:34–47, Karger, Basel, 1991). The MVs were examined for hemolytic activity on sheep blood agar plates as well as spectrophotometrically on sheep blood cells, and it was found that both types of MVs were positive. No attempt was made to differentiate between PLC—H and PLC—N in the study.

Alkaline phosphatase activity was also detected in both MV preparations (Table 2). The total activity present in supernatants was reduced by approximately 50% after removal of MVs from culture supernatants, indicating an association of the enzyme with the vesicles (Table 3). Although most of the PLC and alkaline phosphatase were found within vesicles, enzymatic activities were also detected in cellular extracts after intact cells were treated with toluene, indicating that mature enzymes are accumulated within the cell before their release into the extracellular medium. Cell-associated activity of both enzymes has been reported previously (Ingram, J. M. et al., can. J. Microbiol. 19:1407–1415, 1973; Poole, K., and R. E. W. Hancock, FEMS Microbiol. Letts. 16:25–29, 1983, 1983; Tan, A. S. P. and E. A. Worobec, supra, 1993; and Vasil, M. L. et al., Antibiot. Chemother. 44:34–47, Karger, Basel).

P. aeruginosa secretes several proteases (Hastie, A., et al., Infect. Immun. 40:506–513, 1983; Kessler, e., et al., J. Biol. Chem. 268:7503–7508; Lazdusniski, A. J., et al., Biochimie 72:147–156, 1990; and, Wretlind, B., and O. R. Pavlovskis, Rev. Infect. Dis. 5:S998–1004, 1983).The secretion of elastase and protease was examined in strain ATCC 19660 since the amounts of both enzymes produced by this strain was found to be larger than those for strain H 103. No appreciable amount of proteolytic or elastolytic activity was detected in toluene cellular extracts, indicating the lack of intracellular accumulation of active enzymes (Table 2). This observation was in agreement with earlier work (Duoung, F. et al, Gene 121:47–54, 1992; Guzzo, J., et al, J. Bacteriol. 173:5290–5297, 1991; Hamood, A. N. et al., Infect. Immun. 60:510–517, 1992; Hastie, a. et al., Infect Immun. 40:506–513, 1983; Kessler, E., et al., J. Biol. Chem. 268:7503–7508, 1993; and Lazdusniski, A. J., et al., Biochimie 72:147–156, 1990). Examination of both types of MVs for protease activity demonstrated the association of active enzyme. On removal of vesicles from cell-free culture supernatants, the total protease activity dropped by 18% in untreated culture supernatants and 25% in gentamicin-treated culture supernatants. Since an appreciable amount of activity could also be detected in culture supernatants following the removal of vesicles from cell-free medium, the enzyme is probably released from cells in both soluble and vesicle-associated forms. In contrast, elastolytic activity was detected exclusively in culture supernatants and was not affected by removal of vesicles from cell-free culture supernatants. Previous studies have demonstrated that the enzyme is secreted as a proenzyme that becomes active only as it is released into the supernatant (Guzzo, J. et al., J. Bacteriol. 173:5290–5297, 1991; and Kessler, E. et al., J Biol. Chem. 268:7503–7508, 1993). For this reason, even if the proenzyme is present in MVs, it would not be detectable by its enzyme activity.

Localization of Enzymes by Immunoelectron Microscopy

Figure 6:
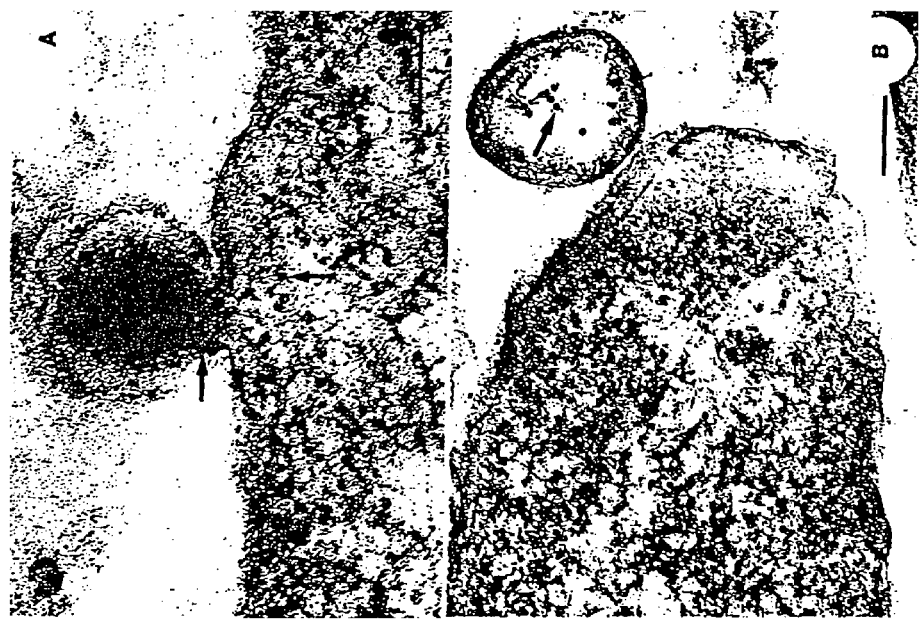
FIG. 6 shows immunogold electron microscopic detection of phospholipase C on thin sections of gentamicin membrane vesicles on the cell surface (A); and the separation of the gentamicin membrane vesicles from the cell (B)
Figure 7:
FIG. 7 shows immunogold electron microscopic detection of alkaline phosphatase in cells treated with gentamicin.
Figure 8:
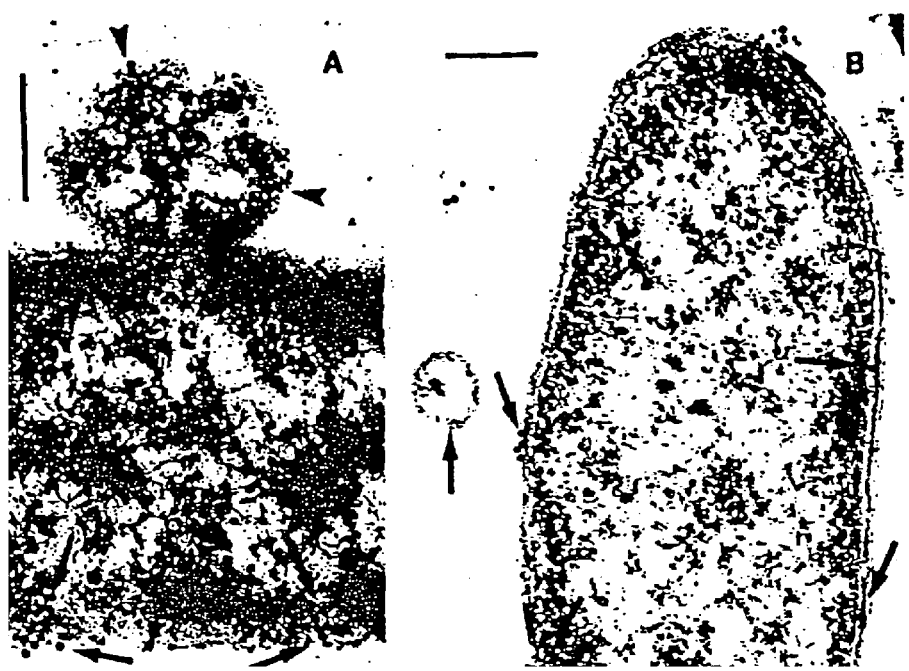
FIG. 8 shows immunogold electron microscopic detection of alkaline protease (A) and elastase (B) in cells treated with gentamicin.

Immunogold labelling of ultrathin sections with enzyme-specific antibody enabled subcellular visualization of the enzyme in intact cells and MVs. FIGS. 6 to 8 shows gentamicin-treated cells labelled for PLC.

In particular FIG. 6 shows immunogold electron microscopic detection of PLC on thin-sections of gentamicin-treated whole cells as g-MVs are formed and sloughed-off. FIG. 6(A) shows the formation of a vesicle on the cell surface. The enzyme is labelled in both the cytoplasm and the forming vesicle (arrows). Figure (B) shows a g-MV that has just separated from the cell. The lumen of the MV is labelled as is the cytoplasm of the cell (arrows). The periplasm was only occasionally labelled, presumably because most PLC was being rapidly packaged into MVs. Soluble extracellular enzyme would not be seen by this technique because of the numerous washing steps involved with fixing and embedding the cells. Similar results were obtained with n-MVs. Bar=100 nm.

FIG. 7 shows immunogold electron microscopic detection of alkaline phosphatase in cells treated with gentamicin. Note that the gold particles are associated with the outer membrane or are in the periplasm of intact cells and on the periphery of the released vesicle. Bar=100 nm.

FIG. 8 shows immunogold electron microscopic detection (A) alkaline protease and (B) elastase in cells treated with gentamicin. Note that a few gold particles are associated with the MV probed for alkaline protease (arrowheads) but not elastase (an MV is indicated with an arrow). A significant subpopulation of gold particles labelling alkaline protease and elastase appears to be located in discreet regions at or near the outer membrane (arrows), indicating the sites where the soluble enzymes are released. Bar=100 nm.

As judged by the location of gold particles on thin sections, a uniform distribution of the enzyme in the cytoplasm is clearly seen. Interestingly, it can also be seen that cytoplasm is streaming into a forming vesicle. Budding and free vesicles were labelled to the same extent with gold particles, demonstrating that PLC is entrapped within both types of MVs. This was in good agreement with the biochemical demonstration of the enzyme activity in vesicle preparations (Tables 2 and 3). Immunogold labelling for the localization of alkaline phosphatase in thin-sections of intact cells and MVs demonstrated that the majority of the enzyme was located in the envelope, particularly in the periplasm and outer membrane (FIG. 7). MVs were labelled on the membrane and on the luminal material attached to the membrane. g-MVs and n-MVs were labelled to approximately the same extent, confirming the result of the enzymatic assay (Table 2).

Little or no antibody was seen in the cytoplasm of thin-sectioned cells labelled for either alkaline protease or elastase (FIG. 8(A) and (B)). Gold particles were seen in MVs labelled for protease but the labelling was not as intense as for the previous enzymes. No MVs were labelled for elastase (FIG. 8(A)). These results were in good agreement with the bioassay (Table 3). For both elastase and protease, clusters of gold particles were located near the plasma membrane, within the cell envelope, or at the outer membrane surface. These are presumably the sites where the enzyme is being translocated through the envelope for release into the surroundings.

Immunological Detection

Western blots of cell extracts, MVs, and culture supernatants, before or after treatment with gentamicin were analysed by SDS-PAGE and probed with either elastase specific (FIG. 9(A)) or alkaline protease-specific polyclonal antiserum (FIG. 9(B)).

Figure 9:
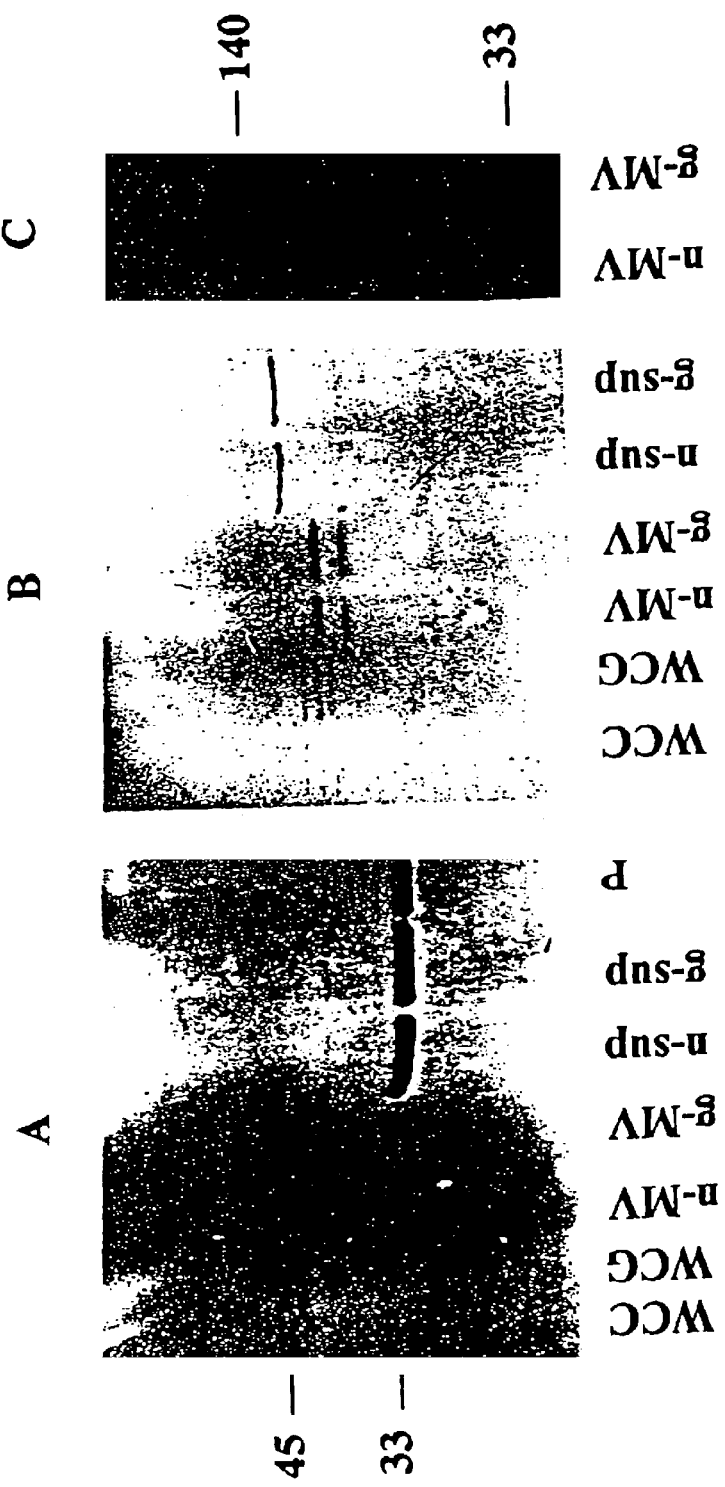
FIG. 9 are Western immunoblots of samples with antibodies to elastase (A) and alkaline protease (B), and showing proteinase present in membrane vesicles tested by gelatin zymography.

In particular, FIG. 9 shows Western immunoblot analysis of samples with antibodies to (A) elastase and (B) alkaline protease. Whole cell extracts from untreated control cells (WCC) or gentamicin-treated cells (WCG), n-MVs and g-MVs and cell-free supernatants after removal of MVs from untreated (n-sup) or gentamicin-treated (g-sup) cultures are shown. Lane P, contained purified elastase. Each lane contains 25 μg of protein or 10 μl of concentrated n-sup or g-sup. FIG. 9(C) shows proteinase present in MVs tested by gelatin zymography. Both n-MVs and g-MVs demonstrated three major bands ($M_r$~33, 35 and 135 kDa) having proteolytic activity. Molecular masses (in kilodaltons) are indicated of the left and right.

Elastase antigen with an apparent molecular weight 33 kDa, was detected in culture supernatants corresponding to the mature elastase from *P. aeruginosa* (FIG. 9(A)). A faint band corresponding to elastase together with two additional bands with molecular masses of ~42 and 45 kDa were seen in both types of MVs (FIG. 9(A)). Cellular extracts appeared to have two weakly reacting bands corresponding to ~32 and 45 kDa. These minor bands that were antigenically related to elastase are most likely the larger precursors of active mature elastase. In fact, when these precursors were treated in MVs by the method of Fecyz and Campbell (Eur. J. Biochem. 146:35–42, 1985) to remove non-covalently bound inhibitor molecules, elastase activity was restored (data not shown).

A major protein band with a molecular mass value of 48 kDa was seen in culture supernatants in the Western blot probed with alkaline protease specific antiserum (FIG. 9(B)). This is the same apparent molecular mass as the protease standard purified from *P. aeruginosa* culture supernatants (Lazdusnski, A., et al., Biochimie 72:147–156, 1990). Although, the results from the bioassay with Hide powder blue indicated proteolytic activity associated with MVs (Table 2), Western blot analysis with antibodies specific to alkaline protease did not show an antigenically-related band corresponding to the 48 kDa enzyme (FIG. 9B), suggesting that the proteolytic activity seen in the enzyme assay is most probably due to protease(s) other than alkaline protease. The MVs and cell extracts expressed two or three faintly stained bands in the range of 40–45 kDa, when reacted with alkaline protease-specific antibodies. These antigenically related bands may be degradation products or precursors of alkaline protease. However, previous investigators have been unable to detect intracellular proenzyme. Since it has been demonstrated that cell-bound protease degrades rapidly (Guzo, J., et al., J. Bacteriol. 173:5290–5297, 1991), it is possible that these bands represent degradation products which are recognized by the antibodies. Clearly, too some labelling is also seen on the thin sections (FIG. 8A). However, the presence of proteinases in MVs was clearly demonstrated on zymogram gels (FIG. 9C). Both MVs are composed of three major proteolytically active polypeptides with different molecular masses ($M_r$~33, 35 and 135 kDa), suggesting that the vesicles indeed possess protease activity, confirming the enzyme assay (Tables 2 and 3).

Alkaline phosphatase occurs in two varieties, high-$M_r$, alkaline phosphatase (H-phosphatase) and low-$M_r$ alkaline phosphatase (L-phosphatase) (Tan, A. S. P. and E. A. Worobec, FEMS Microbiol. Letts. 106:281–286, 1993). A single band with an $M_r$ of ~51 was seen in the Western blot when probed with polyclonal antiserum raised against H-phosphatase. No band was seen when the blot was probed with L-phosphatase. The synthesis of H-phosphatase is known to proceed constitutively, whereas L phosphatase must be induced by phosphatase limitation in the growth medium (Tan, A. S. P. and E. A. Worobec, FEMS Microbiol. Letts. 106:281–286, 1993). Since the culture medium used to grow the cells was not phosphate-limited, L-phosphatase was not expressed.

Fluorometric Quantification of DNA in Membrane Vesicles

To determine whether DNA is packaged within vesicles, MVs from two different strains of *P. aeruginosa* were analysed for DNA content by a highly sensitive, DNA-specific assay. As seen in Table 4, DNA was found in both n-MVs and g-MVs from both bacterial strains. More was found in the latter than the former, and strain ATCC 19660 packaged more DNA into MVs than did strain H103. During the assay, DNA must first be liberated from vesicles for accurate fluorometric detection. Since some DNA may remain stuck to membrane fragments (as they are being separated from the analysis liquor), ammonium hydroxide-Triton X-100 was used to solubilize MVs for some analyses; the DNA content of all solubilized samples was consistently greater than that found when intact membranes were removed (cf., results for solubilized versus intact MVs in Table 4). This difference could simply be due to the sticky nature of DNA (thereby reflecting indiscriminate membrane binding) or it could reflect a truly membrane-bound fraction. TEM of rotary-shadowed samples showed linear strands resembling DNA in each preparation but, no accurate estimation of membrane association could be made (data not shown). Table 4 also shows there were clear differences between the amounts of DNA found from the MVs of the two bacterial strains, and it is possible that the degree of DNA entrapment in MVs was strain dependent.

Because the MVs were isolated from early stationary phase growth cultures, it was also possible that some of the DNA was derived from lysed cells (within each culture) which had bound to the outer face of the vesicles. This could especially be true of g-MVs. Control experiments conducted with exhaustive treatment of MVs with pancreatic DNase showed that this was not the case. DNase-treated n- and g-MVs possessed amounts of DNA similar to those in Table 4. These control experiments also confirmed that the MVs were intact, since the DNA of the MVs was protected from the external enzyme. When in similar experiments containing MVs and free DNA were treated with pancreatic DNase, and ethidium-bromide gel electrophoresis was performed, the external DNA was shown to be digested whereas the MV DNA remained intact.

Example 2
Integration of the MVs Membrane with Carrier Strain

The following materials and methods were utilized in the investigations outlined in Example 2:

Bacterial strains and growth conditions. *P. aeruginosa* H 103 (Kadurugamuwa, J. L., et al., J. Bacteriol. 175:5798–5805, 1993), *P. aeruginosa* PAO1 serotype 05, *Shigella flexneri* M90T (Kadurugamuwa, J. L., et al. 1991, Infect. Immun. 59:3463–3471), *Escherichia coli* DH5α, (Kadurugamuwa, J. L., et al., J. Bacteriol. 175:5798–5805, 1993) and *Salmonella typhi* Ty21a (Swiss Serum and Vaccine Instituter, Berne, Switzerland) were grown in Trypticase soy broth to early stationary phase on an orbital shaker at 37° C. with an agitation rate of 125 rpm.

Isolation of Membrane vesicles (MV). MVs from one liter of *P. aeruginosa* H 103 and *Shigella flexneri* M90T were isolated as described above.

Integration of MV into attenuated strains. Exponential-growth-phase cultures (*E. coli* DH5α, and *S. typhi*Ty21a) were diluted in phosphate buffered saline (PBS) to produce a bacterial suspension of $10^6$ CFU/ml and were incubated at 37° C. for 15 min. with MVs (100 µg/ml of protein) from either *P. aeruginosa* H 103, or *Shigella flexneri* M90T or mixture of both.

Removal of unbound MVs. The unbound MVs were removed from suspension by filtering through 0.22 µm-pore-size cellulose acetate membrane and 10 ml of PBS were passed through the membrane to remove residual unbound MVs. Samples were examined by TEM to confirm the complete removal of non-integrated MV from cell suspension.

Electrophoresis. Attenuated strains with integrated MVs (a 40 µg-sample of protein) were digested with proteinase K (100 µg/ml) (Sigma Chemical Co., St. Louis, Mo.) and were separated by sodium dodecyl sulfate (SDS)-polyacrylamide gel electrophoresis (PAGE) as described above in Example 1. The integration of surface antigens (LPS) into attenuated strains were detected using Western immunoblotting as described above.

Western immunoblotting. Samples from SDS-PAGE were transferred to nitrocellulose and reacted with either monoclonal antibodies for *P. aeruginosa* B-band serotype 05 (see Example 1) or rabbit polyclonal antibodies to the purified LPS from *S. flexneri* (Kadurugamuwa, J. L., et al. 1991, Infect. Immun. 59:3463–3471).

Immunolabelling of whole cells or thin sections. Whole mounts or thin-sections of attenuated strains with integrated MVs were indirectly labelled with either anti-mouse immunoglobulin M gold (15 nm) or anti-rabbit immunoglobulin protein-A gold (5 nm) (EY Laboratories, San Mateo, Calif.) as described above.

Figure 11A:
FIG. 11A shows immunogold electron microscopic detection of *P. aeruginosa* LPS on purified membrane vesicles using the immunoglobulin M gold procedure.
Figure 11B:
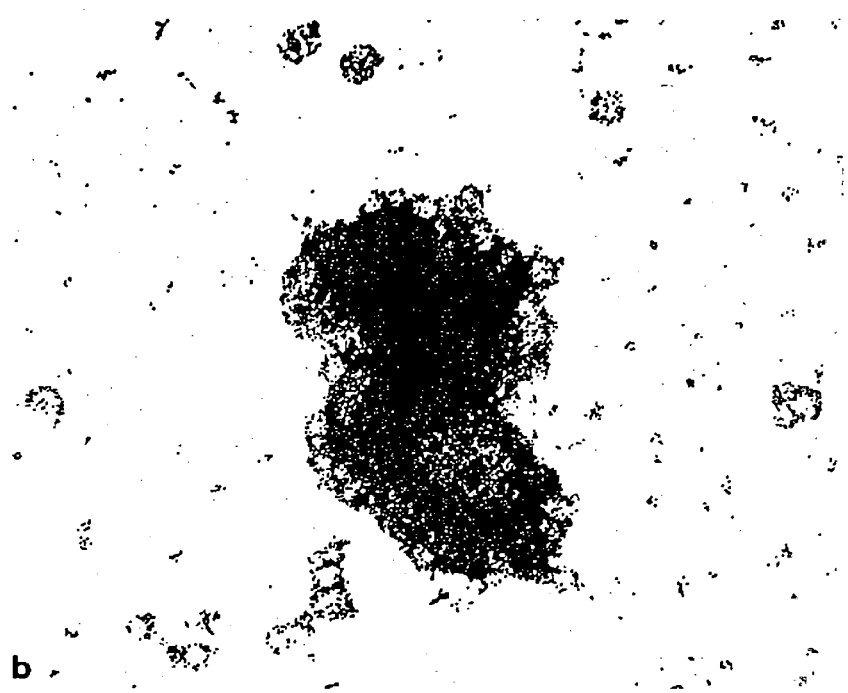
FIG. 11B is a negative stain showing *E. coli* DH5α carrying LPS from *P. aeruginosa*.
Figure 11C:
FIG. 11C is a thin section showing *E. coli* DH5α carrying LPS from *P. aeruginosa*.
Figure 11D:
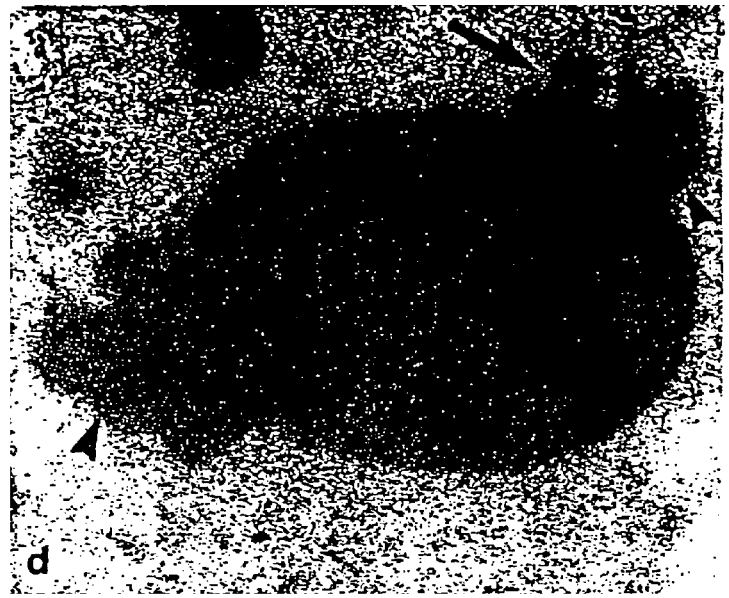
FIG. 11D is a negative stain showing the fusion of *S. flexneri* and *P. aeruginosa* LPS with *S. typhi* Ty21.
Figure 11E:
FIG. 11E is a thin-section showing the fusion of *S. flexneri* and *P. aeruginosa* LPS with *S. typhi* Ty21.

FIG. 11A shows immunogold electron microscopic detection of *P. aeruginosa* LPS on purified MVs using the immunoglobulin M gold procedure. FIG. 11B shows a negative stain and FIG. 11C is a thin section showing *E. coli* DH5α carrying LPS from *P. aeruginosa*. FIG. 11D shows a negative stain and FIG. 11E is a thin-section showing the fusion of *S. flexneri* (5 nm) (arrow head) and *P. aeruginosa* LPS (15 nm) (arrow) with *S. typhi* Ty21. Similar results were obtained with *E. coli* DH5α. Note that the gold particles specifically labelled the foreign antigens on the carrier strain. The firm i.e. stable integration of the MVs membrane with carrier strain is clearly visible. This example illustrates that heterologous antigens can be incorporated into a single carrier strain using the MV system. These antigens (LPS) are known to produce protective immunity. The resulting attenuated strains carrying heterologous LPS antigens were used for immunization to determine the host response to the delivered LPS antigens.

Figure 12A:
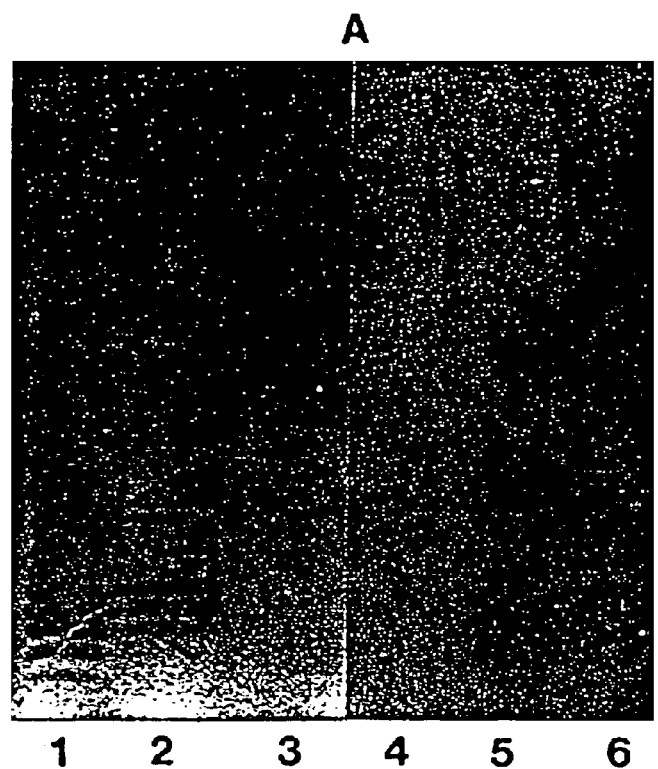
FIG. 12A is a Western immunoblot of samples with antibodies to *P. aeruginosa* LPS.
Figure 12B:
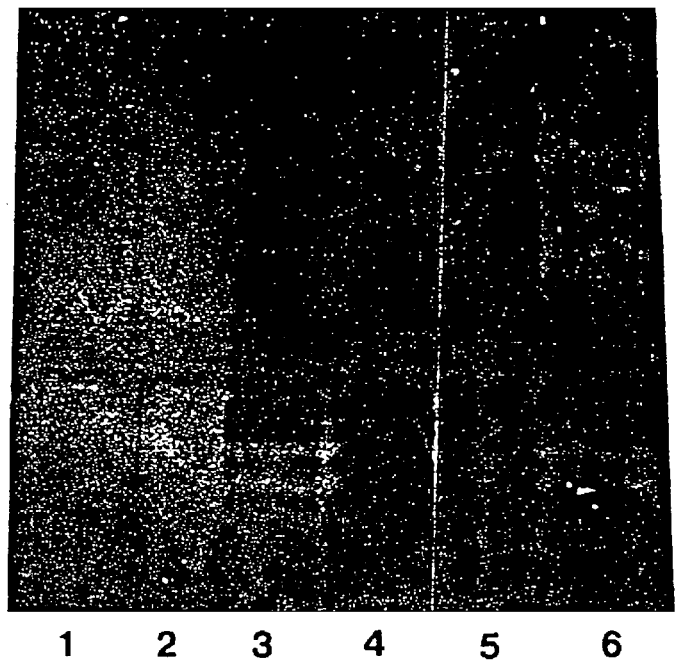
FIG. 12B is a Western immunoblot of samples with antibodies to *S. flexneri* LPS.

FIGS. 12A and 12B show a Western immunoblot analyses of samples with antibodies to either *P. aeruginosa* (A) or *S. flexneri* LPS (B). *S. typhi* Ty21a or *E. coli* DH5α cells were incubated with a mixture of purified MVs from *P. aeruginosa* and *S. flexneri*. The unbound MVs were removed and the integrated antigens were detected by incubation with antibodies to *P. aeruginosa* and *S. flexneri* LPS. In FIG. 10A: lanes 1. H103 whole cell; lane 2. H 103 MV; lane 3. DH5α whole cells+M90T MV+H 103 MV; lane 4. M90T whole cells; lane 5. M90 T MV, 6. Ty21a whole cells+M90T MV+H 103 MC. The results confirmed that LPS antigens were integrated into attenuated carrier strains. These results are in agreement with microscopic observations (cf. FIG. 11).

Example 3
Predatory Role on Other Bacteria and Drug Delivery System

The following materials and methods were utilized in the investigations outlined in Example 3.

Bacterial strains and growth conditions. *P. aeruginosa* H 103, (Kadurugamuwa, J. L., et al., 1993, J. Bacteriol. 175:5798–5805 1) *Staphylococcus aureus* Newman $D_2C$ (Sigma), *Escherichia coli* K12, were grown in Trypticase soy broth to early stationary phase on an orbital shaker at 37° C. with an agitation rate of 125 rpm.

Isolation of MV. MVs from one liter of *P. aeruginosa* H 103 were isolated as described above.

Bacteriolytic activity. The lytic activity of MVs from strain H103 was determined using *S. aureus* and *E. coli* as target organisms. Cells were suspended in 0.02 M Tris-HC1, pH 8.5 to produce a bacterial suspension of $10^8$ CFU/ml. At zero time, gentamicin-induced MV (g-MV) or natural MV (n-MV) (50 µg protein) were added and incubated at 37° C. The lytic activity was followed by viable counting on trypticase soy agar medium.

Action of lytic activity on glycyl peptides. Glycyl peptides (Sigma) to be tested (10 mM) were incubated for 3 h at 37° C. with 25 µg protein samples of MVs in a total volume of 50 µl of 0.02 M Tris-HC1, pH 8. After incubation, the reaction mixtures were separated by thin-layer chromatography on silica gen 60 (0.2 mm Sigma) with a mixture of butanol:acetic acid:water (4:1:1) as the solvent. After chromatography, the plates were sprayed with 0.02% ninhydrin in ethanol and heated at 80° C.

Isolation of peptidoglycan. The procedure described by Verwer et al (1978, J. Bacteriol. 136:723–721) was employed to prepare murein sacculi from *P. aeruginosa* H103 and *E. coli*.

MV digestion of sacculi. Purified sacculi were suspended in 0.02 M Tris-HC1, pH 8.5 to an optical density at 595 nm of 0.8 and incubated with 25 µg protein sample of MV for 15–30 min. at 37° C. After mild sonication, sacculi were negatively stained for 1 min. with aqueous 1% uranyl acetate solution. The stain was removed with filter paper, air dried, and electron micrographs were taken with a Philips 300 EM.

Zymogram analysis. The detection of cell wall degrading activity in gels containing peptidoglycan was carried out as previously described (Bernadsky, G., T. J. et al., 1994, J. Bacteriol. 176:5225–5232.).

Detection of gentamicin in MVs. g-MVs were analysed for the presence of antibiotic within MV using an enzyme-linked immuno assay (ELISA) using antiserum to gentamicin from Sigma.

Delivery of gentamicin into eucaryotic cells. The human intestinal epithelial cell line Henle 407 (ATCC strain CCL-6) was infected with *S. flexneri* as described previously (Kadurugamuwa, J. L., et al., 1991, Infect. Immun. 59:3463–3471). Monolayers were incubated with g-MV (100 µg protein/15×15 mm coverslip) and viability of intracellular S. flexneri were determined following the lysis of tissue culture cells as described previously (Kadurugamuwa, J. L., et al., 1991, Infect. Immun. 59:3463–3471).

Figure 13:
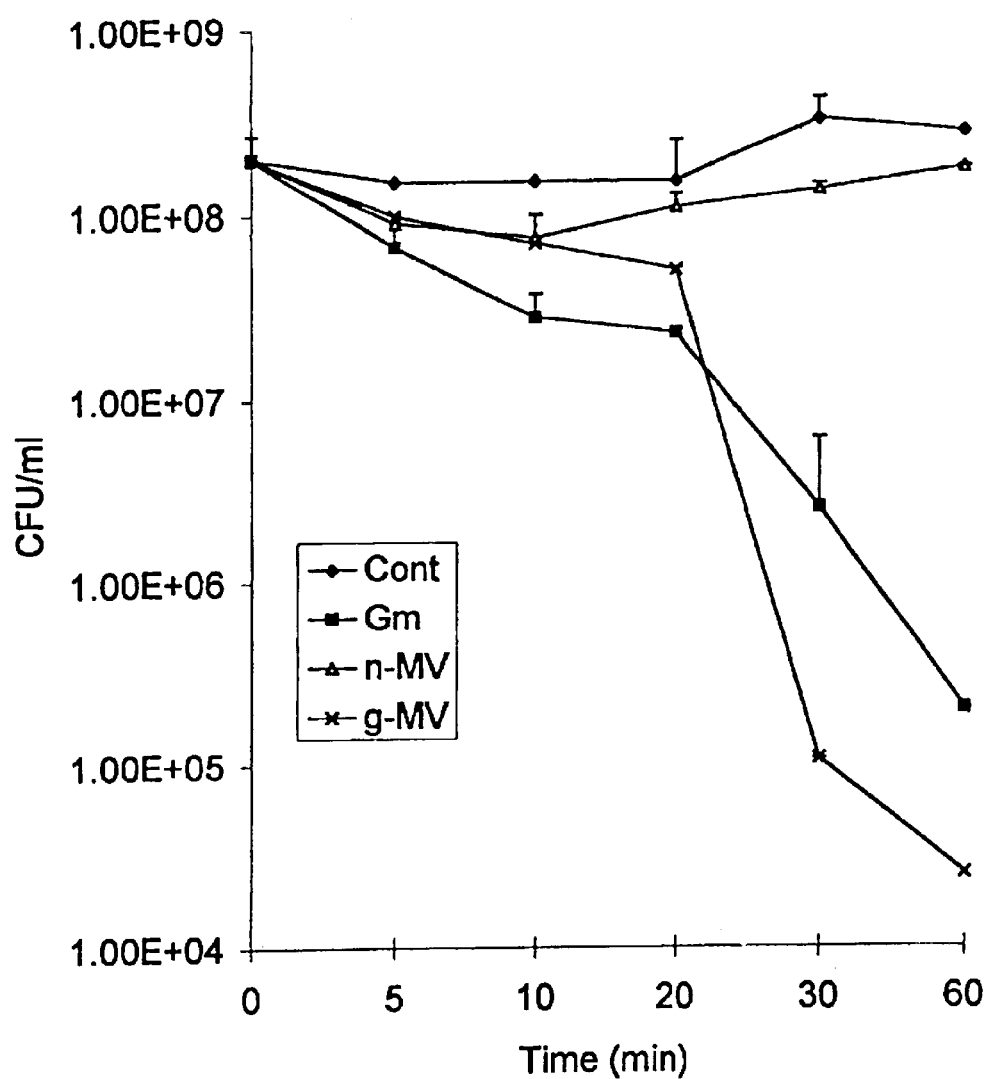
FIG. 13 is a graph showing the effect of natural membrane vesicles and gentamicin membrane vesicles on intact *E. coli* K 12.

FIG. 13 shows the effect of native-MV (n-MV) and gentamicin-MV (g-MV) on intact E. coli K 12. n-MV or g-MV were added to viable cells of E. coli and viability was monitored over 60 min. The control contained cells with no MVs. The results demonstrate that the MVs were capable of reducing the number of viable cells with time. g-MV were more lytic than the natural variety indicating the synergistic effect of the MVs' cell wall degrading capacity.

Figure 14:
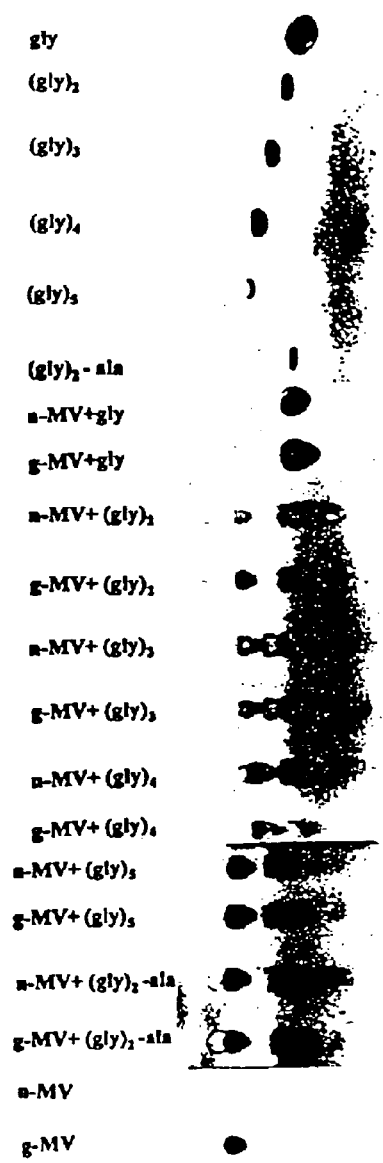
FIG. 14 is a chromatogram showing the separation of the products of action of *P. aeruginosa* membrane vesicles on glycyl-peptides.
Figure 15A:
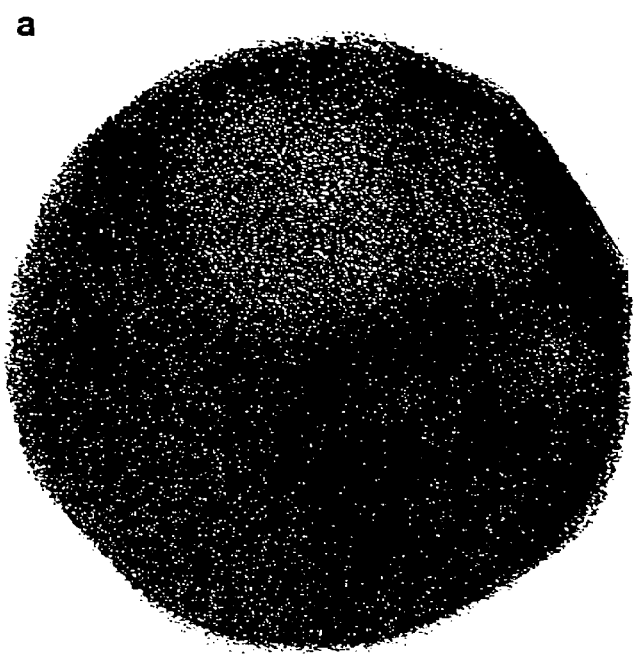
FIG. 15A is an electron micrograph of purified sacculi from *S. aureus*.
Figure 15B:
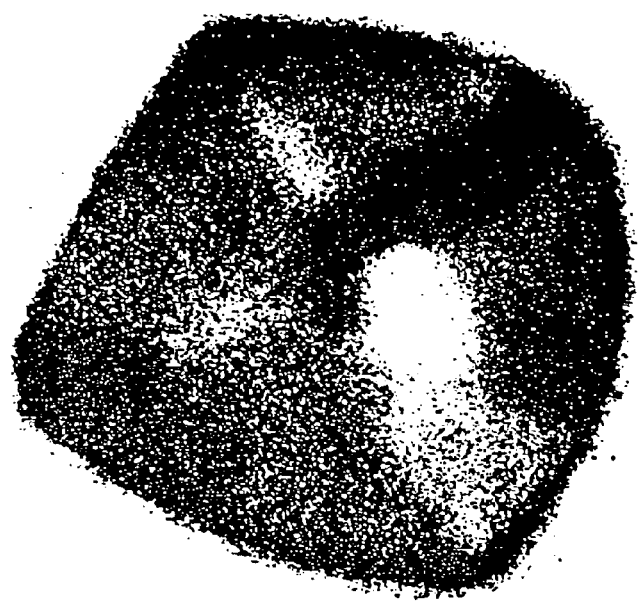
FIG. 15B is an electron micrograph of purified sacculi from *S. aureus* after incubating with membrane vesicles from *P. aeruginosa*.
Figure 15C:
FIG. 15C is an electron micrograph of purified sacculi from *E. coli*.
Figure 15D:
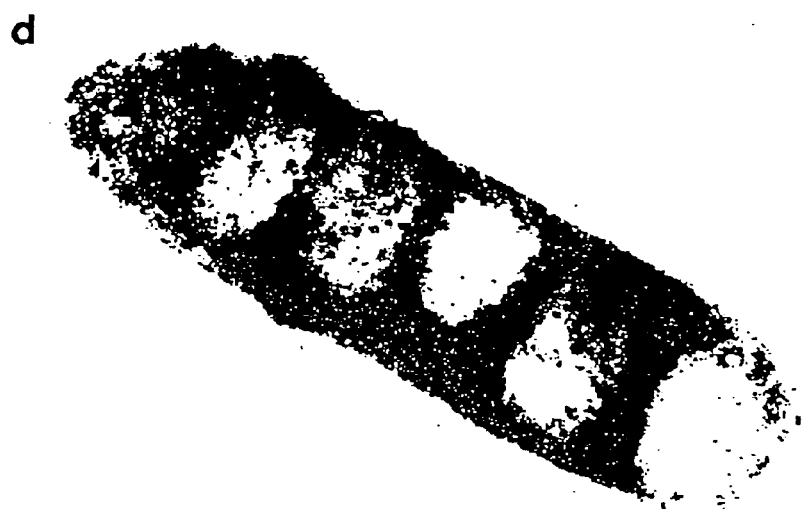
FIG. 15D is an electron micrograph of purified sacculi from *E. coli* after incubating with membrane vesicles from *P. aeruginosa*.

FIG. 14 shows the chromatographic separation of the products of action of P. aeruginosa MVs on glycyl-peptides. it demonstrates that the enzyme catalyzed the hydrolysis of peptidoglycan fragments and suggests that the MVs contain enzymes capable of lysing bacteria by acting on peptidoglycan of the rigid cell wall. The lytic enzyme appears to exhibit a rather high specificity for polyglycine cross-bridges (i.e., as an endopeptidase capable of splitting them into di- and triglycine peptides).

FIG. 15 shows electron micrographs of untreated purified sacculi from S. aureus (FIG. 15A) and E. coli (FIG. 15C), and S. aureus (FIG. 15B) and E. coli (FIG. 15D) sacculi after incubating with MVs from P. aeruginosa. Note that several areas of the MV treated sacculi are undergoing lysis in both of these gram-positive and gram-negative cell walls. This demonstrate the MVs capacity to hydrolyse the peptidoglycan from both gram-positive and gram-negative bacteria.

Figure 16:
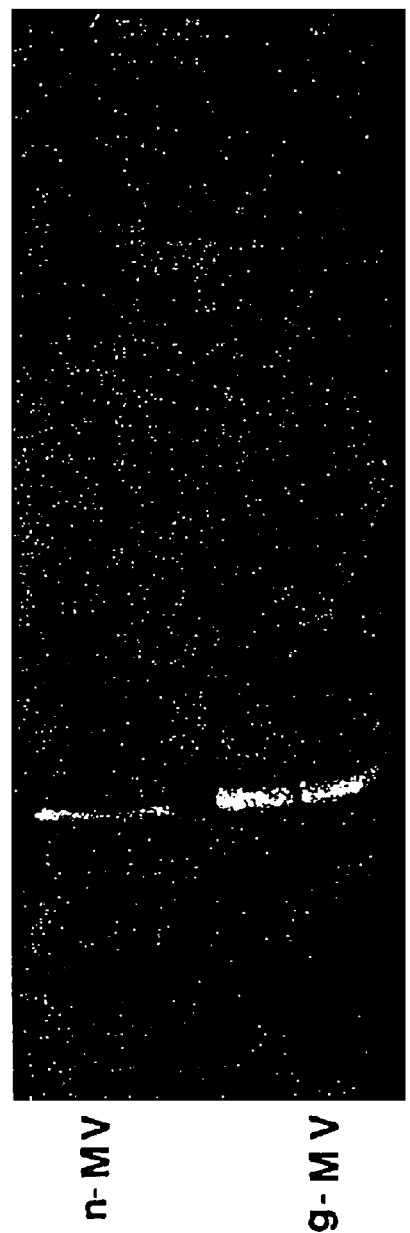
FIG. 16 is an electrophoretic profile (zymogram) of autolysin from membrane vesicles.

FIG. 16 is an electrophoretic profile (zymogram) of autolysins from MVs. Bands with cell walls degrading enzyme activity were observed as clear zones in the opaque gel containing peptidoglycan fragments. The molecular weight of the major enzyme was determined to be around 31 kDa. These results confirm the results shown in FIGS. 13, 14 and 15.

Detection of gentamicin in MVs. ELISA assay demonstrated that g-MV contain 0.01 µg gentamicin/µg MV protein. This indicated that antibiotics, such as gentamicin, are associated or encapsulated within MV. The enhanced killing activity of g-MV on E. coli seen in FIG. 11 is most likely due to the association of antibiotic and the possession of hydrolytic enzyme within MV. These two in concert have an additive effect on live bacteria.

Delivery of drugs into eucaryotic cells. Aminoglycoside antibiotics such as gentamicn are clinically useful potent drugs. However, one of the draw backs of this group of antibiotics is their impermeability into eucaryotic cells. When g-MV were incubated with human intestinal epithelial cell lines that were infected with S. flexneri, a ~30% reduction in viable intracellular bacteria was detected. This suggests that impermeable drugs such as gentamicin could be administered into eucaryotic cells using the MV system.

Example 4
Targeted Drug Delivery

The following materials and methods were utilized in the investigations outlined in Example 3.

Bacterial strains and growth conditions. P. aeruginosa H 103, (Kadurugamuwa, J. L., et al., J. Bacteriol. 175:5798–5805.) and S. flexneri M90T (Kadurugamuwa, J. L., et al., 1991, Infect. Immun. 59:3463–3471) were grown in Trypticase soy broth to early stationary phase on an orbital shaker at 37° C. with an agitation rate of 125 rpm.

Isolation of MV. MVs from one liter of P. aeruginosa H. 103 were isolated as described above (See Example 1).

Outer Membrane Protein (OMP) profile. OMP from S. flexneri were analysed as described above (See Example 1).

Electron Microscopy. Purified MV from P. aeruginosa were negatively stained and observed for appendages such as pili and fimbriae using a Philip 300 EM.

MVs can be used to directly target a drug to the tissue where it is most needed. Specificity can be obtained by incorporating carbohydrate, proteins, glycoproteins or glycolipids to the MVs' surface to produce ligand-coated vesicles specific for distinct tissue. Alternatively, specific adhesins such as bacterial fimbriae can be used on the MV surface. (The present inventors have determined that MVs from P. aeruginosa and S. flexneri possess fimbriae and invasive membrane proteins on the surface of MVs). This enables targeting to only the tissues at risk while reducing the exposure of other tissues to toxic side effects of the drug. Slow sustained release of drug from vesicles can prolong the residence time of the drug in areas where most needed.

Example 5

Aminoglycoside antibiotics such as gentamicin, tobromicin, and amikacin are potent antimicrobial agents active against both gram-negative and gram-positive bacteria. However, these compounds are not effective against pathogens such as Shigella, Liegeonella, Mycobacteria, Listeria, or Salmonella, during their intracellular growth cycle because of the impermeability of the drug into eucaryotic cells (Kadurugamuwa et al., 1991, Infect. Immun. 59:3464–3471).

Figure 17:
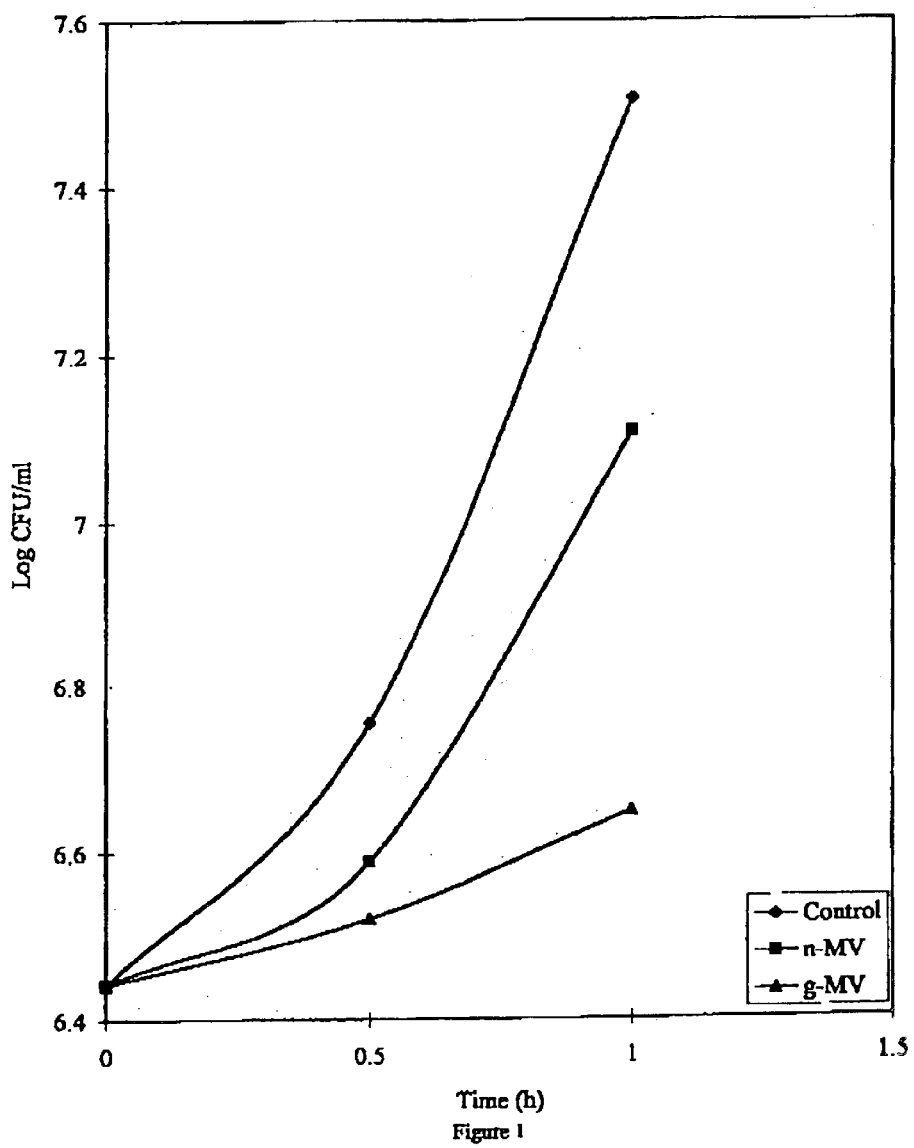
FIG. 17 is a graph showing the effect of g-MV on intracellular *S. flexneri*.

It has been demonstrated that these compounds (e.g. gentamicin) become encapsulated in the lumen of MVs during their formation (0.1 µg gentamicin/µg MV protein; g-MVs) if the organism is grown in the presence of antibiotic as described in Examples 1 and 2. Immunogold electron microscopic labeling of thin-sections with antibodies specific to S. flexneri LPS was used to demonstrate the fusion or adherence of bilayered MVs with eucaryotic cells. The integration of MVs with these cells was clearly visible. The MVs being bilayered membranes of small size allow them to readily fuse with the plasma membrane of other cell systems. Incubation of g-MVs (25 µg MV protein/25 cm$^2$ cover slip) with S. flexneri infected human colonic epithelial cells (10$^7$ CFU/25 cm$^2$ cover slip) (Kadurugamuwa et al, 1991 Infect. Immun. 59:3464–3471) inhibited the multiplication of intracellular bacteria by approximately 88% in the first hour of incubation (FIG. 17). Antibiotic was detected in the cytoplasm of S. flexneri infected cells indicating that the drug had indeed penetrated the cytoplasm of epithelial cells, following the fusion of MV. Gentamicin could only enter these cells because it was packaged into a bilayered MV which could diffuse with the otherwise impermeable membrane and liberate its contents into the cytoplasm. Soluble antibiotic had no effect on growth of intracellular bacteria confirming the impermeability of eucaryotic cell membrane to the antibiotic (FIG. 17). Intracellular bacterial cell number remained constant for the first 0.5 h in cells incubated with n-MV and gradually increased by 1 h to those of the control cultures. The small effect of n-MVs on intracellular bacteria was presumably due to murein hydrolases in n-MVs.

Example 6
Materials and Methods

Bacterial strains and growth conditions. P. aeruginosa PAO1 serotype O5 (a gentamicin sensitive strain that produce large quantities of g-MVs during gentamicin treatment), P. aeruginosa 8803 (a strain with permeability—type gentamicin resistance) (Bryan, L. E. et al. 1984 Antimicrob. Agents Chemother. 26:250–255), *Staphylococcus aureus* Newman D$_2$C (SigmaChemical Co. St. Louis, Mo.)) and *Escherichia coli* DH5α, were grown in Trypticase soy broth (TSB) to early stationary phase on an orbital shaker at 37° C. with an agitation rate of 125 rpm.

Antibiotic susceptibility. The susceptibilities of bacterial strains to gentamicin (Sigma) were determined by broth dilution method in Muller-Hinton broth (Kadurugamuwa, J. L. et al, 1993 Antimicrob. Agents Chemother. 37:715–721). The MICs for PAO1, 8803, D$_2$C, and DH5α were 2, 128 (10), 1.0, and 1.0 μg/ml, respectively.

Isolation of MV. MVs from one liter of *P. aeruginosa* PAO1 were isolated as described above.

Bacteriolytic activity. The lytic activity of MVs from strain PAO1 was determined using *S. aureus* D$_2$C, *E. coli* DH5α, *P. aeruginosa* strains PAO1 and 8803 as target organisms. Exponential growth phase cultures grown in TSB were diluted in fresh TSB to produce a bacterial suspension of $10^8$ CFU/ml. At zero time, either gentamicin (100 μg/ml for strain 8803 or 2.5×MIC for the other strains) or MVs (either n-MVs (either n-MVs or g-MVs at 100 μg protein/ml) were added to the cultures and incubated at 37° C. The bactericidal activity was followed by viable counting at various times (0–5 h) on Trypticase soy agar medium.

Hydrolytic action on glycyl peptides. The glycyl peptides (Sigma) to be tested (10 mM) were incubated for 3 h at 37° C. with 25 μg protein samples of MVs in a total volume of 50 μl of 0.02 M Tris-HCl, pH 8. After incubation, the reaction mixtures were separated by thin-layer chromatography on silica gel 60 (250 μm Sigma) with a mixture of butanol:acetic acid:water (4:1:1) as the solvent. After chromatography, the plates were sprayed with 0.02% ninhydrin in ethanol and heated at 80° C.

Isolation of peptidoglycan. The procedure described by Verwer et al (1978. Arrangement of glycan chains in the sacculus of Escherichia coli 136:723–729) was employed to prepare murein sacculi from *P. aeruginosa* PAO1, *E. coli* and *S. aureus*.

MV digestion of sacculi. Purified sacculi were suspended in 0.02 M Tris-HCI, pH 8.5 to an optical density at 595 nm of 0.8 and incubated with a 25 μg protein sample of MVs for 15–30 min. at 37° C. After mild sonication, to separate clumped material, sacculi were negatively stained for 1 min. with aqueous 1% uranyl acetate solution air, dried, and electron micrographs taken with Philips EM300 operating under standard conditions at 60 kV with anticontaminator in place.

Zymogram analysis. The detection of cell wall degrading activity in gels containing murein sacculi from PAO1 was carried out as previously described (Bernadsky, G. T. J. et al., J. Bacteriol 176:5225–5232).

Detection of gentamicin in g-MVs. g-MVs were analysed for the presence of associated antibiotic by an enzyme-linked-immuno assay (ELISA) using antiserum to gentamicin which was obtained from Sigma.

Fusion of MVs with other bacteria. The integration of MVs from *P. aeruginosa* with other bacteria was demonstrated by immunolabelling thin sections of these bacteria with monoclonal antibodies for *P. aeruginosa* B-band serotype O5 (LPS) as described above.

Experimental Results

Figure 18:
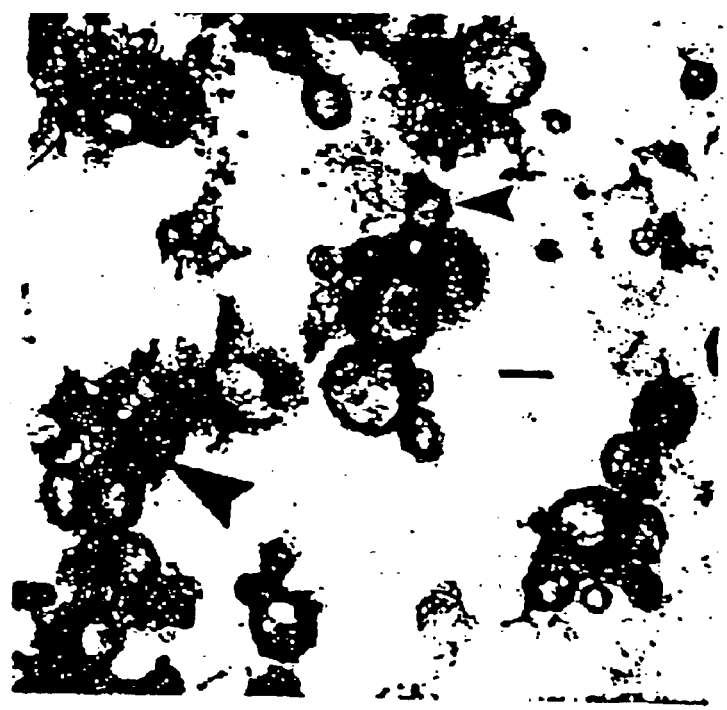
FIG. 18 is an electron micrograph of negatively stained g-MVs.

Negative stains of the MVs: FIG. 18 shows the intact, isolated, purified MVs from gentamicin-treated cells of *P. aeruginosa* PAO1. Although these bilayered vesicles are partially collapsed, most were filled with a particulate substance and each MVs was ca. 100 nm in diameter. Thin sections of the MVs from previous work also showed the vesicles to be filled with substance.

Figure 19:
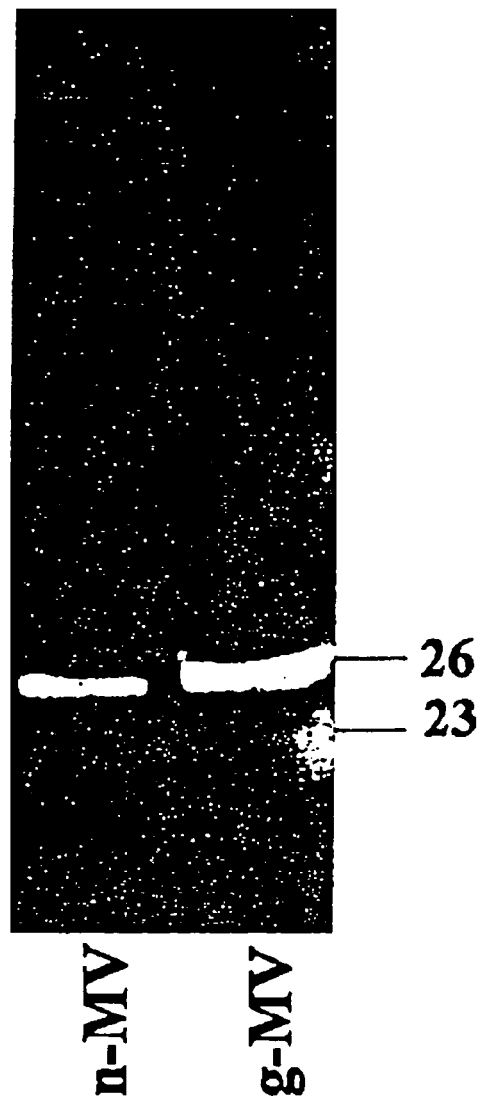
FIG. 19 is an electrophoretic profile (zymogram) of autolysin from MVs.

Autolysin profile: The electrophoretic profile (zymogram) of autolysin from n-MVs and g-MVs is shown in FIG. 19. One zone ($M_r$ 26 kDa) with cell-wall degrading activity was observed as a clear band in the opaque gel containing murein sacculi. Although the initial amount of material was constant for both n-MVs and g-MVs, the lytic activity of g-MVs appeared to be slightly greater. Furthermore, an additional, barely visible, lytic band (ca. $M_r$ 23 kDa) was also detected in g-MV.

Figure 20:
FIG. 20 are electron micrographs of purified sacculi from (A) *S. aureus* and (B) *E. coli* (C) *S. aureus* and (D) *E. coli* sacculi after incubating with MVs from *P. aeruginosa*.

Negative stains of sacculi treated with MVs. *S. aureus* and *E. coli* sacculi that have been incubated with MVs from *P. aeruginosa* are shown in FIG. 20. It was clear that several areas of the murein network have been degraded in both preparations demonstrating the MVs capacity to hydrolyse the peptidoglycan from both gram-positive and gram-negative bacteria. These degraded regions were not due to native autolysins nor to the forces of surface tension during negative staining since controls without MVs showed no degradation of the sacculi.

Figure 21:
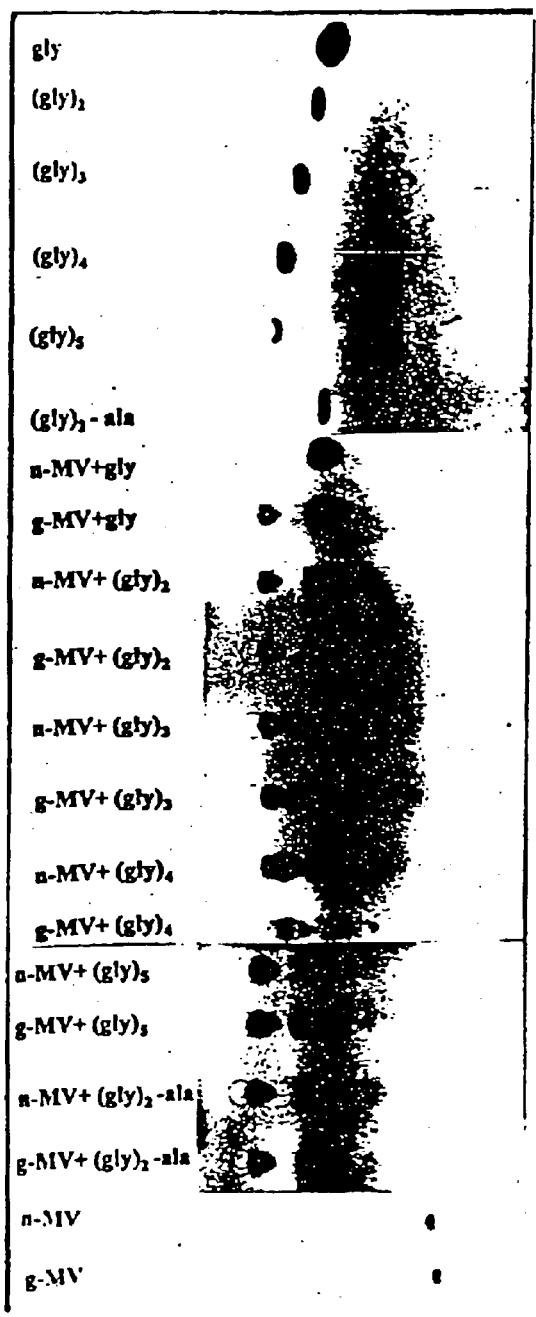
FIG. 21 shows chromatographic separation of the products of action of *P. aeruginosa* MVs on glycyl-peptides.

Action of the lytic enzyme on glycyl peptides. FIG. 21 shows the chromatographic separation of the hydrolysis products of MVs on glycyl peptides. Even though MVs could hydrolyse the A1γ peptidoglycan of *P. aeruginosa* PAO1 murein sacculi (FIG. 19) which is directly cross-linked and which does not contain polyglycyl linkage units, (Schleifer K. H. et al, 1972 Bacteriol. Rev. 36:407–471) it was apparent that the MVs also possessed the capability of hydrolysing polyglycine units such as those found in certain gram-positive peptidoglycan cross-bridging units such as those in *S. aureus*.

Figure 22:
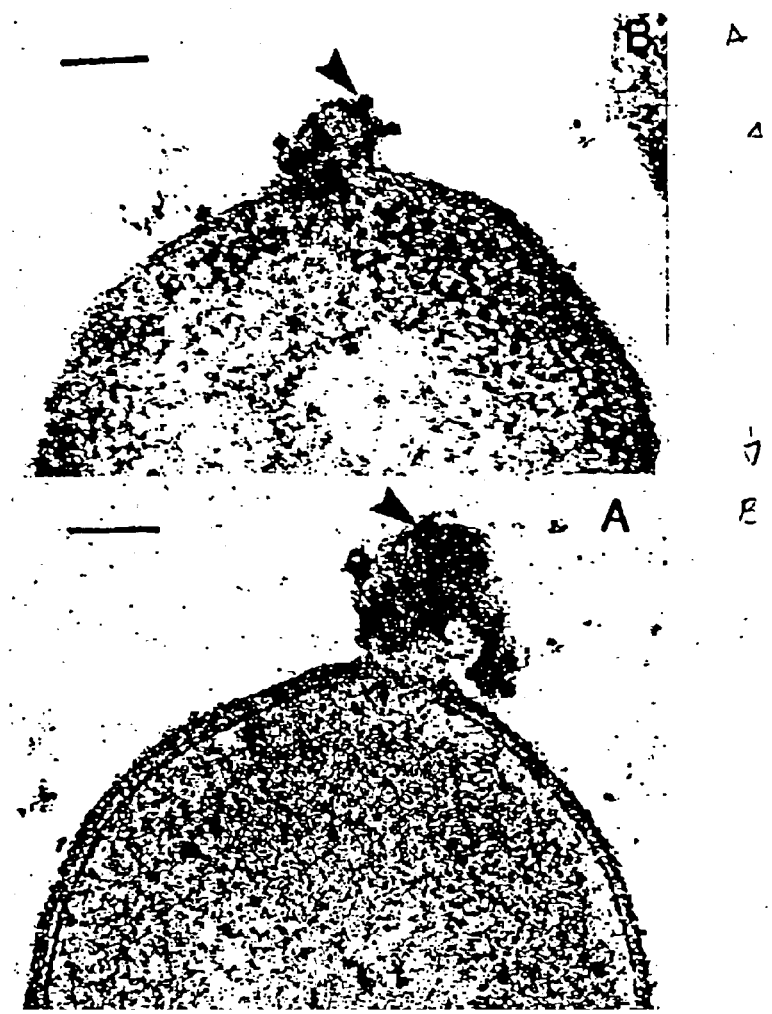
FIG. 22 shows fusion of *P. aeruginosa* MVs with (A) *E. coli* and (B) *S. aureus*.

Fusion of MVs with other bacteria. Immunogold electron microscopic labelling of thin-sections with antibodies specific to *P. aeruginosa* LPS was used to demonstrate the fusion or adherence of bilayered MVs with other bacteria. The integration of MVs with both *S. aureus* and *E. coli* is clearly visible (FIG. 22). The MVs being bilayered membranes of small size allow them to readily fuse with the outer membrane of other gram-negative systems. The initial binding and fusion of MVs to the outer membrane of *E. coli* is shown in FIG. 22(A). The actual breakdown of the peptidoglycan layer, before lysis, is extremely difficult to capture by electron microscopy since it the lytic event proceeds so rapidly. Clearly, it happens, since there is a substantial drop in light scattering due to degradation of murein sacculi (~30% within 5 min) if the process is followed by $OD_{595}$ readings. Although they cannot fuse to gram-positive walls (such as those of *S. aureus*), they appear to attach to and break open on the cell surface. The disintegration of the cell wall just underneath the MVs is clearly visible in *S. aureus* (FIG. 22(B)).

In the *P. aeruginosa* system, although most extracellular autolytic activity is associated with MVs, some soluble-activity can also be demonstrated. Therefore, once MVs are removed from the spent culture medium, there is still some residual peptidoglycan degrading activity. If *E. coli* is incubated with this spent liquor or the MVs lysate, there is no drop in viability indicated that the bacterium's outer membrane is an impermeable barrier to the soluble autolysins, this emphasizes the importance of the MV's bilayered membrane in directly entrapped autolysins to the *E. coli* (or other gram-negative) peptidoglycan layer. Once the MVs adhere to the outer membrane, the MV's membrane and outer membrane must fuse together, emptying the MV luminal contents into the host periplasm where the *P. aeruginosa* autolysins hydrolyse the peptidoglycan layer of intact cell.

Figure 23:
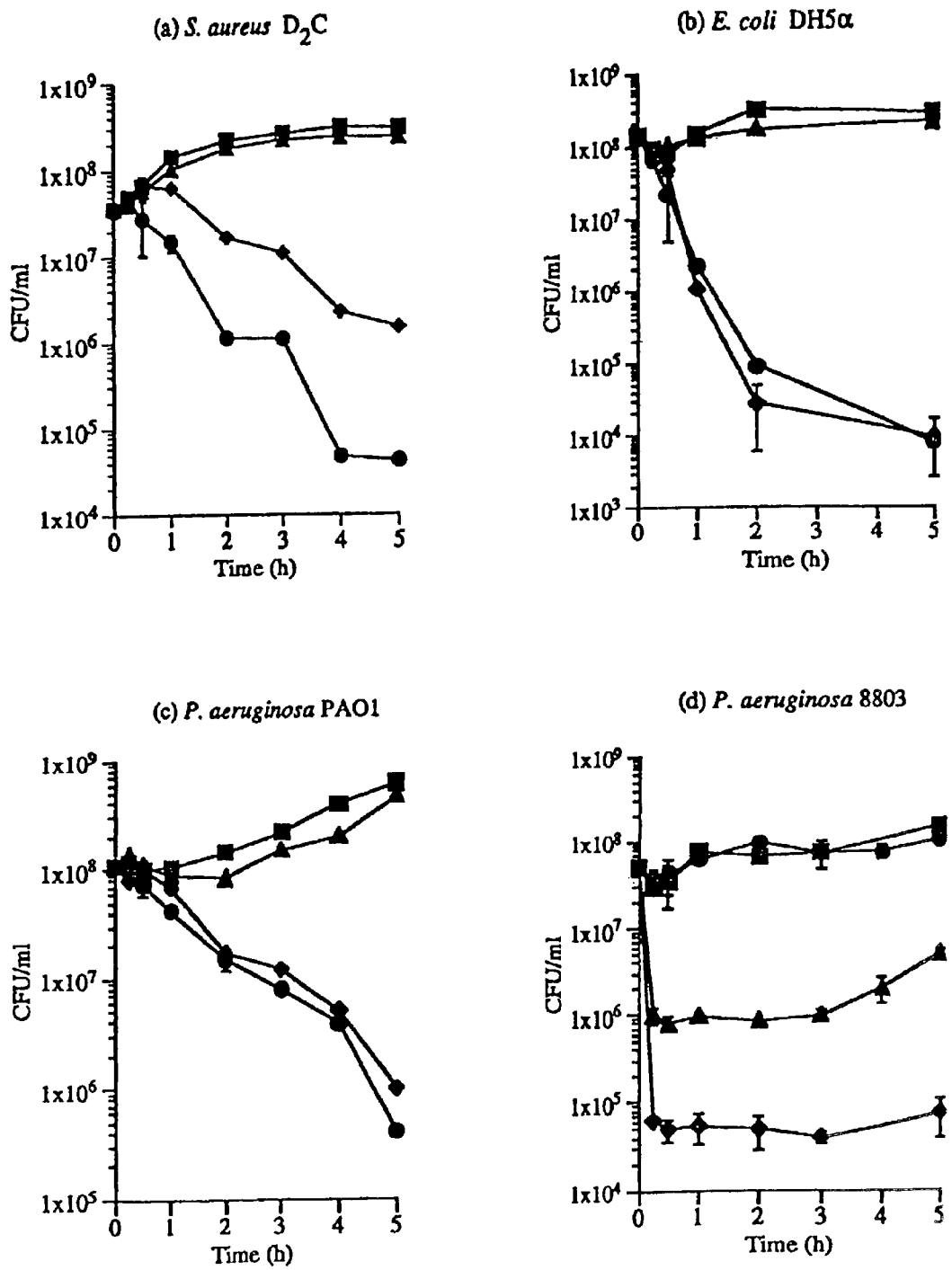
FIG. 23 are graphs showing the bactericidal effect of n-MV (▲) g-MV (♦) and gentamicin (●) on (a) *S. aureus* $D_2C$, (b) *E. coli* DH5α (c) *P. aeruginosa* PAO1 and (d) *P. aeruginosa* 8803.

Association of gentamicin with g-MVs. ELISA assays demonstrated that g-MVs contained ~4±1.8 ng gentamicin/

µg MV protein. This indicated that gentamicin is indeed associated with g-MVs. The enhanced killing activity of g-MVs on the bacterial strains seen in FIG. 23 is most likely due to the combined killing power of the antibiotic and the murein hydrolase activity of the MVs. Because of the enhanced killing, it is likely that gentamicin is entrapped in the lumen of MVs during their formation in the presence of the antibiotic and escapes along with autolysins into the periplasm of both the gram-positive and gram-negative strains (Beveridge, T. J. 1995, ASM News 61:125–130). Here, gentamicin must be actively transported to the cytoplasm and inhibits protein synthesis. The luminal location of the gentamicin and its transport into cells was demonstrated by immunogold-labelling of thin-sections with antibodies to gentamicin. Several gold particles per cell were clearly seen in the cytoplasm of g-MV incubated cells (including the permeability resistant strain of *P. aeruginosa*), but not those cells incubated with n-MVs (data not shown).

Antibacterial activity. The effect of n-MVs, g-MVs and gentamicin (2.5×MIC of antibiotic for gentamicin sensitive strains or 100 µg/ml of gentamicin for the 8803 strain) on the viability of $D_2C$, DH5α, PAO1, and 8803 is shown in FIG. 23. *P. aeruginosa* PAO1 is the parent strain from which the MVs are derived. It was exquisitely sensitive to both g-MVs and the free gentamicin at 2.5 MIC. There was a small but discernable loss of viability of *S. aureus, E. coli* and *P. aeruginosa* PAO1 (FIG. 23(*a*), (*b*) and (*c*) exposed to n-MVs. Even though peptidoglycan hydrolysis must have occurred (FIGS. 19 and 20), the loss in viability was less than expected. DH5α and PAO1 remained at a constant cell number for the first 1–2 h, and this gradually increased by 5 h. The n-MV cell numbers were only slightly reduced to those of the control cultures. The small effect of n-MVs on these cultures was presumably due to a rapid replacement of lysed cells with newly divided cells or to a rapid replacement of hydrolyzed peptidoglycan with newly synthesized polymer so that lysis was inhibited.

The killing curves for the soluble antibiotic and g-MVs were approximately equal, but independent, for both the PAO1 and DH5α strains in FIGS. 23(*b*) and (*c*). Yet, the amount of gentamicin in the g-MVs was comparatively small since it was ~¼–⅕ the MIC for both strains. However, the incubation of these strains with g-MVs resulted in a lysis equal in magnitude to a 2.5–6×MIC soluble gentamicin level. This more than 10-fold increase is presumably due to the additive effect of antibiotic and hydrolytic enzyme on the bacterial strains and emphasizes the potency of g-MVs.

The loss in viability of *S. aureus* exposed to g-MVs was similar to, but not as great as, that of the DH5α and PAO1 strains (FIG. 23(*a*)). Here, the soluble gentamicin concentration corresponded to a ~2.5×MIC of the antibiotic which was still much greater than that concentration directly associated with the g-MVs (i.e., ~¼×MIC). Gram-positive walls are capable of withstanding greater turgor pressures than those of gram-negative bacteria and this is because they are much thicker (Beveridge, T. J. 1988 Can. J. Microbiol. 34:363–372). The *S. aureus* cell wall contains ~25–30 layers of peptidoglycan as opposed to ~1–3 layers in *E. coli* and *P. aeruginosa* (Beveridge, T. J., 1981 Int. Rev. Cytol. 12:229–317). Presumably, then, hydrolysis of the outer peptidoglycan layers of *S. aureus* walls would not be as serious for the microorganism as for a gram-negative bacterium even if it is at a localized point in the wall as for a MV attack. In fact, n-MVs had almost no effect on *S. aureus* cultures when compared to the control (FIG. 23*a*) even though we know that hydrolysis must have occurred (FIGS. 20 to 22). It was only when gentamicin plus autolysin (i.e., g-MVs) acted together that there was a discernible loss in viability using a MV system (FIG. 23(*a*)).

*P. aeruginosa* 8803 is an especially interesting case since it is a strain which possesses permeability resistance against aminoglycoside antibiotics such as gentamicin (Bryan L. E. et al, supra). This accounts for the (almost) direct correspondence between the control culture and the culture subjected to soluble gentamicin (FIG. 23(*d*)). In this case the soluble antibiotic concentration was 100 µg/ml of gentamicin. n-MVs had a profound lytic effect on the culture and the effect of g-MVs was even more drastic (i.e., a drop of ~1 log 10 between the two MV systems); it, again, is presumably due to the combined action of the antibiotic and hydrolytic enzyme. Since this is a permeability resistant strain which blocks the entrance of gentamicin at the outer membrane level, this dual killing action emphasizes the lytic power of a MV system. Gentamicin could only enter these cells because it was packaged into a bilayered MV which could fuse with the otherwise impermeable outer membrane and liberate its contents into the periplasmic space.

When the lytic action of n-MVs on *E. coli* DH5α, *P. aeruginosa* PAO1 and 8803 were compared it was apparent that the vesicles had more killing power on the 8803 strain. Although the general peptidoglycan chemotype (i.e., A1γ) is the same between the two bacterial genera (Schleifer, K. H. and O. Kandler. 1972 Bacteriol Rev. 36:407–471), there are frequently many subtle and varied chemical differences between the more minor constituents which make up the polymeric network of peptidoglycan which encompasses the cell. These can be at the species and strain level and require sophisticated analytical regimens for their detection (Altmaier, G., and E. R. Schmid 1993 New mass spectrometric methods for peptidoglycan analysis pp. 23–30 In M. A. de Pedro, J. V. Holtje and W. Loffelhardt (ed), Bacterial growth and lysis: metabolism and structure of the bacterial sacculus Plenum Press, N.Y.; Holtje, J. -V. and E. I. Tuomanen 1991 J. Gen. Microbiol 137:441–454; Pittenauer, E. G. et al., 1993. Structure elucidation of peptidoglycan monomers by fast atom bombardment and electrospray ionization tandem mass spectrometry. pp 39–46 and Pittenauer, E., et al, 1993 HPLC and 252 Cf plasma desorption-mass spectrometry of muropeptides isolated from *E. coli*. pp. 31–38. In M. A. de Pedro, J. V. Holtje and W. Loffelhardt (ed.), Bacterial growth and lysis: metabolism and structure of the bacterial sacculus Plenum Press, N.Y). Intuitively, distinct autolysins should have some discrimination over peptidoglycan chemistry and 8803 peptidoglycan should be closer in identity to PAO1 peptidoglycan than DH5α peptidoglycan (or *S. aureus* peptidoglycan which has an entirely different chemotype). Therefore, if PAO1 autolysins cannot be regulated by strain 8803 (and it appears they cannot), the PAO1 autolysins in a n-MVs should have more hydrolytic power on 8803 peptidoglycan than that of DH5α. This was the case (cf. FIGS. 23(*b*) and 23(*d*)).

The study confirms that both types of MVs were enriched with peptidoglycan hydrolases (autolysins). Autolysins are defined as a group of endogenous enzymes that hydrolyze the various bonds present in peptidoglycan resulting in damage to the integrity of murein sacculus or cell wall. The study also confirmed that n-MVs have bactericidal activity on intact peptidoglycan-containing bacteria.

g-MVS liberate both autolysin and gentamicin into the cell surfaces of gram-negative and gram-positive bacteria so that the killing capacity is substantially increased i.e. a synergistic effect is observed. So much so that much lower quantities of antibiotic are required for a bacteriolytic effect. It is also apparent that g-MVs are effective against strains of bacteria which are normally impermeable to the antibiotic.

Detailed Description of FIGS. 18 to 23

FIG. 18 is an electron micrograph of negatively stained g-MVs. Note that the spherical MVs are of various sizes (50–150 nm) possess an intact bilayer (small arrow) and enclose electron-dense material (large arrow) Bar=100 nm.

FIG. 19 is an electrophoretic profile (zymogram) of autolysin from MVs. Band with cell wall degrading enzyme activity were observed as clear zones in the opaque gel containing peptidoglycan fragments. Although the material subjected to zymogram analysis were standardized g-MV appear to have higher endopeptidase activity. A barely visible band ~23 kDa is also visible in g-MV.

FIG. 20 are electron micrographs of purified sacculi from (A) *S. aureus* and (B) *E. coli* (C) *S. aureus* and (D) *E. coli* sacculi after incubating with MVs from *P. aeruginosa*. Note that several areas of MV treated sacculi undergoing lysis in both gram-positive and gram-negative cell wall (arrow). this demonstrates the MVs capacity to hydrolyse the peptidoglycan from both gram-positive and gram-negative bacteria.

FIG. 21 shows chromatographic separation of the products of action of *P. aeruginosa* MVs on glycyl-peptides. It demonstrates that the enzyme catalyzed the hydrolysis of peptidoglycan fragments suggesting the MV to contain enzymes capable of lysing bacteria by acting on the rigid cell wall peptidoglycan.

FIG. 22 shows fusion of *P. aeruginosa* MVs with (A) *E. coli* and (B) *S. aureus*. Immunogold electron microscopic labeling of thin-sections with antibodies to *P. aeruginosa* LPS demonstrates the firm integration of MV. Note that the gold particles specifically labeled the MV (small arrow). The firm integration of MVs with bacteria is clearly visible. Note the disintegration of cell wall (large arrow).

FIG. 23 are graphs showing the bactericidal effect of n-MV (▲) g-MV (♦) and gentamicin (●) on (a) *S. aureus* $D_2C$, (b) *E. coli* DH5α (c) *P. aeruginosa* PAO1 and (d) *P. aeruginosa* 8803. n-MV g-MV or gentamicin were added to viable cells and viability was monitored over 5 h. The control (■) contained cells with no MVs or gentamicin. The soluble gentamicin concentration in incubating media for strain a, b, and c were 2.5×MIC and 100 µg/ml for strain 8803.

Example 7

Materials and Methods

Isolation of MVs

MVs were isolated form exponentially growing cells of *Pseudomonas aeruginosa* PAO1 serotype O5 and *Shigella flexneri* M90T serotype 5 (Sansonetti, P. J. et al. 1986 Infect. Immun. 51:461–469) as outlined above. Briefly, cells from 0.5 liter cultures grown in Trypticase soy both (TSB) were removed from suspension by centrifugation at 6,000×g for 15 min. The supernants were filtered sequentially through 0.43- and 0.22-µm-pore size cellulose acetate membranes (MSI, Westbro, Mass.) to remove residual cells. MVs were removed from the resulting filtrates by centrifugation at 150,000×g for 3 h at 5° C. and vesicle pallet was washed and resuspended in phosphate buffered saline (PBS;pH 7.4).

Integration of MVs with Ty21a

Exponentially growing cultures of *Salmonella typhi* Ty21a (Swiss Serum and Vaccine Institute, Berne, Switzerland) in TSB were washed and diluted in PBS, pH 7.4, to produce a bacterial suspension of $10^8$ CFU/ml. These were mixed 4:1 with a MVs suspension (each MV preparation at 100 µg protein/ml) for either PAO1 or M90T, or a mixture from both strains, and incubated at 37° C. for 15 min. The unbound MVs were removed for the cells by centrifugating the cell-MV suspension at 6,000×g for 15 min. This was followed by resuspending the pellet in PBS and sequential filtration through 0.45- and 0.22-µm-pore size cellulose acetate membranes. Finally, 10 ml of PBS were passed through the filters to remove unbound MVs. Samples were examined by transmission electron microscopy (TEM) to confirm complete removal of non-integrated MVs from cell suspension.

SDS-PAGE and Western Immunobloting

MVs, OMPs and whole cells (WC) were boiled for 10 min in sample buffer (60 mM Tris [pH 6.8] 10% glycerol, 2% SDS, 0.05% bromophenol blue, 1 µl of β-mercaptoethanol) and resolved in a 13% plyacrylamide gel stained with Commassie brilliant blue. A 40 µg-sample of protein was digested with proteinase K (10 µg/ml) separated in SDS-PAGE, transferred onto nitrocellulose and the integrated antigens were detected by incubation with either monoclonal antibodies for *P. aeruginosa* B-band serotype O5 or polyclonal antibodies to the purified LPS form M90T (Kadurugamuwa J. L. et al 1992. Infect. Immun. 59:3463–3471).

Immunolabelling

The fusion of MVs from M90T and PAO1 with Ty21a was demonstrated by immunogold labeling of whole mounts and thin sections using LPS-specific polyclonal antibodies to M90T or monoclonal antibodies to PAO1 LPS (Silver, M. M. et al, 1988 J. Histochem, Cytochem. 36: 1031–1036).

Mouse Immunization

Mouse Immunization: Six-to seven week old female BALB/c mice (in groups of six) were immunized orally via a gavage tube, with 0.3 ml of one of the following test vaccines: (i) Ty21a ($2\times10^8$ CFU/ml); (ii) PAO1 MVs (100 µg protein/ml); (iii) M90T MVs (100 µg protein/ml); (iv) Ty21a ($2\times10^8$ CFU/ml)+M90T MVs (at 100 µg protein/ml) (v) Ty21a ($2\times10^8$ CFU/ml)+PAO1 MVs (100 µg/ml); (vi) Ty21a ($2\times10^8$ CFU/ml)+PAO1 MVs+M90T MVs (at 100 µg protein/ml); and, (vii) a control group with 0.3 ml sterile PBS. All vaccines were suspended immediately before immunization in 3% $NaHCO_3$ in PBS at pH 8.0, and given four times at one week intervals. One week after the final immunization, mice were sacrificed, bled and the serum was collected. Bronchoalveolar washings were obtained as described in Guzman, C. A. et al, 1991, Infect. Immun. 59:4391–4397. Briefly, trachea and lungs were aspirated with 2.0 ml of ice-cold PBS containing 2 mM phenylmethylsulfonylfluoride (PBS—PMSF as a protease inhibitor) (Sigma Chemical Co., St. Louis, Mo.), three times to get an even distribution of the solution between each lung, before collecting the final fluid having a volume of 0.6–0.8 ml. Gut washes were obtained by washing the complete gut segment which was distal from the stomach with 1.5 ml ice-cold PBS—PMSF. The washings were centrifuged at 3000×g for 10 min. at 4° C. to remove cellular debris and stored at −20° C. until tested.

Antibody Responses

MVs-specific antibodies in serum and mucosal washes, were determined by an enzyme-linked immunosorbent assay (ELISA) (Guzman, C. A. et al., 1991 Infect. Immun. 59:4391–4397) using plates coated with 100 µl bacterial suspension ($10^8$ CFU/ml) as the solid-phase antigen either with M90T or PA01. Samples for ELISA were diluted (serum 1:25, gut washes 1:50 and lung washes 1:10) in PBS. The amount of antigen-specific IgA, IgG and IgM were determined with alkaline phosphatase-conjugated goat anti-mouse IgA 1:1000 ((α chain), IgG 1:3000 (γ+L CH. Sp) and IgM 1:3000 (µ) (Cedarlane, Ontario, Canada) with p-nitrophenylphosphate (Bio-Rad Laboratories Ltd., Ontario, Canada) as the substrate. All samples were processed simultaneously on the same day, and mouse serum from the control group and control lung or gut washes were used as the blank for ELISA readings.

To investigate which immunological responses in immunized mice were directed against LPS or OMPs, Western blot analysis was performed using either PAO1 or M90T whole cells as antigens, treated with either sample buffer or Proteinase-K (Sigma). Antibody recognizing M90T or PAO1 antigens in body fluids were detected with alkaline phosphatase conjugated goat anti-mouse IgA, IgG and IgM as describe before.

Experimental Results

TEM and SDS-PAGE Analyses of MVs

By electron microscopy of thin sections isolated, purified MVs from *S. flexneri* strain M90T and *P. aeruginosa* stain PAO1 were bilayered spherical vesicles ca. 80 nm in diameter and (most) were filled with a particulate substance. The protein profiles of whole cell lysates, OMPs (extracted for whole cells), and MVs from M90T and PAO1 were compared by SDS-PAGE (FIG. 24(a)). The banding patterns of M90T MVs were similar, but not identical, to the corresponding OMPs from whole cells; the major ~35 and 37 kDa. The prominently stained MV bands from PAO1 included ~-45 and 55-kDa proteins which were also prominent in the whole cell OMP fraction.

Fusion of MVs with Ty21a as the Attenuated Vaccines was Constructed

Figure 24:
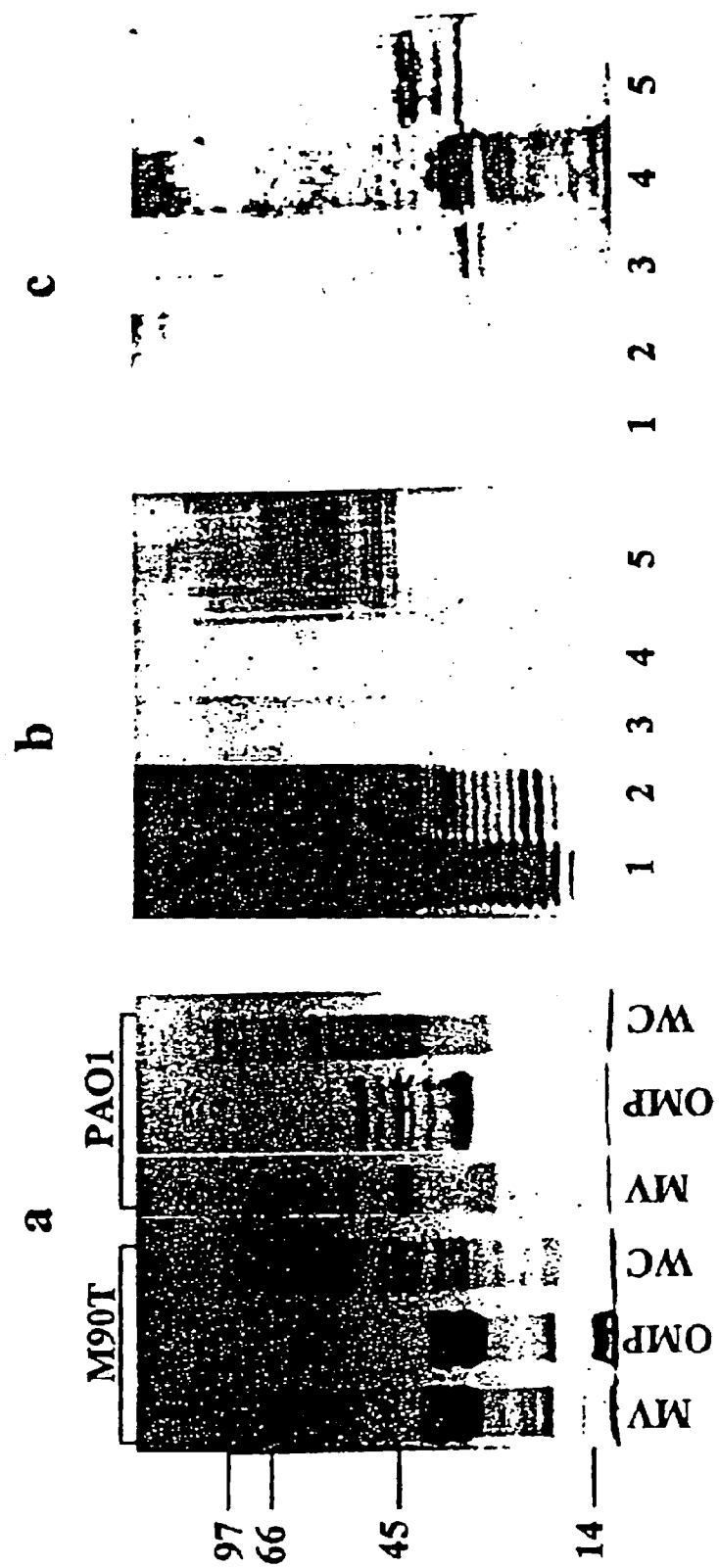
FIG. 24 are SDS-PAGE protein profiles of M90T and PAO1 MVs, OMPs, and whole cells (WC) (a) and Western immunoblots demonstrating the integration of MVs with Ty21a (b) and (c)
Figure 25:
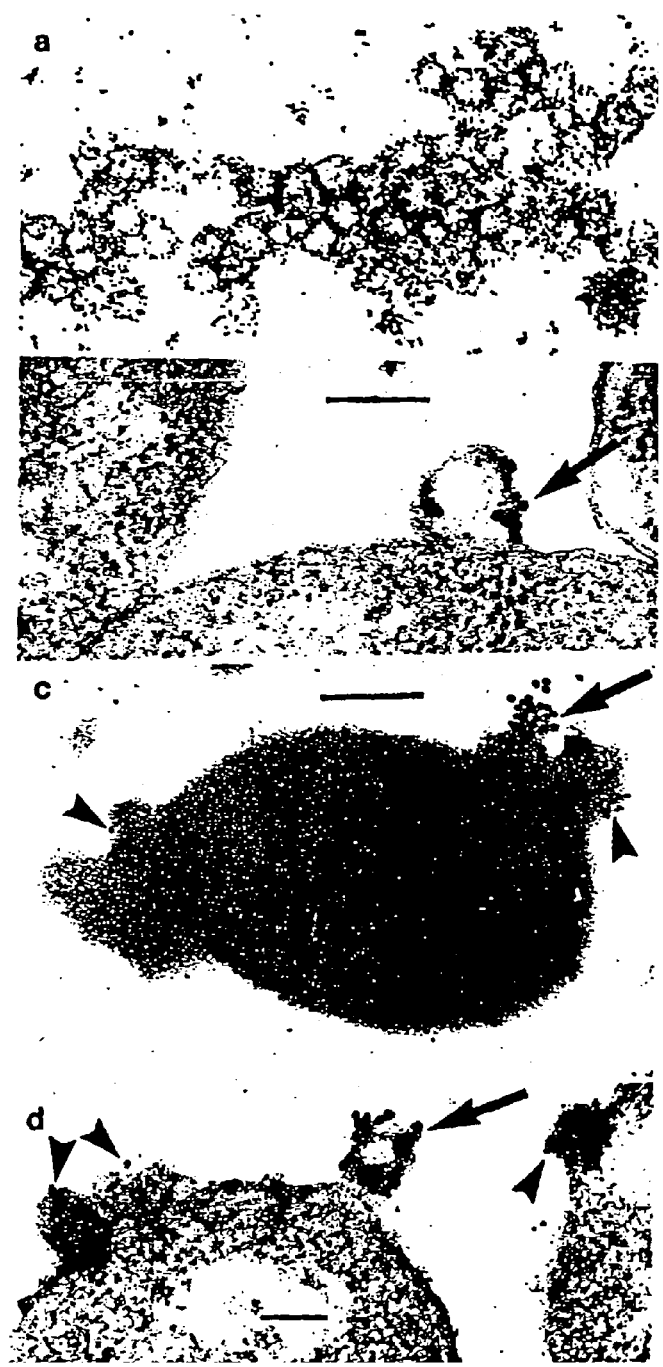
FIG. 25 shows the immunogold electron microscopic detection of whole mounts of PAO1 LPS (a) on purified MVs from PAO1 (b) thin-sections of Ty21a after fusion with PAO1 MVs; and double labeling of (c) whole mounts and (d) thin-sections of Ty21a during MV fusion.

The firm integration of M90T and PAO1 LPS antigens into Ty21a was confirmed using Western immunoblots (FIGS. 24(b) and 24(c)) and TEM (FIG. 25) using anti-LPS antibodies. The banding pattern and immunoreactivities of the PAO1 LPS that was integrated into Ty21a were subtly different to those of PAO1 whole cells or MVs (FIG. 24(b) and suggested selective integration. Only the middle portion of the ladder-like banding pattern in immunoblots reacted with PAO1 antibodies; possibly only a certain population of MVs were integrated (FIG. 24(b) lanes, 1, 2 and 5). A difference was also detected with integrated M90T LPS; this was not as apparent as with PAO1 (FIG. 24(c) lanes 3, 4 and 5). M90T or PAO1 anti-LPS antibodies did not react with 'non-integrated', control Ty21a cells.

Immunogold labeling of MV-treated Ty21a with LPS-specific antibodies illustrated the topographic distribution of attached MVs (FIGS. 25(b), (c) and (d)). Thin-sections substantiated the bilayer fusion of MVs whereas "double labeling" proved that LPS form both PAO1 and M90T were each concomitantly integrated into a single bacterium (FIG. 25(d)). The integrated antigens were highly stable in Ty21a since they could still be labeled by the Western and TEM techniques after several months at 4° C., and after freezing and thawing the treated cells.

Antibody Responses Specific for MVs in Vaccinated Mice

Figure 26:
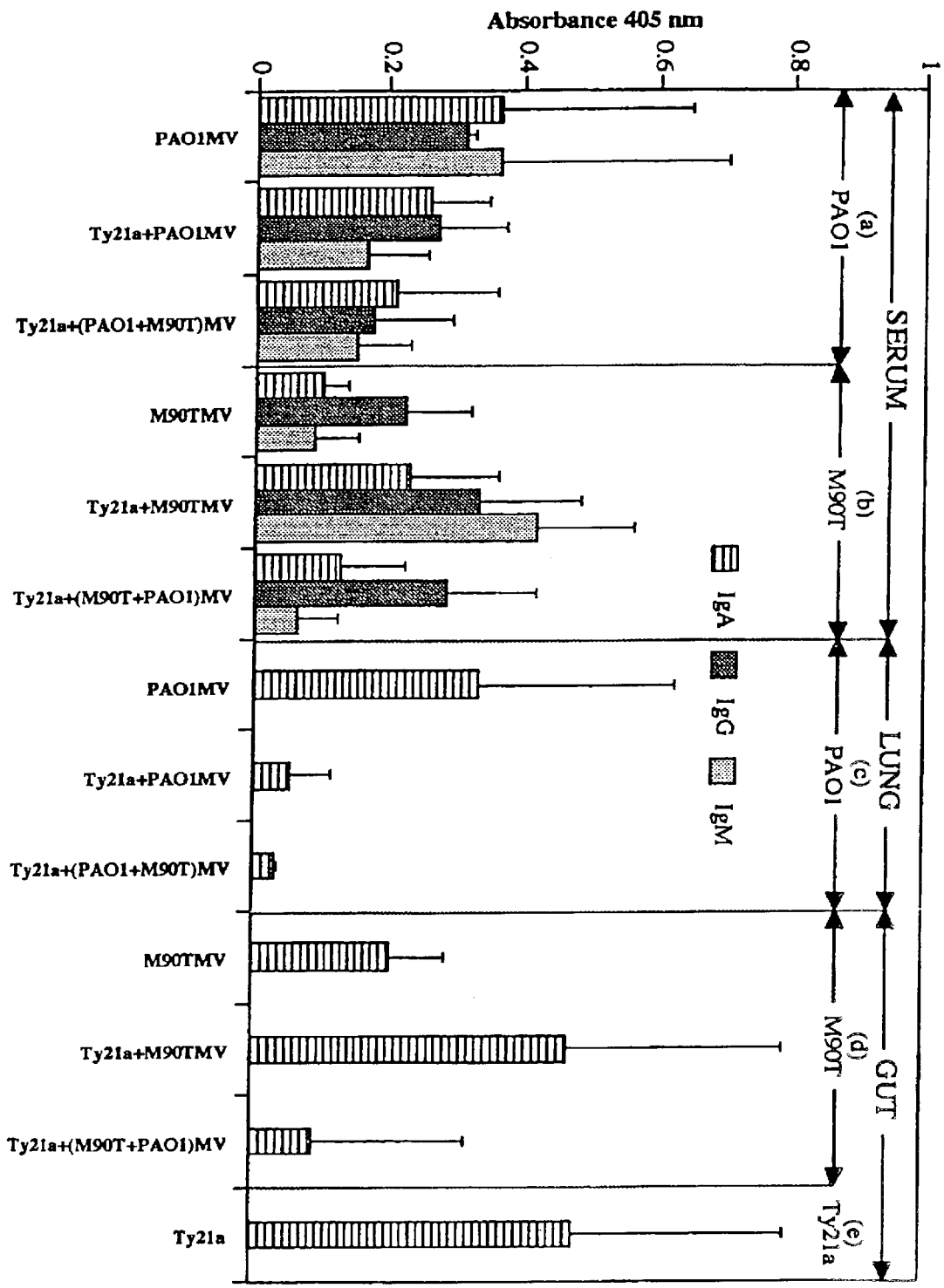
Figure 27:
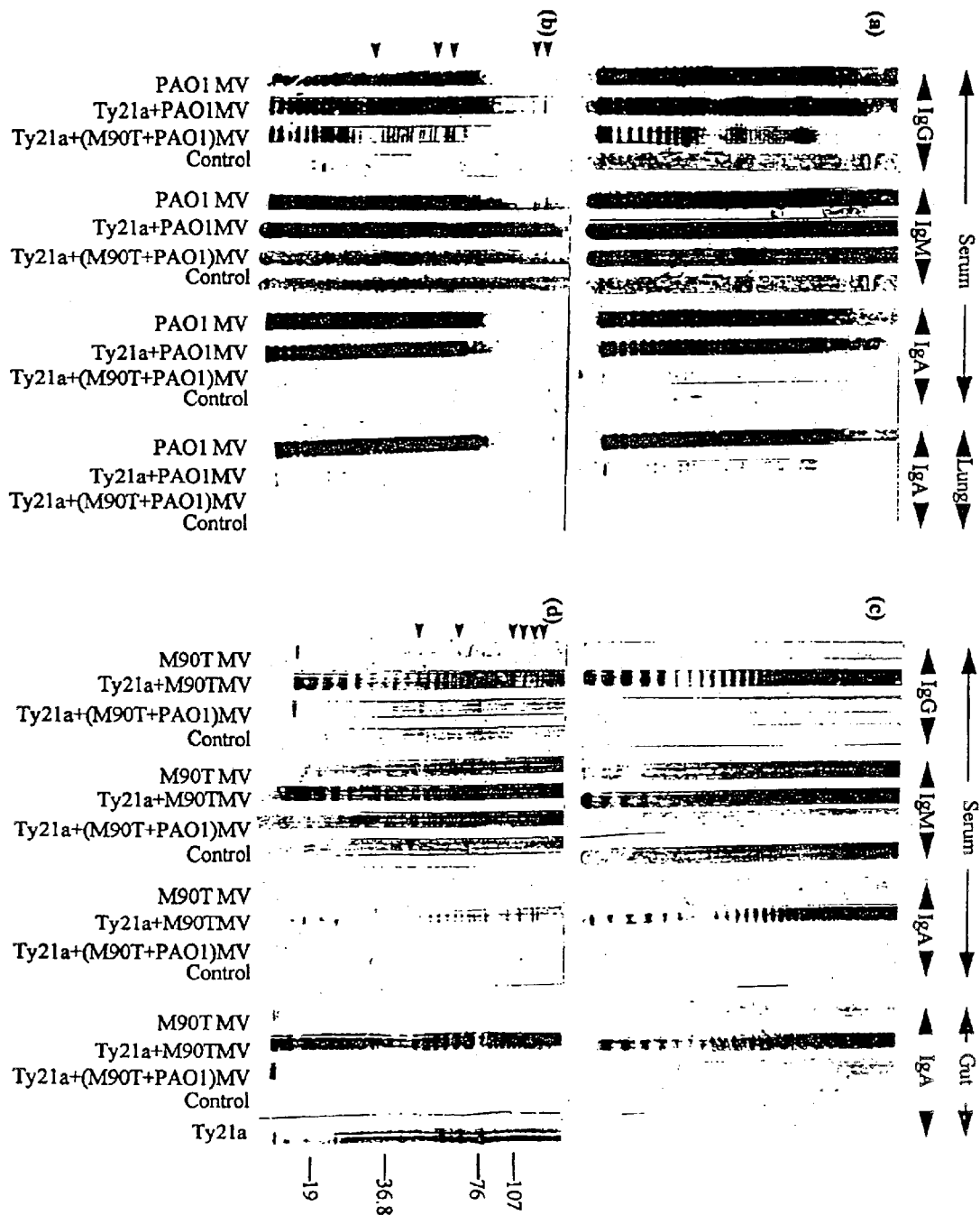
FIG. 27 shows the reactivity of the sera or of mucosal washings from immunized mice on Western immunoblots.

To determine the immunogenicity of the constructs, serum IgA, IgG and IgM and mucosal (lung and gut) IgA antibody titers in orally immunized BALB/c mice were analysed by ELISA (FIG. 26). Immunization of mice with PAO1 MVs alone elicited a higher antigen-specific antibody response in serum and lung than in the group immunized with the Ty21a carrier strain with integrated PAO1 MVs. This difference is more noticeable with lung lavage than with serum (FIGS. 26(a) and 26(b)). In contrast, M80T-specific antibody titers in both serum and gut washes were higher when M90T MVs were delivered after integration into the carrier strain (FIGS. 26(b) and 26(d)). However, these titers declined when PAO1 MVs were incorporated into the Ty21a+M90T MV construct. A decrease in PAO1-specific antibody titer was also evident in serum and lung washes when M90T MVs were integrated into the Ty21a+PAO1 MVs vaccine contruct (FIGS. 26(a) and 26(c)). However, this decrease was not as pronounced as was seen after integration of PAO1 MVs. The decline in antigen-specific antibody response after incorporation of PAO1 MVs into the carrier strain is presumably due to a general weakening of the cell envelope of the Ty21a strain by PAO1 MVs which lowered the total capacity of the carrier strain to deliver the antigens to the gut-associated lymphoid tissues. In separate experiments, a decrease was observed in viable Ty21a cells within 0.5 h following integration of PAO1 MVs into Ty21a. A reduction in viable Ty21a cells was also observed when M90T MVs were added to the carrier strain. However, this reduction was only 5% as opposed to 40% by PAO1 MVs. Even with the reduction in cell numbers, clear immune responses were seen in the mice (FIG. 26). The IgA antibody response in the gut washing to the Ty21a strain alone and the MVs constructs was the lowest in lung washes (FIG. 26(c)). This is due to the higher dilution of the mucosal fluid with the PBS which was needed for sampling. Higher values were obtained with more concentrated samples; however, it was not possible to conduct several assays on such small volume samples. Despite sone of these low ELISA values, diluted samples reacted by Western blot analysis (FIG. 27). Strain-specific IgA, IgG, and IgM were detected in serum with subtle differences between the immunoglobulin classes for PAO1 MVs alone or after integration with TY21a. These differences were more noticeable for M90T (FIGS. 26(a) and 26(b)). The IgA antibody response in gut washings to Ty21a confirmed the strain ability to elicit an immune response (FIG. 26(e)).

Serum or mucosal samples in which specific immunoglobulins could be detected by ELISA were next analysed by Western blotting to determine whether the induced antibodies were directed against LPS or protein antigens (FIG. 27). Samples were analysed for serum IgA, IgG and IgM and mucosal IgA with sample buffer or proteinase-K treated M90T or PAO1 whole cells as the antigen. Proteinase-K treatment was used to de-proteinize the antigenic samples so that those antibodies directed against LPS in the body fluid could more easily be detected. Strong anti-LPS antibodies were evident for both M90T and PAO1-specific LPS. The IgA, IgG, and IgM responses to the various vaccine constructs showed a similar trend to that previously seen in ELISA tests. The antibody response to M90T MVs was weak with barely detectable bands on Western blots (FIG. 26). Immunoblotting of non-deproteinized samples with serum, lung, or gut washes revealed several immunoreactive protein-specific antibody responses (arrows) to the PAO1 (FIG. 27(b)) and M90T (FIG. 27(d)) vaccine constructs. The reactivity of immunoglobulin classes to the various vaccine constructs was similar to the ELISA results. On these immunoblots, the LPS-specific antibody response was also visible for both PAO1 and M90T and, in fact, dominated the protein responses when the two overlapped. The spacing and banding patterns were more extensive and complicated in these immunoblots than those treated with proteinase-K implying that the immune response is to both LPS and protein antigens. The antibody response to the prominent 35–37 kDa and 45–55 kDa protein bands of M90T and PAO1 (FIG. 24(a)) became evident when LPS-specific antibodies were removed from body fluids by adsorbing them out with either M90T or PAO1 LPS. The antibody response to the carrier strain, Ty21a, was mainly protein-specific (FIG. 27(d)). This was to be expected, since the growth conditions employed did not promote complex side chain LPS expression in Ty21a.

This study has confirmed the highly specific antigenic factors from two gram negative pathogens (*P. aeruginosa* and *S. flexneri*) can be introduced into an attenuated *Salmonella* strain (Ty21a) by the MV-fusion technique and that the resulting vaccine induces humoral and mucosal responses against the introduced antigens.

Detailed Description of FIGS. 24 to 27

FIG. 24

SDS-PAGE protein profiles of M90T and PAO1 MVs, OMPs, and whole cells (WC) (a). Each lane contains 25 μg protein. Numbers in left margin denote $M_r$ in kDa. Western immunoblots to demonstrate the integration of MVs with Ty21a (b) and (c). The immunoblots in FIG. 24(*b*) was reacted against antibodies to the LPS of PAO1 whereas that in FIG. 24(*c*) was reacted against antibodies to the LPS of M90T. Lane 1. PAO1 whole cells, PAO1 MVs, 3. M90T whole cells, 4. M90T MVs, and 5. Ty21a whole cells+M90T MV+PAO1 MVs. Neither of the antibodies reacted against surface components of Ty21a.

FIG. 25

Immunogold electron microscopic detection of whole mounts of PAO1 LPS (a) on purified MVs from PAO1 and (b) thin-sections of Ty21a after fusion with PAO1 MVs. Gold particles surround the MVs as they attach and fuse to bacterium (arrow). Similar results were obtained with M90T Mvs when labeled. Double labeling of (c) whole mounts and (d) thin-sections of Ty21a during MV fusion demonstrated the simultaneous integration of the two separate antigens (M90T LPS, arrow head) and (PAO1 LPS, arrow) into the surface of the attenuated strain. Bar=100 nm. Bilayer fusion of MVs with Ty21a outer membrane is clearly seen indicating that heterologous antigens can be incorporated into a vaccine strain using our MV system.

FIG. 26

Levels of specific antibody responses in sera, lung and gut in mice following oral immunization with MVs from PAO1 or M90T or after integration of the MVs onto Ty21a vaccine strain. PAO1 or M90T antigen-IgA, IgG and IgM or Ty21a anti-IgA titers were determined by ELISA using PAO1, M90T or Ty21a a whole cells as specific antigens. The immunizing agent is shown on the X-axis. Panels (a) to (e) depict the strain-specific antibody responses in serum to (a) PAO1 and (b) M90T, in lung to (c) to PAO1, and to intestinal lavage fluids to (d) M90T and (e) Ty21a. Columns represent the specific antibody classes IgA, IgG and IgM in sera and IgA response in mucosal washings. The values for control mice body fluids were subtracted from those of immunized mice before these results were tabulated. Standard deviations represent variations between individual mouse samples in each group of six mice.

FIG. 27

Reactivity of the sera or of mucosal washings from immunized mice on Western immunoblots. (a) and (c) are proteinase-K treated PAO1 and M90T whereas (b) and (d) are untreated PAO1, M90T and Ty21a so that both LPS and OMP reactions are seen. The Immunizing agent is shown in bottom panel. Arrowheads denote the protein antigens recognized by immunized mice sera or mucosal washings. Strain-specific serum IgA, IgG and IgM and mucosal IgA antibody responses were analyzed using PAO1, M90T or Ty21a whole cells as antigens. Molecular size standards are indicated to the right in kDa.

Having illustrated and described the principles of the invention in a preferred embodiment, it should be appreciated to those skilled in the art that the invention can be modified in arrangement and detail without departure from such principles. We claim all modifications coming within the scope of the following claims.

TABLE 1

| Microorganism | Disease | Antigens/Enzymes |
|---|---|---|
| *Pseudomonas aeruginosa* | burn victim's infection<br>cystic fibrosis<br>corneal infection<br>nosocomial (hospital-associated) infections | endotoxin (A- and B-band lipopolysaccharide) (LPS)<br>outer membrane proteins<br>protease<br>phospholipase C<br>proelastase<br>autolysins<br>pilin (from pili)<br>flagellin (from flagella) |
| *Escherichia coli* | gastrointestinal infection<br>enterotoxin (verrotoxin)<br>infection (ETEC) | LPS<br>outer membrane proteins<br>pilin<br>flagellin<br>periplasmic verrotoxin<br>hemolysin |
| *Salmonella gastroenteritis* (typhimurium)<br>*S. typhi*<br>*S. entriditis* | *Salmonellosis*<br>typhoid fever<br>food poisoning | LPS<br>outer membrane proteins<br>flagellin<br>hemolysin |
| *Shigella flexneri*<br>*S. sonnei*<br>*S. dysenteriae* | shigellosis<br>food poisoning | LPS<br>outer membrane proteins<br>invasive protein<br>shiga toxin |
| *Neisseria gonorrhoeae* | gonococcal sexually transmitted infections | LPS<br>outer membrane proteins |
| *N. meningitidis* | bacterial meningitis | LPS<br>outer membrane proteins |
| *Haemophitus influenzae* | bacterial meningitis<br>bacterial flu | LPS<br>outer membrane proteins<br>capsular polysaccharide |
| *H. pleuropneumoniae* | pneumonia | LPS<br>outer membrane proteins |
| *Pasteurella haemolytica* | shipping fever<br>animal pneumonia | LPS<br>outer membrane proteins |
| *P. multocida* | fowl cholera | LPS<br>outer membrane proteins |
| *Legionella pneumophila* | legionnaire's disease<br>legionellosis<br>Pontiac fever | LPS<br>outer membrane proteins |
| *Treponema pallidum*<br>*T. denticola*<br>*T. orale* | syphilis, yaws<br>peridontal disease | LPS<br>outer membrane proteins<br>endoflagellin |
| *Borrelia burgdorferi*<br>*Borrelia spp.* | lyme disease<br>relapsing fever (borreliosis) | LPS<br>outer membrane proteins<br>endoflagellin |
| *Leptospira interrogans* | leptospirosis | LPS<br>outer membrane proteins<br>endoflagelhn<br>S. layer protein |
| *Klebsiella pneumoniae* | pneumonia<br>bacteremia | LPS<br>outer membrane proteins<br>capsular polysaccharide |
| *Proteus vulgaris*<br>*P. morganii*<br>*P. mirabilis* | proteus infections (usually urinary tract) | LPS<br>outer membrane proteins<br>flagellin |
| *Rickettsia prowazeki* | louse-borne typhus | LPS<br>outer membrane proteins |
| *R. typhi* | endemic (murine) typhus | LPS<br>outer membrane proteins |
| *R. rickettsii* | rocky mountain spotted fever | LPS<br>outer membrane proteins |

TABLE 1-continued

| Microorganism | Disease | Antigens/Enzymes |
|---|---|---|
| Porphyromonas (Bacteriodes) gingivalis | periodontal disease | LPS outer membrane proteins protease |
| Chlamydia psittaci | psittacosis | LPS |
| C. pneumoniae | pneumonia | outer membrane proteins |
| C. trachomatis | conjunctivitis | |
| Campylobacter jejuni | gastroenteritis | LPS |
| C. intermedis | bacterial ulcers | outer membrane proteins flagellin |
| C. fetus (subspfetus) | spontaneous abortion | |
| Helicobacter pylori | gastroenteritis ulcers (peptic) colon cancer | LPS outer membrane proteins flagellin |
| Francisella Tularensis | tularemia | LPS outer membrane proteins |
| Vibrio cholerae | cholera | LPS outer membrane proteins flagellin |
| Vibrio parahaemolyticus | enteritis | |
| Bordetella pertussis | pertussis | LPS outer membrane proteins pertussis toxin |
| Burkholdenia pseudomallei | melioidosis | LPS outer membrane proteins |
| Brucella abortus | brucellosis of cattle, pigs, goats and dogs | |
| B. suis | | |
| B. melitensis | | |
| B. canis | human brucellosis | |
| Spirillum minus | rat-bite fever | LPS outer membrane proteins flagellin |
| Pseudomonas mallei | "glanders" of horses | LPS outer membrane proteins |
| Aeromonas hydrophila | gastroenteritis cellulitis | LPS outer membrane proteins S-layer protein |
| A. salmonicida | furunculosis of fish | LPS outer membrane proteins S-layer protein |
| Yersinia pestis | plague | LPS outer membrane proteins |

Table 2

Distribution of extracellular enzymes in membrane vesicles and cellular extracts

| | ENZYME ACTIVITY | | | |
|---|---|---|---|---|
| Sample | Protease U/μg protein[a] | Elastase U/μg protein[b] | PLC U/μg protein[c] | Alk. Phosphatase U/μg protein[d] |
| n-MV | 1.68 ± 0.26 | <0.01 | 3.45 ± 0.18 | 1.0 ± 0.02 |
| g-MV | 1.69 ± 0.27 | <0.01 | 3.47 ± 0.24 | 0.85 ± 0.07 |
| WCC | 0.07 ± 0.01 | <0.01 | 0.98 ± 0.08 | 0.71 ± 0.13 |
| WCG | 0.08 ± 0.02 | <0.01 | 0.78 ± 0.02 | 0.47 ± 0.08 |

[a]Units in hide powder blue assay. One unit = increase in $A_{505}$ of 0.1 per h at 37° C.
[b]Units in elastin Congo-red assay. One unit = increase in $A_{405}$ of 0.1 per 2 h at 37° C.

Table 2-continued

Distribution of extracellular enzymes in membrane vesicles and cellular extracts

[c]Units in NPPC assay. One unit = increase in $A_{405}$ of 0.1 per h at 37° C.
[d]Units in pNPP assay. One unit = increase in $A_{595}$ of 0.1 per h at 37° C.
WCC, control whole cell extract.
WCG, gentamicin treated whole cell extract.
Alk., Alkaline.
All assays were done in triplicate in each of three separate experiments, and the results were averaged. Mean ± SD.

TABLE 3

Enzyme activities in cell-free culture supernatants following the removal of MVs.

| | % Activity remaining in cell-free supernatant after removal of MVs | |
|---|---|---|
| Enzyme | n-MV | g-MV |
| PLC | 32 ± 8 | 17 ± 5 |
| Alk. phosphatase | 49 ± 7 | 52 ± 6 |
| Elastase | 98 ± 0.8 | 98 ± 0.9 |
| Protease | 87 ± 1.9 | 75 ± 4 | abbreviations as in Table 2.

TABLE 4

DNA content in MVs derived from two strains of *P. aeruginose*.

| Strain | Content | Solubilized[a] ng DNA/mg Protein ± SD | Intact ng DNA/mg Protein ± SD |
|---|---|---|---|
| ATCC 19660 | n-MV | 18.85 ± 0.63 | 14.35 ± 0.49 |
| | g-MV | 21.44 ± 0.33 | 16.12 ± 1.02 |
| H 103 | n-MV | 11.07 ± 0.89 | 7.69 ± 0.32 |
| | g-MV | 10.56 ± 0.48 | 8.87 ± 0.60 |

[a]Solubilized in Triton X-100 and ammonium hydroxide; abbreviations as in Table 2; mean ± SD, n = 4 for each estimate.

We claim:

1. An avirulent or attenuated bacterial cell composition comprising a membrane vesicle of a microorganism integrated into a cell surface of the bacterial cell, the membrane vesicle comprising a bilayer and an antigen associated with a surface of the membrane vesicle, wherein the amount of antigen is sufficient to trigger antibody production and wherein the antigen is derived from tbe same microorganism as the membrane vesicle.

2. The composition according to claim 1 wherein the microorganism is a microorganism, which produces natural membrane vesicles.

3. The composition according to claim 1 wherein the microorganism is selected from the group consisting of *Pseudomonas aeruginosa*, *Escherichia coli*, *Salmonella gastroenteritis* (*typhimurium*), *Salmonella typhi*, *Salmonella enteriditis*, *Shigella flexneri*, *Shigella sonnie*, *Shigella dysenteriae*, *Neisseria gonorrhoeae*, *Neisseria meningitides*, *Haemophilus influenzae*, *Haemophilus pleuropneumoniae*, *Pasteurella haemolytica*, *Pasteurella multilocida*, *Legionella pneumophila*, *Treponema pallidum*, *Tregonema denticola*, *Treponema orale*, *Borrelia burgdorferi*, *Borrelia* spp. *Leptospira interrogans*, *Kiebsiella pneumoniae*, *Pro-*

*teus vulgaris, Proteus morganii, Proteus mirabilis, Rickettsia prowazeki, Rickettsia typhi, Rickettsia richettsii, Porphyromonas (Bacteriodes) gingivalis, Chlamydia psittaci, Chlamydia pneumoniae, Chlamydia trachomatis, Campylobacter jejuni, Campylobacter intermedis, Camplobacter fetus, Heilcobacter pylori, Francisella tularenisis, Vibrio cholerae, Vibrio parahaemolyticus, Bordetella pertussis, Burkholderie pseudomallei, Brucella abortus, Brucella susi, Brucella melitensis, Brucella canis, Spirillum minus, Pseudomonas mallei, Aeromonas hydrophila, Aeromanas salmonicida,* and *Yersinia pestis.*

4. The composition according to claim 3 wherein the microorganism is selected from the group consisting of *Pseudomonas aeruginosa, Shigella flexneri, Shigella dysenteriae, Escherichia coli, Salmonella typhi,* and *Neisseria gonorrhoeae.*

5. The composition according to claim 1, wherein the membrane vesicle has a diameter of about 10 to about 200 nm, which is obtained by treating the microorganism with a surface-active agent, and is characterized by containing outer membrane, cytoplasmic membrane or plasma membrane, and cytoplasm components.

6. The composition according to claim 1 further comprising a second avirulent or attenuated bacterial cell having a second membrane vesicle of a second microorganism integrated into the cell surface of the second bacterial cell, the second membrane vesicle comprising a bilayer and an antigen associated with a surface of the second membrane vesicle, wherein the amount of antigen is sufficient to trigger antibody production in the second bacterial cell and wherein the antigen associated with a surface of the second membrane vesicle is derived from the same microorganism as the second membrane vesicle.

7. A composition according to claim 1 wherein the bacterial cell is selected from the group consisting of *Shigella, Salmonella, Vibrio,* and *Escherichia* cells.

8. The composition according to claim 7 wherein the bacterial cell is a *Salmonella typhi* Ty21a or a *Salmonella typhimurium* cell.

9. An avirulent or attenuated bacterial cell composition having a membrane vesicle integrated into a surface of the bacterial cell, the membrane vesicle having a bilayer and being derived from a pathogenic bacteria, wherein integration of the membrane vesicle with the surface of the bacterial cell provides antigenic factors produced by the pathogenic bacteria to the surface of the bacterial cell.

10. A method of producing a composition according to claim 9 comprising:

(a) incubating the avirulent or attenuated bacterial cell with the membrane vesicle derived from a pathogenic bacteria; and (b) selecting a bacterial cell having a membrane vesicle integrated into a surface of the bacterial cell.

* * * * *